(12) United States Patent
Ingersoll et al.

(10) Patent No.: US 12,714,450 B2
(45) Date of Patent: Aug. 25, 2026

(54) CONTROL OF IVL SYSTEMS, DEVICES AND METHODS THEREOF

(71) Applicant: Cardiovascular Systems, Inc., Santa Clara, CA (US)

(72) Inventors: Gregory B. Ingersoll, Minneapolis, MN (US); Jason W. Staab, Apple Valley, MN (US); Austin P. Petronack, Plymouth, MN (US); John R. Ballard, Waconia, MN (US); J. Samuel Batchelder, Woodinville, WA (US); Jacob T. Williams, Plymouth, MN (US); Donald D. Hanson, Shakopee, MN (US); Thomas D. Brindley, Plymouth, MN (US); Scott P. Boeshart, Plymouth, MN (US); Jeffrey T. Moriarty, Roseville, MN (US)

(73) Assignee: Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 19/431,242

(22) Filed: Dec. 23, 2025

(65) Prior Publication Data

US 2026/0114886 A1 Apr. 30, 2026

Related U.S. Application Data

(63) Continuation-in-part of application No. 19/170,999, filed on Apr. 4, 2025, which is a continuation of
(Continued)

(51) Int. Cl.
*A61B 17/22* (2006.01)
*A61B 17/00* (2006.01)

(52) U.S. Cl.
CPC .................. *A61B 17/22022* (2013.01); *A61B 2017/00199* (2013.01); *A61B 2017/00477* (2013.01);
(Continued)

(58) Field of Classification Search
CPC .... A61B 17/22022; A61B 2017/00199; A61B 2017/00477; A61B 2017/22025; A61B 2017/22062
See application file for complete search history.

(56) References Cited

U.S. PATENT DOCUMENTS 2,916,647 A 12/1959 George
3,412,288 A 11/1968 Ostrander
(Continued)

FOREIGN PATENT DOCUMENTS

AT E482647 T1 10/2010
AU 22933/88 A 4/1989
(Continued)

OTHER PUBLICATIONS

International Search Report and Written Opinion of International Application No. PCT/US2023/035025, mailed Jan. 18, 2024, 11 pp.
(Continued)

*Primary Examiner* — Timothy J Thompson
*Assistant Examiner* — Rhadames Alonzo Miller
(74) *Attorney, Agent, or Firm* — Workman Nydegger

(57) ABSTRACT

An intravascular lithotripsy (IVL) console is disclosed, comprising a power plug configured to couple to a mains power source, with the power plug extending outside an enclosure housing internal console circuitry. The console includes conductors coupled to the power plug and a first isolation barrier that electrically isolates power from the mains power source. The internal console circuitry includes low-voltage control circuitry and high-voltage power cir-
(Continued)

cuitry, which generates high-voltage pulses for emitters in a catheter. A second isolation barrier couples a first processor in the low-voltage control circuitry to a second processor in the high-voltage power circuitry. The second processor receives commands from the first processor and causes the high-voltage power circuitry to deliver high-voltage pulses to the emitters. The isolation barriers allow the power plug to supply power while the high-voltage power circuitry delivers pulses to the emitters.

20 Claims, 17 Drawing Sheets

Related U.S. Application Data application No. PCT/US2023/079209, filed on Nov. 9, 2023.

(60) Provisional application No. 63/874,995, filed on Sep. 3, 2025, provisional application No. 63/580,547, filed on Sep. 5, 2023, provisional application No. 63/424,573, filed on Nov. 11, 2022.

(52) U.S. Cl.
CPC .............. *A61B 2017/22025* (2013.01); *A61B 2017/22062* (2013.01)

(56) References Cited

U.S. PATENT DOCUMENTS 3,413,976 A 12/1968 Leo
3,524,101 A 8/1970 Barbini
3,583,766 A 6/1971 Padberg, Jr.
3,735,764 A 5/1973 Balev et al.
3,785,382 A 1/1974 Schmidt et al.
3,902,499 A 9/1975 Shene
3,942,531 A 3/1976 Hoff et al.
4,027,674 A 6/1977 Tessler et al.
4,030,505 A 6/1977 Tessler
4,191,189 A 3/1980 Barkan
4,445,509 A 5/1984 Auth
4,446,867 A 5/1984 Leveen et al.
4,587,975 A 5/1986 Salo et al.
4,608,983 A 9/1986 Mueller et al.
4,643,186 A 2/1987 Rosen et al.
4,654,770 A 3/1987 Santurtun et al.
4,662,126 A 5/1987 Malcolm
4,662,375 A 5/1987 Hepp et al.
4,671,254 A 6/1987 Fair
4,685,458 A 8/1987 Leckrone
4,697,588 A 10/1987 Reichenberger
4,702,248 A 10/1987 Mestas et al.
4,715,375 A 12/1987 Nowacki et al.
4,715,376 A 12/1987 Nowacki et al.
4,741,405 A 5/1988 Moeny et al.
4,766,608 A 8/1988 Cusick et al.
4,781,677 A 11/1988 Wilcox
4,793,329 A 12/1988 Mahler et al.
4,799,482 A 1/1989 Takayama
4,809,682 A 3/1989 Forssmann et al.
4,813,934 A 3/1989 Engelson et al.
4,878,495 A 11/1989 Grayzel
4,890,603 A 1/1990 Filler
4,900,303 A 2/1990 Lemelson
4,901,709 A 2/1990 Rattner
4,905,673 A 3/1990 Pimiskern
4,905,675 A 3/1990 Oppelt
4,909,252 A 3/1990 Goldberger
4,915,094 A 4/1990 Lacruche et al.
4,930,496 A 6/1990 Bosley, Jr.
4,936,281 A 6/1990 Stasz
4,955,143 A 9/1990 Hagelauer
4,955,377 A 9/1990 Lennox et al.
4,955,385 A 9/1990 Kvalo et al.
4,961,738 A 10/1990 Mackin
4,962,753 A 10/1990 Cathignol et al.
4,966,132 A 10/1990 Nowacki et al.
4,968,314 A 11/1990 Michaels
4,990,134 A 2/1991 Auth
4,994,032 A 2/1991 Sugiyama et al.
4,998,932 A 3/1991 Rosen et al.
5,002,085 A 3/1991 Fitzgerald
5,009,232 A 4/1991 Hassler et al.
5,040,548 A 8/1991 Yock
5,046,503 A 9/1991 Schneiderman
5,057,103 A 10/1991 Davis
5,057,106 A 10/1991 Kasevich et al.
5,057,107 A 10/1991 Parins et al.
5,061,240 A 10/1991 Cherian
5,072,723 A 12/1991 Viebach
5,078,717 A 1/1992 Parins et al.
5,102,402 A 4/1992 Dror et al.
5,103,804 A 4/1992 Abele et al.
5,116,227 A 5/1992 Levy
5,146,912 A 9/1992 Eizenhoefer
5,152,767 A 10/1992 Sypal et al.
5,152,768 A 10/1992 Bhatta
5,154,722 A 10/1992 Filip et al.
5,176,675 A 1/1993 Watson et al.
5,195,508 A 3/1993 Mueller et al.
5,211,683 A 5/1993 Maginot
5,231,976 A 8/1993 Wiksell
5,233,980 A 8/1993 Mestas et al.
5,245,988 A 9/1993 Einars et al.
5,246,447 A 9/1993 Rosen et al.
5,254,121 A 10/1993 Manevitz et al.
5,281,231 A 1/1994 Rosen et al.
5,295,958 A 3/1994 Shturman
5,304,134 A 4/1994 Kraus et al.
5,304,220 A 4/1994 Maginot
5,308,354 A 5/1994 Zacca et al.
5,320,634 A 6/1994 Vigil et al.
5,321,715 A 6/1994 Trost
5,324,255 A 6/1994 Passafaro et al.
5,336,234 A 8/1994 Vigil et al.
5,358,487 A 10/1994 Miller
5,362,309 A 11/1994 Carter
5,364,393 A 11/1994 Auth et al.
5,366,443 A 11/1994 Eggers et al.
5,368,591 A 11/1994 Lennox et al.
5,395,335 A 3/1995 Jang
5,395,361 A 3/1995 Fox et al.
5,411,016 A 5/1995 Kume et al.
5,417,208 A 5/1995 Winkler
5,425,735 A 6/1995 Rosen et al.
5,429,617 A 7/1995 Hammersmark et al.
5,431,663 A 7/1995 Carter
5,433,731 A 7/1995 Hoegnelid et al.
5,454,809 A 10/1995 Janssen
5,456,712 A 10/1995 Maginot
5,458,652 A 10/1995 Uebelacker
5,470,352 A 11/1995 Rappaport
5,472,406 A 12/1995 Torre et al.
5,474,080 A 12/1995 Hughes
5,520,645 A 5/1996 Imran et al.
5,571,167 A 11/1996 Maginot
5,582,578 A 12/1996 Zhong et al.
5,584,843 A 12/1996 Wulfman et al.
5,603,731 A 2/1997 Whitney
5,609,606 A 3/1997 O'Boyle
5,611,807 A 3/1997 O'Boyle
5,662,590 A 9/1997 Torre et al.
5,681,336 A 10/1997 Clement et al.
5,709,676 A 1/1998 Alt
5,741,246 A 4/1998 Prescott
5,749,375 A 5/1998 Maginot
5,766,152 A 6/1998 Morley et al.
5,836,874 A 11/1998 Swanson et al.
5,841,737 A 11/1998 Schaefer
5,846,218 A 12/1998 Brisken et al.
5,891,089 A 4/1999 Katz et al.

(56) References Cited

U.S. PATENT DOCUMENTS 5,893,840 A 4/1999 Hull et al.
5,931,805 A 8/1999 Brisken
5,967,984 A 10/1999 Chu et al.
5,979,455 A 11/1999 Maginot
5,995,871 A 11/1999 Knisley
6,001,069 A 12/1999 Tachibana et al.
6,007,530 A 12/1999 Doernhoefer et al.
6,033,371 A 3/2000 Torre et al.
6,056,722 A 5/2000 Jayaraman
6,080,119 A 6/2000 Schwarze et al.
6,083,232 A 7/2000 Cox
6,090,104 A 7/2000 Webster, Jr.
6,113,560 A 9/2000 Simnacher
6,123,718 A 9/2000 Tu et al.
6,132,444 A 10/2000 Shturman et al.
6,146,358 A 11/2000 Rowe
6,186,963 B1 2/2001 Schwarze et al.
6,210,408 B1 4/2001 Chandrasekaran et al.
6,215,734 B1 4/2001 Moeny et al.
6,217,531 B1 4/2001 Reitmajer
6,267,747 B1 7/2001 Samson et al.
6,277,138 B1 8/2001 Levinson et al.
6,287,272 B1 9/2001 Brisken et al.
6,287,331 B1 9/2001 Heath
6,352,535 B1 3/2002 Lewis et al.
6,364,894 B1 4/2002 Healy et al.
6,367,203 B1 4/2002 Graham et al.
6,371,971 B1 4/2002 Tsugita et al.
6,375,651 B2 4/2002 Grasso et al.
6,390,995 B1 5/2002 Ogden et al.
6,398,792 B1 6/2002 O'Connor
6,401,721 B1 6/2002 Maginot
6,406,486 B1 6/2002 Torre et al.
6,440,124 B1 8/2002 Esch et al.
6,456,888 B1 9/2002 Skinner et al.
6,464,660 B2 10/2002 Brisken et al.
6,494,890 B1 12/2002 Shturman et al.
6,500,174 B1 12/2002 Maguire et al.
6,514,203 B2 2/2003 Bukshpan
6,524,251 B2 2/2003 Rabiner et al.
6,589,253 B1 7/2003 Cornish et al.
6,599,313 B1 7/2003 Maginot
6,607,003 B1 8/2003 Wilson
6,635,054 B2 10/2003 Fjield et al.
6,638,246 B1 10/2003 Naimark et al.
6,652,547 B2 11/2003 Rabiner et al.
6,666,828 B2 12/2003 Greco et al.
6,666,834 B2 12/2003 Restle et al.
6,669,655 B1 12/2003 Acker et al.
6,689,089 B1 2/2004 Tiedtke et al.
6,726,681 B2 4/2004 Grasso et al.
6,736,784 B1 5/2004 Menne et al.
6,736,811 B2 5/2004 Panescu et al.
6,740,081 B2 5/2004 Hilal
6,755,821 B1 6/2004 Fry
6,758,847 B2 7/2004 Maguire
6,761,708 B1 7/2004 Chiu et al.
6,800,080 B1 10/2004 Bates
6,939,320 B2 9/2005 Lennox
6,954,977 B2 10/2005 Maguire et al.
6,989,009 B2 1/2006 Lafontaine
7,033,383 B1 4/2006 Maginot
7,066,904 B2 6/2006 Rosenthal et al.
7,087,061 B2 8/2006 Chernenko et al.
7,104,983 B2 9/2006 Grasso et al.
7,153,315 B2 12/2006 Miller
7,175,605 B2 2/2007 Tiedtke et al.
7,241,295 B2 7/2007 Maguire
7,247,269 B2 7/2007 Keidar
7,309,324 B2 12/2007 Hayes et al.
7,379,767 B2 5/2008 Rea
7,389,148 B1 6/2008 Morgan
7,390,308 B2 6/2008 Schultheiss
7,410,486 B2 8/2008 Fuimaono et al.
7,505,812 B1 3/2009 Eggers et al.
7,540,846 B2 6/2009 Harhen et al.
7,569,032 B2 8/2009 Naimark et al.
7,597,697 B1 10/2009 Maginot
7,628,785 B2 12/2009 Hadjicostis et al.
7,651,492 B2 1/2010 Wham
7,720,521 B2 5/2010 Chang et al.
7,736,362 B2 6/2010 Eberl et al.
7,744,595 B2 6/2010 Truckai et al.
7,744,620 B2 6/2010 Pedersen et al.
7,753,946 B2 7/2010 Maginot
7,754,047 B2 7/2010 Kelley
7,829,029 B2 11/2010 Zumeris et al.
7,837,672 B2 11/2010 Intoccia
7,850,685 B2 12/2010 Kunis et al.
7,853,332 B2 12/2010 Olsen et al.
7,855,904 B2 12/2010 Kirbie et al.
7,873,404 B1 1/2011 Patton
7,914,525 B2 3/2011 Abboud et al.
7,920,921 B2 4/2011 Syed et al.
7,942,850 B2 5/2011 Levit et al.
7,951,111 B2 5/2011 Drasler et al.
7,959,602 B2 6/2011 Tiedtke et al.
8,025,661 B2 9/2011 Arnold et al.
8,133,199 B2 3/2012 Weber et al.
8,162,859 B2 4/2012 Schultheiss et al.
8,177,801 B2 5/2012 Kallok et al.
8,182,530 B2 5/2012 Huber
8,197,463 B2 6/2012 Intoccia
8,241,272 B2 8/2012 Arnold et al.
8,277,444 B2 10/2012 Arnold et al.
8,333,763 B2 12/2012 Truckai et al.
8,343,170 B2 1/2013 Massicotte et al.
8,353,923 B2 1/2013 Shturman
8,366,705 B2 2/2013 Arnold et al.
8,382,771 B2 2/2013 Gellman et al.
8,444,639 B2 5/2013 Arnold et al.
8,518,038 B2 8/2013 Swanson
8,529,581 B2 9/2013 Massicotte et al.
8,556,813 B2 10/2013 Cioanta et al.
8,556,890 B2 10/2013 Wham
8,574,247 B2 11/2013 Adams et al.
8,632,461 B2 1/2014 Glossop
8,685,201 B2 4/2014 O'Rourke et al.
8,709,075 B2 4/2014 Adams et al.
8,728,091 B2 5/2014 Hakala et al.
8,747,416 B2 6/2014 Hakala et al.
8,790,359 B2 7/2014 Rabiner et al.
8,805,466 B2 8/2014 Salahieh et al.
8,888,788 B2 11/2014 Hakala et al.
8,897,869 B2 11/2014 Kassab
8,900,166 B2 12/2014 Spector
8,900,264 B2 12/2014 Drasler et al.
8,926,630 B2 1/2015 Diamant et al.
8,956,371 B2 2/2015 Hawkins et al.
8,956,374 B2 2/2015 Hawkins et al.
9,005,198 B2 4/2015 Long et al.
9,005,216 B2 4/2015 Hakala et al.
9,011,462 B2 4/2015 Adams et al.
9,011,463 B2 4/2015 Adams et al.
9,044,618 B2 6/2015 Hawkins et al.
9,044,619 B2 6/2015 Hawkins et al.
9,072,534 B2 7/2015 Adams et al.
9,119,624 B2 9/2015 Wham
9,138,249 B2 9/2015 Adams et al.
9,161,768 B2 10/2015 Cioanta et al.
9,180,280 B2 11/2015 Hawkins et al.
9,192,772 B1 11/2015 Tsukamoto et al.
9,198,825 B2 12/2015 Katragadda et al.
9,220,521 B2 12/2015 Hawkins et al.
9,277,955 B2 3/2016 Herscher et al.
9,289,258 B2 3/2016 Cohen
9,333,000 B2 5/2016 Hakala et al.
9,375,533 B2 6/2016 Ducharme et al.
9,421,025 B2 8/2016 Hawkins et al.
9,431,428 B2 8/2016 Yamazaki
9,433,428 B2 9/2016 Hakala et al.
9,504,807 B2 11/2016 Drasler et al.
9,522,012 B2 12/2016 Adams
9,579,114 B2 2/2017 Mantell et al.

(56) References Cited

U.S. PATENT DOCUMENTS 9,610,006 B2 4/2017 Salahieh et al.
9,636,124 B2 5/2017 Mantell
9,642,673 B2 5/2017 Adams et al.
9,717,513 B2 8/2017 Golan
9,730,715 B2 8/2017 Adams
9,743,980 B2 8/2017 Diamant et al.
9,757,194 B2 9/2017 Werneth et al.
9,763,624 B2 9/2017 Stanislaus et al.
9,808,167 B2 11/2017 Kassab
9,814,476 B2 11/2017 Adams et al.
9,833,373 B2 12/2017 Brouillette et al.
9,861,377 B2 1/2018 Mantell
9,867,629 B2 1/2018 Hawkins
9,913,594 B2 3/2018 Li et al.
9,974,607 B2 5/2018 Stone et al.
9,993,292 B2 6/2018 Adams et al.
10,010,666 B2 7/2018 Rubinsky et al.
10,039,561 B2 8/2018 Adams et al.
10,058,340 B2 8/2018 Cioanta et al.
10,118,015 B2 11/2018 De et al.
10,149,690 B2 12/2018 Hawkins et al.
10,154,799 B2 12/2018 Van et al.
10,159,505 B2 12/2018 Hakala et al.
10,194,930 B2 2/2019 Du
10,201,387 B2 2/2019 Grace et al.
10,206,698 B2 2/2019 Hakala et al.
10,219,720 B2 3/2019 Kassab
10,226,265 B2 3/2019 Ku et al.
10,238,405 B2 3/2019 Cioanta et al.
10,238,408 B2 3/2019 Zhong et al.
10,357,264 B2 7/2019 Kat-Kuoy
10,364,981 B2 7/2019 Wang et al.
10,426,500 B2 10/2019 Lipowski et al.
10,478,202 B2 11/2019 Adams et al.
10,500,128 B2 12/2019 Engles et al.
10,517,620 B2 12/2019 Adams
10,517,621 B1 12/2019 Hakala et al.
10,555,744 B2 2/2020 Nguyen et al.
10,603,058 B2 3/2020 Mantell
10,639,051 B2 5/2020 Cioanta et al.
10,646,240 B2 5/2020 Betelia et al.
10,661,034 B2 5/2020 Mantell et al.
10,668,208 B2 6/2020 Rubinsky et al.
10,682,178 B2 6/2020 Adams et al.
10,702,293 B2 7/2020 Adams et al.
10,709,462 B2 7/2020 Nguyen et al.
10,751,000 B2 8/2020 Hacker
10,756,440 B2 8/2020 Asagi et al.
10,765,440 B2 9/2020 Tozzi
10,786,267 B2 9/2020 Wasdyke et al.
10,806,504 B2 10/2020 Hubelbank
10,842,567 B2 11/2020 Grace et al.
10,849,637 B1 12/2020 Mantell
10,849,879 B2 12/2020 Seward
10,850,078 B2 12/2020 Grace et al.
10,856,893 B2 12/2020 Eggert et al.
10,888,373 B2 1/2021 Koblish et al.
10,893,903 B2 1/2021 Koblish et al.
10,898,213 B2 1/2021 Grace et al.
10,959,743 B2 3/2021 Adams et al.
10,966,737 B2 4/2021 Nguyen
10,973,538 B2 4/2021 Hakala et al.
11,000,299 B2 5/2021 Hawkins et al.
11,020,135 B1 6/2021 Hawkins
11,026,707 B2 6/2021 Ku et al.
11,058,492 B2 7/2021 Grace et al.
11,076,874 B2 8/2021 Hakala et al.
11,103,262 B2 8/2021 Tran et al.
11,160,467 B2 11/2021 Kassab et al.
11,179,169 B2 11/2021 Brouillette et al.
11,219,388 B2 1/2022 Kassab
11,246,659 B2 2/2022 Grace et al.
11,266,817 B2 3/2022 Cope et al.
11,296,509 B1 4/2022 Benavides
11,337,713 B2 5/2022 Nguyen et al.
11,432,834 B2 9/2022 Adams
11,478,261 B2 * 10/2022 Nguyen ................ A61B 17/22
11,484,327 B2 11/2022 Anderson et al.
11,534,187 B2 12/2022 Bonutti
11,559,318 B2 1/2023 Lipowski et al.
11,559,319 B2 1/2023 Mantell
11,583,339 B2 2/2023 Schultheis
11,596,424 B2 3/2023 Hakala et al.
11,602,363 B2 3/2023 Nguyen
11,617,618 B2 4/2023 Koblish et al.
11,622,780 B2 4/2023 Nguyen et al.
11,666,348 B2 6/2023 Cioanta et al.
11,672,554 B1 6/2023 Mantell
11,696,799 B2 7/2023 Adams et al.
11,771,449 B2 10/2023 Adams et al.
11,779,363 B2 10/2023 Vo
11,839,391 B2 12/2023 Schultheis et al.
11,857,212 B2 1/2024 Capelli et al.
11,911,056 B2 2/2024 Anderson et al.
11,925,366 B2 3/2024 Cioanta et al.
11,944,331 B2 4/2024 Anderson et al.
11,950,793 B2 4/2024 Nguyen
11,957,369 B2 4/2024 Batchelder et al.
11,996,649 B1 5/2024 Carpenter
12,004,759 B2 6/2024 Cioanta
12,004,760 B2 6/2024 Cioanta
12,005,210 B2 6/2024 Chisena et al.
12,016,610 B2 6/2024 Flores et al.
12,016,817 B2 6/2024 Engles et al.
12,035,932 B1 7/2024 Nunes et al.
12,048,445 B2 7/2024 Mantell
12,114,923 B2 * 10/2024 Adams ............... A61B 18/1492
12,156,668 B2 12/2024 Anderson et al.
12,178,458 B1 12/2024 Betelia et al.
12,214,147 B2 2/2025 Gianotti et al.
12,220,141 B2 2/2025 Ullmann
12,232,754 B2 2/2025 Nguyen
12,232,755 B2 2/2025 Phan et al.
12,239,332 B2 3/2025 Cioanta et al.
12,318,100 B2 6/2025 Cioanta
12,364,493 B2 7/2025 Cioanta et al.
12,364,494 B2 7/2025 Cioanta et al.
12,426,904 B2 9/2025 Nguyen et al.
12,426,938 B2 * 9/2025 Vo ..................... A61B 17/2202
12,433,619 B2 10/2025 Liu et al.
12,514,602 B2 1/2026 Schoenle
2001/0037106 A1 11/2001 Shadduck
2001/0044596 A1 11/2001 Jaafar
2002/0045890 A1 4/2002 Celliers et al.
2002/0072705 A1 6/2002 Vrba et al.
2002/0082553 A1 6/2002 Duchamp
2002/0103455 A1 8/2002 Zhang et al.
2002/0169458 A1 11/2002 Connors
2002/0177889 A1 11/2002 Brisken et al.
2002/0198521 A1 12/2002 Maguire
2003/0004434 A1 1/2003 Greco et al.
2003/0014047 A1 1/2003 Woloszko et al.
2003/0065371 A1 4/2003 Satake
2003/0135223 A1 7/2003 Teague et al.
2003/0144654 A1 7/2003 Hilal
2003/0176873 A1 9/2003 Chernenko et al.
2003/0191492 A1 10/2003 Gellman et al.
2003/0229370 A1 12/2003 Miller
2004/0006288 A1 1/2004 Spector et al.
2004/0006307 A1 1/2004 Qureshi et al.
2004/0006333 A1 1/2004 Arnold et al.
2004/0010249 A1 1/2004 Truckai et al.
2004/0024347 A1 2/2004 Wilson et al.
2004/0044308 A1 3/2004 Naimark et al.
2004/0054367 A1 3/2004 Jimenez et al.
2004/0073251 A1 4/2004 Weber
2004/0097963 A1 5/2004 Seddon
2004/0097996 A1 5/2004 Rabiner et al.
2004/0153109 A1 8/2004 Tiedtke et al.
2004/0162508 A1 8/2004 Uebelacker
2004/0167466 A1 8/2004 Drasler et al.
2004/0172110 A1 9/2004 Satake
2004/0193046 A1 9/2004 Nash et al.
2004/0215139 A1 10/2004 Cohen

(56) References Cited

U.S. PATENT DOCUMENTS

2004/0249401 A1 12/2004 Rabiner et al.
2004/0254570 A1 12/2004 Hadjicostis et al.
2005/0010140 A1 1/2005 Forssmann
2005/0015953 A1 1/2005 Keidar
2005/0021013 A1 1/2005 Visuri et al.
2005/0059965 A1 3/2005 Eberl et al.
2005/0075662 A1 4/2005 Pedersen et al.
2005/0090888 A1 4/2005 Hines et al.
2005/0096669 A1 5/2005 Rabiner et al.
2005/0113722 A1 5/2005 Schultheiss
2005/0113822 A1 5/2005 Fuimaono et al.
2005/0159645 A1 7/2005 Bertolero et al.
2005/0171527 A1 8/2005 Bhola
2005/0194583 A1 9/2005 Taylor et al.
2005/0197667 A1 9/2005 Chan et al.
2005/0228343 A1 10/2005 Kelley
2005/0228372 A1 10/2005 Truckai et al.
2005/0228428 A1 10/2005 Ali et al.
2005/0245866 A1 11/2005 Azizi
2005/0251131 A1 11/2005 Lesh
2005/0256410 A1 11/2005 Rabiner et al.
2005/0267467 A1 12/2005 Paul et al.
2005/0267488 A1 12/2005 Hare et al.
2005/0273130 A1 12/2005 Sell
2006/0004286 A1 1/2006 Chang et al.
2006/0041304 A1 2/2006 Jang et al.
2006/0064081 A1 3/2006 Rosinko
2006/0069424 A1 3/2006 Acosta et al.
2006/0074484 A1 4/2006 Huber
2006/0178685 A1 8/2006 Melsheimer
2006/0184076 A1 8/2006 Gill et al.
2006/0190022 A1 8/2006 Beyar et al.
2006/0200191 A1 9/2006 Zadno-Azizi
2006/0221528 A1 10/2006 Li et al.
2006/0235269 A1 10/2006 Waxman
2006/0241524 A1 10/2006 Lee et al.
2006/0282153 A1 12/2006 Jang
2007/0005053 A1 1/2007 Dando
2007/0016112 A1 1/2007 Schultheiss et al.
2007/0032723 A1 2/2007 Glossop
2007/0038227 A1 2/2007 Massicotte et al.
2007/0078500 A1 4/2007 Ryan et al.
2007/0088380 A1 4/2007 Hirszowicz et al.
2007/0106320 A1 5/2007 Blix et al.
2007/0123851 A1 5/2007 Alejandro et al.
2007/0129667 A1 6/2007 Tiedtke et al.
2007/0156129 A1 7/2007 Kovalcheck
2007/0198047 A1 8/2007 Schon et al.
2007/0201031 A1 8/2007 Axelrod et al.
2007/0225677 A1 9/2007 Rowe et al.
2007/0232964 A1 10/2007 Voss
2007/0239082 A1 10/2007 Schultheiss et al.
2007/0239182 A1 10/2007 Glines et al.
2007/0239253 A1 10/2007 Jagger et al.
2007/0244423 A1 10/2007 Zumeris et al.
2007/0250052 A1 10/2007 Wham
2007/0255270 A1 11/2007 Carney
2007/0270897 A1 11/2007 Skerven et al.
2007/0282301 A1 12/2007 Segalescu et al.
2007/0299392 A1 12/2007 Beyar et al.
2007/0299481 A1 12/2007 Syed et al.
2008/0027464 A1 1/2008 Moll et al.
2008/0039790 A1 2/2008 Hasebe
2008/0058836 A1 3/2008 Moll et al.
2008/0065013 A1 3/2008 Goodin
2008/0065014 A1 3/2008 Von et al.
2008/0097251 A1 4/2008 Babaev
2008/0183111 A1 7/2008 Voss
2008/0188803 A1 8/2008 Jang
2008/0188866 A1 8/2008 Karpiel et al.
2008/0188913 A1 8/2008 Stone et al.
2008/0200896 A1 8/2008 Shmulewitz et al.
2008/0249518 A1 10/2008 Warnking et al.
2008/0249595 A1 10/2008 McDaniel
2008/0300610 A1 12/2008 Chambers
2009/0036829 A1 2/2009 Pagel et al.
2009/0036831 A1 2/2009 Howat
2009/0041833 A1 2/2009 Bettinger et al.
2009/0054875 A1 2/2009 Strauss et al.
2009/0069748 A1 3/2009 Schaeffer
2009/0143651 A1 6/2009 Kallback et al.
2009/0157066 A1 6/2009 Satake
2009/0227992 A1 9/2009 Nir et al.
2009/0234282 A1 9/2009 McAndrew et al.
2009/0247945 A1 10/2009 Levit et al.
2009/0254114 A1 10/2009 Hirszowicz et al.
2009/0299447 A1 12/2009 Jensen et al.
2009/0312768 A1 12/2009 Hawkins et al.
2010/0016862 A1 1/2010 Hawkins et al.
2010/0036294 A1 2/2010 Mantell et al.
2010/0082059 A1 4/2010 Gellman et al.
2010/0094209 A1 4/2010 Drasler et al.
2010/0114020 A1 5/2010 Hawkins et al.
2010/0114065 A1 5/2010 Hawkins et al.
2010/0121322 A1 5/2010 Swanson
2010/0179424 A1 7/2010 Warnking et al.
2010/0228192 A1 9/2010 O'Dea et al.
2010/0229792 A1 9/2010 Yamasaki et al.
2010/0274271 A1 10/2010 Kelley
2010/0286709 A1 11/2010 Diamant et al.
2010/0305565 A1 12/2010 Truckai et al.
2011/0028868 A1 2/2011 Spector
2011/0033807 A1 2/2011 Wang et al.
2011/0034832 A1 2/2011 Cioanta et al.
2011/0064953 A1 3/2011 O'Rourke et al.
2011/0092957 A1 4/2011 Intoccia
2011/0118634 A1 5/2011 Golan
2011/0166570 A1 7/2011 Hawkins et al.
2011/0196412 A1 8/2011 Levit et al.
2011/0208185 A1 8/2011 Diamant et al.
2011/0257523 A1 10/2011 Hastings et al.
2011/0264039 A1 10/2011 Thielen et al.
2011/0270273 A1 11/2011 Moll et al.
2011/0295227 A1 12/2011 Hawkins et al.
2012/0071889 A1 3/2012 Mantell et al.
2012/0095461 A1 4/2012 Herscher et al.
2012/0116289 A1 5/2012 Hawkins et al.
2012/0143177 A1 6/2012 Avitall
2012/0157991 A1 6/2012 Christian
2012/0172696 A1 7/2012 Kaellbaeck et al.
2012/0203255 A1 8/2012 Hawkins et al.
2012/0221013 A1 8/2012 Hawkins et al.
2012/0253358 A1 10/2012 Golan
2013/0030431 A1 1/2013 Adams
2013/0030447 A1 1/2013 Adams
2013/0033968 A1 2/2013 Schaefer et al.
2013/0041355 A1 2/2013 Heeren et al.
2013/0096571 A1 4/2013 Massicotte et al.
2013/0116714 A1 5/2013 Adams et al.
2013/0123694 A1 5/2013 Subramaniyan et al.
2013/0150874 A1 6/2013 Kassab
2013/0253622 A1 9/2013 Hooven
2013/0345600 A1 12/2013 Katragadda et al.
2014/0005576 A1 1/2014 Adams et al.
2014/0039513 A1 2/2014 Hakala et al.
2014/0039514 A1 2/2014 Adams et al.
2014/0046229 A1 2/2014 Hawkins et al.
2014/0046353 A1 2/2014 Adams
2014/0052145 A1 2/2014 Adams et al.
2014/0052146 A1 2/2014 Curtis et al.
2014/0052147 A1 2/2014 Hakala et al.
2014/0074111 A1 3/2014 Hakala et al.
2014/0074113 A1 3/2014 Hakala et al.
2014/0163592 A1 6/2014 Hawkins et al.
2014/0180278 A1 6/2014 Abboud et al.
2014/0214061 A1 7/2014 Adams et al.
2014/0228803 A1 8/2014 Kogan
2014/0243820 A1 8/2014 Adams et al.
2014/0243846 A1 8/2014 Aggerholm et al.
2014/0243847 A1 8/2014 Hakala et al.
2014/0257323 A1 9/2014 Mantell
2014/0288570 A1 9/2014 Adams
2015/0039002 A1 2/2015 Hawkins
2015/0073430 A1 3/2015 Hakala et al.

(56) References Cited

U.S. PATENT DOCUMENTS

2015/0080995 A1 3/2015 Seeley et al.
2015/0094703 A1 4/2015 Zikorus et al.
2015/0238208 A1 8/2015 Adams et al.
2015/0238209 A1 8/2015 Hawkins et al.
2015/0251012 A1 9/2015 Olson
2015/0320432 A1 11/2015 Adams
2016/0022295 A1 1/2016 Mantell
2016/0095610 A1 4/2016 Lipowski et al.
2016/0101280 A1 4/2016 Thakkar et al.
2016/0113674 A1 4/2016 Kelley
2016/0135828 A1 5/2016 Hawkins et al.
2016/0141892 A1 5/2016 Li et al.
2016/0151081 A1 6/2016 Adams et al.
2016/0183957 A1 6/2016 Hakala et al.
2016/0184023 A1 6/2016 Grace et al.
2016/0324534 A1 11/2016 Hawkins et al.
2016/0331389 A1 11/2016 Hakala et al.
2016/0354144 A1 12/2016 Caplan et al.
2017/0000959 A1 1/2017 Mantell et al.
2017/0020598 A1 1/2017 Millis et al.
2017/0056035 A1 3/2017 Adams
2017/0086867 A1 3/2017 Adams
2017/0135709 A1 5/2017 Nguyen et al.
2017/0258523 A1 9/2017 Adams et al.
2017/0274160 A1 9/2017 Mantell et al.
2017/0303946 A1 10/2017 Ku et al.
2017/0311965 A1 11/2017 Adams
2018/0028208 A1 2/2018 Adams et al.
2018/0083477 A1 3/2018 Tian et al.
2018/0098779 A1 4/2018 Betelia et al.
2018/0153568 A1 6/2018 Kat-Kuoy
2018/0214166 A1 8/2018 Mantell
2018/0256250 A1 9/2018 Adams et al.
2018/0303501 A1 10/2018 Hawkins
2018/0304053 A1 10/2018 Eggert et al.
2018/0317946 A1 11/2018 Adams et al.
2018/0360482 A1 12/2018 Nguyen
2019/0000491 A1 1/2019 Schoenle
2019/0069916 A1 3/2019 Hawkins et al.
2019/0150960 A1 5/2019 Nguyen et al.
2019/0175198 A1 6/2019 Ku et al.
2019/0254607 A1 8/2019 Kllbck et al.
2019/0254692 A1 8/2019 Hakala et al.
2019/0262594 A1 8/2019 Ogata et al.
2019/0269426 A1 9/2019 Hakala et al.
2019/0365400 A1 12/2019 Adams et al.
2019/0388110 A1 12/2019 Nguyen et al.
2020/0000484 A1 1/2020 Hawkins
2020/0022716 A1 1/2020 Hakala et al.
2020/0038044 A1 2/2020 Lipowski et al.
2020/0085458 A1 3/2020 Nguyen et al.
2020/0085459 A1 3/2020 Adams
2020/0100803 A1 4/2020 Mantell
2020/0129195 A1 4/2020 McGowan et al.
2020/0129741 A1 4/2020 Kawwas et al.
2020/0129742 A1 4/2020 Cope et al.
2020/0246032 A1 8/2020 Betelia et al.
2020/0281505 A1 9/2020 Kassab et al.
2020/0289767 A1 9/2020 Mantell et al.
2020/0297280 A1 9/2020 Kllbck et al.
2020/0297366 A1 9/2020 Nguyen et al.
2020/0330143 A1* 10/2020 Walzman .......... A61B 17/2202
2020/0383724 A1 12/2020 Adams et al.
2020/0397453 A1 12/2020 McGowan et al.
2020/0398033 A1 12/2020 McGowan et al.
2020/0406010 A1 12/2020 Massimini et al.
2021/0038237 A1 2/2021 Adams
2021/0059751 A1 3/2021 Zhang et al.
2021/0085347 A1 3/2021 Phan et al.
2021/0085348 A1 3/2021 Nguyen
2021/0085349 A1 3/2021 Cioanta et al.
2021/0085350 A1 3/2021 Cioanta et al.
2021/0085383 A1 3/2021 Vo et al.
2021/0093342 A1 4/2021 Cioanta et al.
2021/0128241 A1* 5/2021 Schultheis ............ A61B 18/26
2021/0177445 A1 6/2021 Nguyen
2021/0186613 A1 6/2021 Cook et al.
2021/0220052 A1 7/2021 Cook
2021/0228137 A1 7/2021 Aujla
2021/0242817 A1 8/2021 Huang et al.
2021/0267615 A1 9/2021 Cioanta et al.
2021/0267685 A1 9/2021 Schultheis et al.
2021/0275247 A1 9/2021 Schultheis et al.
2021/0282792 A1 9/2021 Adams et al.
2021/0290259 A1* 9/2021 Hakala ............. A61B 17/22022
2021/0290305 A1 9/2021 Cook et al.
2021/0308001 A1 10/2021 Cioanta
2021/0310786 A1 10/2021 Zhang et al.
2021/0330384 A1 10/2021 Cook et al.
2021/0338258 A1 11/2021 Hawkins et al.
2021/0378743 A1 12/2021 Massimini et al.
2022/0008129 A1 1/2022 Hancock et al.
2022/0015785 A1 1/2022 Hakala et al.
2022/0054194 A1 2/2022 Bacher et al.
2022/0071692 A1 3/2022 Govari et al.
2022/0104875 A1 4/2022 Gleiman et al.
2022/0125453 A1 4/2022 Nguyen
2022/0152321 A1 5/2022 Haber et al.
2022/0183708 A1 6/2022 Phan et al.
2022/0240958 A1 8/2022 Nguyen et al.
2022/0273324 A1 9/2022 Schultheis
2022/0273916 A1 9/2022 Kawwas et al.
2022/0280765 A1 9/2022 Tabiliran et al.
2022/0287731 A1 9/2022 Tan et al.
2022/0287732 A1 9/2022 Anderson et al.
2022/0291442 A1 9/2022 De et al.
2022/0313359 A1 10/2022 Schultheis et al.
2022/0331012 A1 10/2022 Bumpus
2022/0338890 A1 10/2022 Anderson et al.
2022/0339428 A1 10/2022 Porterfield et al.
2022/0354578 A1* 11/2022 Cook .................. A61B 18/245
2022/0409160 A1* 12/2022 Buckler ................ G16C 20/30
2023/0028890 A1 1/2023 Cioanta
2023/0040190 A1 2/2023 Batchelder et al.
2023/0043475 A1 2/2023 Adams
2023/0044926 A1 2/2023 Batchelder et al.
2023/0064371 A1 3/2023 Cook et al.
2023/0107690 A1 4/2023 Nguyen
2023/0110647 A1 4/2023 Buscaglia et al.
2023/0111554 A1 4/2023 Cioanta
2023/0130458 A1* 4/2023 Walzman ....... A61B 17/320758
606/41
2023/0165598 A1 6/2023 Nguyen et al.
2023/0293195 A1 9/2023 Lipowski et al.
2023/0293196 A1 9/2023 Mantel
2023/0293197 A1 9/2023 Nguyen et al.
2023/0310054 A1 10/2023 Schultheis
2023/0310073 A1 10/2023 Adams et al.
2023/0329731 A1 10/2023 Hakala et al.
2023/0363774 A1 11/2023 Cioanta et al.
2023/0380849 A1 11/2023 Adams et al.
2023/0380903 A1* 11/2023 Chisena ................ A61B 18/26
2023/0381472 A1* 11/2023 Chisena .............. G06N 3/0464
2023/0389987 A1* 12/2023 Sun ....................... A61B 18/26
2023/0404605 A1 12/2023 Vo
2023/0414234 A1 12/2023 Anderson et al.
2024/0016508 A1 1/2024 Kocur
2024/0099734 A1 3/2024 Capelli et al.
2024/0156476 A1 5/2024 Staab et al.
2024/0156478 A1 5/2024 Ballard et al.
2024/0188973 A1 6/2024 Cioanta et al.
2024/0188975 A1 6/2024 Nguyen
2024/0189030 A1 6/2024 Cook et al.
2024/0189543 A1 6/2024 Salinas et al.
2024/0206896 A1 6/2024 Ingersoll et al.
2024/0206972 A1 6/2024 Sun et al.
2024/0216062 A1 7/2024 Cook et al.
2024/0252191 A1 8/2024 Cioanta et al.
2024/0252192 A1 8/2024 Anderson et al.
2024/0268842 A1 8/2024 Phan et al.
2024/0277374 A1 8/2024 Varilla et al.
2024/0277410 A1 8/2024 Cook
2024/0285295 A1 8/2024 Cioanta
2024/0285296 A1 8/2024 Vo

(56) References Cited

U.S. PATENT DOCUMENTS

| | | | |
|---|---|---|---|
| 2024/0293282 | A1 | 9/2024 | Engles et al. |
| 2024/0299051 | A1 | 9/2024 | Sidhu et al. |
| 2024/0335206 | A1 | 10/2024 | Liu et al. |
| 2024/0350154 | A1 | 10/2024 | Nunes et al. |
| 2024/0366245 | A1 | 11/2024 | Schoenle |
| 2024/0423654 | A1 | 12/2024 | Ji et al. |
| 2025/0000532 | A1 | 1/2025 | Jens |
| 2025/0064471 | A1 | 2/2025 | Hasenberg et al. |
| 2025/0072967 | A1 | 3/2025 | Hasenberg et al. |
| 2025/0160862 | A1 | 5/2025 | Betelia et al. |
| 2025/0169835 | A1 | 5/2025 | Kerlo et al. |
| 2025/0176984 | A1 | 6/2025 | Hasenberg et al. |
| 2025/0228578 | A1 | 7/2025 | Hakala et al. |
| 2025/0228579 | A1 | 7/2025 | Nguyen et al. |
| 2025/0268617 | A1 | 8/2025 | Rond et al. |
| 2025/0275782 | A1 | 9/2025 | Hasenberg et al. |
| 2025/0303109 | A1 | 10/2025 | Johnson et al. |
| 2026/0051747 | A1 | 2/2026 | Ding et al. |

FOREIGN PATENT DOCUMENTS

| | | | |
|---|---|---|---|
| AU | 2007254353 | A1 | 11/2007 |
| AU | 2009257368 | A1 | 12/2009 |
| AU | 2009313507 | B2 | 11/2014 |
| AU | 2013284490 | A1 | 1/2015 |
| AU | 2013315444 | B2 | 8/2017 |
| AU | 2018204691 | B2 | 6/2019 |
| CA | 2104414 | A1 | 2/1995 |
| CA | 2613360 | A1 | 1/2007 |
| CA | 2652381 | A1 | 11/2007 |
| CA | 2727429 | A1 | 12/2009 |
| CA | 2779600 | A1 | 5/2010 |
| CN | 1204242 | A | 1/1999 |
| CN | 1269708 | A | 10/2000 |
| CN | 1161081 | C | 8/2004 |
| CN | 1942145 | A | 4/2007 |
| CN | 101043914 | A | 9/2007 |
| CN | 101495023 | A | 7/2009 |
| CN | 201629723 | U | 11/2010 |
| CN | 102057422 | A | 5/2011 |
| CN | 102271748 | A | 12/2011 |
| CN | 102355856 | A | 2/2012 |
| CN | 102765785 | A | 11/2012 |
| CN | 203564304 | U | 4/2014 |
| CN | 107633840 | A | 1/2018 |
| CN | 208694015 | U | 4/2019 |
| CN | 109965922 | A | 7/2019 |
| CN | 209548049 | U | 10/2019 |
| CN | 209996422 | U | 1/2020 |
| CN | 110811761 | A | 2/2020 |
| CN | 111067591 | A | 4/2020 |
| CN | 111184553 | A | 5/2020 |
| CN | 211094481 | U | 7/2020 |
| CN | 211094508 | U | 7/2020 |
| CN | 111388086 | B | 8/2020 |
| CN | 111568500 | A | 8/2020 |
| CN | 111568539 | A | 8/2020 |
| CN | 111969882 | A | 11/2020 |
| CN | 212491104 | U | 2/2021 |
| CN | 112516439 | A | 3/2021 |
| CN | 112618922 | A | 4/2021 |
| CN | 112674838 | A | 4/2021 |
| CN | 112754645 | A | 5/2021 |
| CN | 112842460 | A | 5/2021 |
| CN | 112869825 | A | 6/2021 |
| CN | 112869826 | A | 6/2021 |
| CN | 112869827 | A | 6/2021 |
| CN | 112932609 | A | 6/2021 |
| CN | 113117220 | A | 7/2021 |
| CN | 113244506 | A | 8/2021 |
| CN | 113288335 | A | 8/2021 |
| CN | 113289212 | A | 8/2021 |
| CN | 113289216 | A | 8/2021 |
| CN | 306761244 | S | 8/2021 |
| CN | 113332568 | A | 9/2021 |
| CN | 113332569 | A | 9/2021 |
| CN | 113332570 | A | 9/2021 |
| CN | 113349882 | A | 9/2021 |
| CN | 113349982 | A | 9/2021 |
| CN | 113398444 | A | 9/2021 |
| CN | 113440215 | A | 9/2021 |
| CN | 113558715 | A | 10/2021 |
| CN | 113598878 | A | 11/2021 |
| CN | 113633347 | A | 11/2021 |
| CN | 113730768 | A | 12/2021 |
| CN | 113842190 | A | 12/2021 |
| CN | 113855153 | A | 12/2021 |
| CN | 215067917 | U | 12/2021 |
| CN | 215228131 | U | 12/2021 |
| CN | 215384399 | U | 1/2022 |
| CN | 215384400 | U | 1/2022 |
| CN | 215386905 | U | 1/2022 |
| CN | 215458400 | U | 1/2022 |
| CN | 215458401 | U | 1/2022 |
| CN | 215505065 | U | 1/2022 |
| CN | 215537694 | U | 1/2022 |
| CN | 215584286 | U | 1/2022 |
| CN | 215606068 | U | 1/2022 |
| CN | 215651394 | U | 1/2022 |
| CN | 215653328 | U | 1/2022 |
| CN | 215688241 | U | 2/2022 |
| CN | 215739273 | U | 2/2022 |
| CN | 215900676 | U | 2/2022 |
| CN | 114098896 | A | 3/2022 |
| CN | 114098897 | A | 3/2022 |
| CN | 114098898 | A | 3/2022 |
| CN | 114209960 | A | 3/2022 |
| CN | 215960130 | U | 3/2022 |
| CN | 216061635 | U | 3/2022 |
| CN | 216495498 | U | 5/2022 |
| CN | 307361122 | S | 5/2022 |
| CN | 217040236 | U | 7/2022 |
| CN | 217066519 | U | 7/2022 |
| CN | 307436397 | S | 7/2022 |
| CN | 112971914 | B | 8/2022 |
| CN | 114831697 | A | 8/2022 |
| CN | 217138101 | U | 8/2022 |
| CN | 217162846 | U | 8/2022 |
| CN | 115051691 | A | 9/2022 |
| CN | 115137444 | A | 10/2022 |
| CN | 115149929 | A | 10/2022 |
| CN | 115153753 | A | 10/2022 |
| CN | 115154852 | A | 10/2022 |
| CN | 115192872 | A | 10/2022 |
| CN | 217611283 | U | 10/2022 |
| CN | 115252050 | A | 11/2022 |
| CN | 115389852 | A | 11/2022 |
| CN | 115463317 | A | 12/2022 |
| CN | 218391846 | U | 1/2023 |
| CN | 115737062 | A | 3/2023 |
| CN | 218899599 | U | 4/2023 |
| CN | 115944355 | B | 6/2023 |
| CN | 116392203 | B | 9/2023 |
| CN | 117462207 | A | 1/2024 |
| DE | 2635635 | A1 | 2/1978 |
| DE | 3038445 | A1 | 5/1982 |
| DE | 3536073 | A1 | 4/1987 |
| DE | 3900433 | A1 | 7/1990 |
| DE | 3930600 | A1 | 4/1991 |
| DE | 4005743 | A1 | 8/1991 |
| DE | 4007295 | A1 | 9/1991 |
| DE | 4012642 | A1 | 10/1991 |
| DE | 4120259 | A1 | 12/1992 |
| DE | 29724174 | U1 | 4/2000 |
| DE | 10010467 | A1 | 9/2001 |
| DE | 102004053549 | A1 | 5/2006 |
| DE | 202006014285 | U1 | 12/2006 |
| DE | 102006002412 | A1 | 7/2007 |
| EP | 0249338 | A2 | 12/1987 |
| EP | 0311295 | A2 | 4/1989 |
| EP | 0313836 | A2 | 5/1989 |
| EP | 0351240 | A2 | 1/1990 |
| EP | 0382392 | A1 | 8/1990 |
| EP | 0442199 | A2 | 8/1991 |

(56) References Cited

FOREIGN PATENT DOCUMENTS

| | | | |
|---|---|---|---|
| EP | 0547146 | A1 | 6/1993 |
| EP | 0558297 | A2 | 9/1993 |
| EP | 0571306 | A1 | 11/1993 |
| EP | 0647435 | A1 | 4/1995 |
| EP | 0704226 | A1 | 4/1996 |
| EP | 0623360 | B1 | 3/1999 |
| EP | 1898775 | A2 | 3/2008 |
| EP | 2023796 | A2 | 2/2009 |
| EP | 2043501 | A2 | 4/2009 |
| EP | 2046227 | A2 | 4/2009 |
| EP | 1009303 | B1 | 6/2009 |
| EP | 2120736 | A1 | 11/2009 |
| EP | 2253884 | A1 | 11/2010 |
| EP | 2300091 | A2 | 3/2011 |
| EP | 2362798 | A2 | 9/2011 |
| EP | 2032201 | B1 | 4/2013 |
| EP | 2866689 | A1 | 5/2015 |
| EP | 2879607 | A1 | 6/2015 |
| EP | 2884911 | B1 | 6/2016 |
| EP | 3487414 | A2 | 5/2019 |
| EP | 3641672 | A1 | 4/2020 |
| EP | 2895086 | B1 | 5/2021 |
| EP | 4110213 | A1 | 1/2023 |
| EP | 4199849 | A1 | 6/2023 |
| EP | 3960099 | B1 | 8/2023 |
| EP | 4387540 | A1 | 6/2024 |
| EP | 4391946 | A1 | 7/2024 |
| EP | 4406496 | A1 | 7/2024 |
| EP | 4423863 | A1 | 9/2024 |
| EP | 4431032 | A1 | 9/2024 |
| FR | 2412301 | A1 | 7/1979 |
| FR | 2593382 | A1 | 7/1987 |
| FR | 2738381 | A1 | 3/1997 |
| JP | 58-032755 | A | 2/1983 |
| JP | 60-191353 | U | 12/1985 |
| JP | 61-146251 | A | 7/1986 |
| JP | 62-009921 | U | 1/1987 |
| JP | 62-060547 | A | 3/1987 |
| JP | 62-099210 | U | 6/1987 |
| JP | 62-275446 | A | 11/1987 |
| JP | 03-063059 | A | 3/1991 |
| JP | 06-070984 | A | 3/1994 |
| JP | 06-125915 | A | 5/1994 |
| JP | 07-047135 | A | 2/1995 |
| JP | 08-089511 | A | 4/1996 |
| JP | 10-099444 | A | 4/1998 |
| JP | 10-314177 | A | 12/1998 |
| JP | 10-513379 | A | 12/1998 |
| JP | 2002-538932 | A | 11/2002 |
| JP | 2003-102850 | A | 4/2003 |
| JP | 2004-081374 | A | 3/2004 |
| JP | 2004-223080 | A | 8/2004 |
| JP | 2004-357792 | A | 12/2004 |
| JP | 2005-501597 | A | 1/2005 |
| JP | 2005-095410 | A | 4/2005 |
| JP | 2005-515825 | A | 6/2005 |
| JP | 2006-516465 | A | 7/2006 |
| JP | 2007-054480 | A | 3/2007 |
| JP | 2007-289707 | A | 11/2007 |
| JP | 2007-532182 | A | 11/2007 |
| JP | 2008-506447 | A | 3/2008 |
| JP | 4072580 | B2 | 4/2008 |
| JP | 2009-537222 | A | 10/2009 |
| JP | 4491149 | B2 | 6/2010 |
| JP | 2011-513694 | A | 4/2011 |
| JP | 2011-520248 | A | 7/2011 |
| JP | 2011-524203 | A | 9/2011 |
| JP | 2011-528963 | A | 12/2011 |
| JP | 2012-505050 | A | 3/2012 |
| JP | 2012-508042 | A | 4/2012 |
| JP | 2014-208305 | A | 11/2014 |
| JP | 5636363 | B2 | 12/2014 |
| JP | 2015-525657 | A | 9/2015 |
| JP | 2015-528327 | A | 9/2015 |
| JP | 6029828 | B2 | 11/2016 |
| JP | 6081510 | B2 | 2/2017 |
| JP | 6104375 | B2 | 3/2017 |
| JP | 6257625 | B2 | 1/2018 |
| JP | 6278530 | B2 | 2/2018 |
| JP | 6364011 | B2 | 7/2018 |
| JP | 6529565 | B2 | 6/2019 |
| JP | 7142035 | B2 | 9/2022 |
| JP | 7277060 | B2 | 5/2023 |
| JP | 7364735 | B2 | 10/2023 |
| WO | 89/11307 | A1 | 11/1989 |
| WO | 91/10228 | A1 | 7/1991 |
| WO | 91/10403 | A1 | 7/1991 |
| WO | 92/03975 | A1 | 3/1992 |
| WO | 95/10232 | A1 | 4/1995 |
| WO | 96/24297 | A1 | 8/1996 |
| WO | 97/21460 | A1 | 6/1997 |
| WO | 98/33171 | A2 | 7/1998 |
| WO | 99/00060 | A1 | 1/1999 |
| WO | 99/02096 | A1 | 1/1999 |
| WO | 99/21611 | A1 | 5/1999 |
| WO | 00/33913 | A2 | 6/2000 |
| WO | 00/50115 | A2 | 8/2000 |
| WO | 00/51511 | A1 | 9/2000 |
| WO | 00/56237 | A2 | 9/2000 |
| WO | 01/24712 | A1 | 4/2001 |
| WO | 03/51450 | A1 | 6/2003 |
| WO | 03/86236 | A2 | 10/2003 |
| WO | 03/86525 | A1 | 10/2003 |
| WO | 2004/069072 | A2 | 8/2004 |
| WO | 2005/053532 | A1 | 6/2005 |
| WO | 2005/099594 | A1 | 10/2005 |
| WO | 2005/102199 | A1 | 11/2005 |
| WO | 2006/006169 | A2 | 1/2006 |
| WO | 2006/060492 | A2 | 6/2006 |
| WO | 2006/127158 | A2 | 11/2006 |
| WO | 2007/002079 | A2 | 1/2007 |
| WO | 2007/022055 | A1 | 2/2007 |
| WO | 2007/052341 | A1 | 5/2007 |
| WO | 2007/053967 | A1 | 5/2007 |
| WO | 2007/086965 | A2 | 8/2007 |
| WO | 2007/088546 | A2 | 8/2007 |
| WO | 2007/136599 | A2 | 11/2007 |
| WO | 2007/149905 | A2 | 12/2007 |
| WO | 2008/014425 | A2 | 1/2008 |
| WO | 2008/017080 | A2 | 2/2008 |
| WO | 2008/097833 | A1 | 8/2008 |
| WO | 2009/121017 | A1 | 10/2009 |
| WO | 2009/126544 | A1 | 10/2009 |
| WO | 2009/128061 | A2 | 10/2009 |
| WO | 2009/136268 | A2 | 11/2009 |
| WO | 2009/152352 | A2 | 12/2009 |
| WO | 2010/014515 | A2 | 2/2010 |
| WO | 2010/054048 | A2 | 5/2010 |
| WO | 2011/006017 | A1 | 1/2011 |
| WO | 2011/094111 | A2 | 8/2011 |
| WO | 2011/143468 | A3 | 3/2012 |
| WO | 2012/025833 | A2 | 3/2012 |
| WO | 2012/064404 | A1 | 5/2012 |
| WO | 2012/106259 | A2 | 8/2012 |
| WO | 2013/059735 | A1 | 4/2013 |
| WO | 2013/070750 | A1 | 5/2013 |
| WO | 2013/169807 | A1 | 11/2013 |
| WO | 2014/004887 | A1 | 1/2014 |
| WO | 2014/025397 | A1 | 2/2014 |
| WO | 2014/025620 | A1 | 2/2014 |
| WO | 2014/025981 | A1 | 2/2014 |
| WO | 2014/028885 | A1 | 2/2014 |
| WO | 2014/043400 | A1 | 3/2014 |
| WO | 2015/017499 | A1 | 2/2015 |
| WO | 2015/167360 | A1 | 11/2015 |
| WO | 2016/130713 | A1 | 8/2016 |
| WO | 2018/200865 | A1 | 11/2018 |
| WO | 2019/099218 | A1 | 5/2019 |
| WO | 2019/174625 | A1 | 9/2019 |
| WO | 2020/048274 | A1 | 3/2020 |
| WO | 2020/192146 | A1 | 10/2020 |
| WO | 2021/022849 | A1 | 2/2021 |
| WO | 2021/025624 | A1 | 2/2021 |
| WO | 2021/061294 | A1 | 4/2021 |

(56) References Cited

FOREIGN PATENT DOCUMENTS

| | | |
|---|---|---|
| WO | 2021/061451 A1 | 4/2021 |
| WO | 2021/061523 A1 | 4/2021 |
| WO | 2021/122491 A1 | 6/2021 |
| WO | 2022/055784 A1 | 3/2022 |
| WO | 2022/127506 A1 | 6/2022 |
| WO | 2022/127507 A1 | 6/2022 |
| WO | 2022/127509 A1 | 6/2022 |
| WO | 2022/166883 A1 | 8/2022 |
| WO | 2022/186783 A1 | 9/2022 |
| WO | 2022/217917 A1 | 10/2022 |
| WO | 2023/015047 A1 | 2/2023 |
| WO | 2023/015295 A1 | 2/2023 |
| WO | 2023/029191 A1 | 3/2023 |
| WO | 2023/083084 A1 | 5/2023 |
| WO | 2024/049814 A1 | 3/2024 |
| WO | 2024/081361 A1 | 4/2024 |
| WO | 2024/102896 A2 | 5/2024 |
| WO | 2024/107418 A1 | 5/2024 |
| WO | 2024/107470 A1 | 5/2024 |
| WO | 2024/138037 A2 | 6/2024 |
| WO | 2024/138212 A1 | 6/2024 |
| WO | 2024/206827 A2 | 10/2024 |
| WO | 2024/216050 A2 | 10/2024 |
| WO | 2025/054289 A1 | 3/2025 |

OTHER PUBLICATIONS

International Search Report and Written Opinion of International Application No. PCT/US2023/037234, mailed Mar. 12, 2024, 8 pp.

International Search Report and Written Opinion received for International Patent Application No. PCT/US2022/078216, mailed on Feb. 1, 2023, 6 pages.

International Search Report and Written Opinion, mailed Apr. 12, 2024 for PCT Application Serial No. PCT/US2023/079209, filed Nov. 9, 2023.

International Search Report and Written Opinion, mailed Feb. 22, 2024, for PCT Application Serial No. PCT/US23/73648, filed Sep. 7, 2023.

International Search Report and Written Opinion, mailed May 28, 2024, for PCT Application Serial No. PCT/US23/085868, filed Dec. 23, 2024.

International Search Report issued in PCT/US2022/74607, mailed Oct. 25, 2022.

Judgment, Final Written Decision Determining All Challenged Claims Unpatentable Denying Petitioner's Motion to Exclude Denying Patent Owner's Motion to Exclude, 35 U.S.C. Section 318(a); 37 C.F.R. Section 42.64, Paper 75, IPR2019-00409, in U.S. Pat. No. 8,728,091 B2, dated Jul. 8, 2020.

Judgment, Final Written Decision Determining All Challenged Claims Unpatentable Denying Petitioner's Motion to Exclude Denying Petitioner's Motion to Exclude Denying Patent Owner's Motion to Exclude 35 U.S.C. Section 318(a), 37 C.F.R. Section 42.64, Paper 70, IPR2019-00408, in U.S. Pat. No. 9,642,673 B2, Entered Jul. 20, 2020.

Judgment, Final Written Decision Determining Some Challenged Claims Unpatentable Denying Petitioner's Motion to Exclude 35 U.S.C. Section 318(a), 37 C.F.R. Section 42.64, Paper 75, IPR2019-00405, in U.S. Pat. No. 8,956,371 B2, dated Jul. 8, 2020.

Kaltenbach, "The long wire technique—a new technique for steerable balloon catheter dilatation of coronary artery stenoses", European Heart Journal, vol. 5, 1984, pp. 1004-1009.

Kereiakes et al., "Principles of Intravascular Lithotripsy for Calcific Plaque Modification", JACC: Cardiovascular Interventions, vol. 14, No. 12, Jun. 28, 2021, pp. 1275-1292.

Kodama et al. "Innovative technology for tissue disruption by explosive-induced shock waves", Ultrasound in Medicine & Biology vol. 24, No. 9, 1998, pp. 1459-1460.

Lee et al., "Intravascular Lithotripsy for Calcified Left Main Artery Disease", Journal of the Society for Cardiovascular Angiography and Interventions, vol. 2, 2023, pp. 1-6.

Lee. et al., "Intravascular steerable guidewire for fiberoptic laser-heated metal cautery cap in dissolution of human atherosclerotic coronary disease," American Heart Journal, vol. 110, Issue 6, 1985, pp. 1304-1306.

Levin. et al., "Percutaneous Transluminal Coronary Angioplasty with an Over-the-Wire System," Radiology, vol. 155, Issue 2, 1985, pp. 323-326.

Lingeman, J. E., et al., "Shock wave lithotripsy: Advances in technology and technique." Nature Reviews Urology, vol. 6, Dec. 2009, pp. 660-670.

Litvack. et al., "Percutaneous excimer laser coronary angioplasty: results in the first consecutive 3,000 patients," Journal of the American College of Cardiology, vol. 23, Issue 2, 1994, pp. 323-329.

Llewellyn-Jones, F., "The Mechanism of Electrode Erosion in Electrical Discharges: Physical Basis of the Low Erosion Rate of the Platinum Metals", Platinum Metals Review, vol. 7, Issue 2, Jan. 1963, pp. 58-65.

Loske, A. M. (2007). Shock Wave Physics for Urologists. Centro de Física Aplicada y Tecnología Avanzada, National Autonomous University of Mexico. ISBN 978-970-32-4377-8.

Lumsden. et al., "Endovascular Therapy Principles of Peripheral Interventions," Blackwell Futura, 2006, 310 pages.

Mariani., "Combined Electrohydraulic and Holmium:YAG Laser Ureteroscopic Nephrolithotripsy for 20 to 40 mm Renal Calculi," The Journal of urology, vol. 172, Issue 1, 2004, pp. 170-174.

McAuley. et al., "Advances in guidewire technology," The American Journal of Cardiology, vol. 53, Issue 12, 1984, pp. C94-C96.

Miller et al., "Electrohydraulic Nephrolithotripsy: a Preferable Alternative to Ultrasound?", British Journal of Urology, vol. 56, 1984, pp. 589-593.

Miller., "Endoscopic application of shock wave technology for the destruction of renal calculi" World Journal of Urology, vol. 3, 1985, pp. 36-40.

Mishra, A., et al., "RevaTen platelet-rich plasma improves cardiac function after myocardial injury.", Cardiovascular Revascularization Medicine, vol. 12, No. 3, 2011, pp. 158-163.

Mohiuddin et al., "General principles of endovascular therapy" in Endovascular Therapy: Principles of Peripheral Interventions, pp. 1-19 (2006).

Müller-Leisse. et al., "Effectiveness and safety of ultrasonic atherosclerotic plaque ablation: In vitro investigation," Cardiovascular and interventional radiology, vol. 16, 1993, pp. 303-307.

Neuzil, P., et al., "TCT-61 Optimized external focused ultrasound for renal sympathetic denervation—Wave II trial.", Journal of the American College of Cardiology, vol. 62, No. 18S1, 2013.

Nimgaonkar, A., et al., "Gastroenterology and biodesign: contributing to the future of our specialty.", Gastroenterology, vol. 144, No. 2, 2013, pp. 258-262.

Northgate Technologies, Northgate Autolith pulse generator in 2007, at the Wayback Machine, https://web.archive.org/web/20070704002225/http://www.northgate-tech.com:80/Products/stonemanagement.asp.

Ormiston, J. A., et al., "TCT-412 non-invasive renal denervation using externally delivered focused ultrasound: early experience using Doppler based imaging tracking and targeting for treatment.", Journal of the American College of Cardiology, vol. 64, No. 11, 2014.

Owens, C. A., "Ultrasound-Enhanced Thrombolysis: EKOS EndoWave Infusion Catheter System". Seminars in Interventional Radiology, vol. 25, No. 1, Mar. 2025, pp. 37-41.

Papatsoris et al., "Update on Intracorporeal Laser Lithotripsy", Minerva Medica, vol. 104, No. 1, 2013, pp. 55-60.

Park. et al., "Percutaneous Nephrolithotomy Technical Aspects," The Practical Guide to Medical and Surgical Management, 2007, pp. 621-638.

Partial File History for U.S. Appl. No. 63/154,603, filed Feb. 26, 2021.

Partial File History for U.S. Appl. No. 63/176,156, filed Apr. 16, 2021.

Partial File History for U.S. Appl. No. 63/193,469, filed May 26, 2021.

(56) References Cited

OTHER PUBLICATIONS

Partial File History for U.S. Appl. No. 63/169,091, filed Mar. 31, 2021.
Payne., "Charles Theodore Dotter: the father of intervention," Texas Heart Institute Journal, vol. 28, Issue 1, 2001, pp. 28-38.
Petition for Inter Partes Review of U.S. Pat. No. 8,728,091, filed Dec. 7, 2018.
Petition for Inter Partes Review of U.S. Pat. No. 8,956,371 Under 35 U.S.C. Section 312 and 37 C.F.R. Section 42.104, filed Dec. 7, 2018.
Petition for Inter Partes Review of U.S. Pat. No. 9,642,673 Under 35 U.S.C. Section 312 and 37 C.F.R. Section 42.104, filed Dec. 7, 2018.
Rassweiler et al. "Efficacy of in situ Extracorporeal Shock Wave Lithotripsy for Upper Ureteral Calculi" Uropean Urology, vol. 12 No. 6, 1986, pp. 377-386.
Rosenschein. et al., "Experimental Ultrasonic Angioplasty: Disruption of Atherosclerotic Plaques and Thrombi in Vitro and Arterial Recanalization in Vivo," Journal of the American College of Cardiology, vol. 15, Issue 3, 1990, pp. 711-717.
Salgaonkar, V. A. & Diederich, C. J., "Catheter-based ultrasound technology for image-guided thermal therapy: Current technology and applications." International Journal of Hyperthermia, vol. 31, No. 2, Mar. 2015, pp. 203-215.
Sasportas, L. S., et al., "Cost-effectiveness landscape analysis of treatments addressing xerostomia in patients receiving head and neck radiation therapy.", Oral surgery, oral medicine, oral pathology and oral radiology, vol. 116, No. 1, 2013, pp. e37-e51.
Scotland et al., "Stone Technology: Intracorporeal Lithotripters", World Journal of Urology, vol. 35, 2017, pp. 1347-1351.
Seshiah et al., "Novel Lithotripsy-Assisted Transcatheter Aortic Valve Replacement May Reduce Risk of Aortic Root Rupture", Journal of the Society for Cardiovascular Angiography and Interventions, vol. 2, 2023, pp. 1-4.
Shockwave C 2. "Coronary IVL System Step-by-Step Setup", Shockwave Medical, Inc., Exhibit 2163, Provided as part of case IPR2019-00405, U.S. Pat. No. 8,956,371.
Ali, Z. "The Sound Science Behind Shockwave IVL's Mechanism of Action", Transcatheter Cardiovascular Therapeutics, Peripheral IVL Speaker Deck, believed to be presented Oct. 29, 2024.
Baim., "Grossman's Cardiac Catheterization, Angiography, and Intervention," Seventh Edition, 2005, 6 pages.
Baim., "Percutaneous Balloon Angioplasty and General Coronary Intervention," Chapter 22, 2005, pp. 433-466.
Basavarajaiah, S. et al., "To evaluate the impact of dose dependency on calcium fractures from the shockwave balloon in calcified lesions" [PowerPoint Presentation], Transcatheter Cardiovascular Therapeutics Conference, San Francisco, CA, United States, Oct. 25-28, 2025.
Begun, Frank P., "Modes of Intracorporeal Lithotripsy: Ultrasound Versus Electrohydraulic Lithotripsy Versus Laser Lithotripsy", Seminars in Urology, vol. 12, No. 1, Feb. 1994, pp. 39-50.
Bertrand et al., "Percutaneous Transluminal Coronary Rotary Ablation with Rotablator (European Experience)", The American Journal of Cardiology, vol. 69, Feb. 15, 1992, pp. 470-474.
Briggs, C., et al., "The New Shockwave L6 Peripheral Intravascular Lithotripsy (IVL) Catheter", Endovascular Today, May 2023.
Brinton, T. D., et al., "Abstract 12272: Ultrasound Mediated Renal Sympathetic Denervation", Circulation, vol. 124, No. 21, Nov. 22, 2011.
Brinton, T. J., et al., "Current use of imaging in cardiac stem cell clinical trials.", Current Cardiovascular Imaging Reports, vol. 2, No. 1, 2009, pp. 1-2.
Brinton, T. J., et al., "Outcomes from a postgraduate biomedical technology innovation training program: the first 12 years of Stanford Biodesign.", Annals of biomedical engineering, vol. 41, 2013, pp. 1803-1810.
Chan et al., "A Perspective on Laser Lithotripsy: The Fragmentation Processes", Journal of Endourology, vol. 15, No. 3, Apr. 2001, pp. 257-273.
Choi. et al., "Low Power Ultrasound Delivered Through a PTCA-Like Guidewire: Preclinical Feasibility and Safety of a Novel Technology for Intracoronary Thrombolysis," Journal of Interventional Cardiology, vol. 19, Issue 1, 2006, pp. 87-92.
Cleveland, R.O.; McAteer, J.A. "Physics of Shock-Wave Lithotripsy". In Smith's Textbook of Endourology; Wiley: Hoboken, NJ, USA, 2012; pp. 317-332.
Compare Materials, from MatWeb, retrieved from https://www.matweb.com, accessed on Feb. 26, 2024, 5 pp.
Corl, J. D., et al., "First Human Use of Shockwave L6 Intravascular Lithotripsy Catheter in Severely Calcified Large Vessel Stenoses", Journal of the Society for Cardiovascular Angiography & Interventions, vol. 2, Issue 4, May 2023.
Dash R., et al., "Abstract 12435: Detection of Injured Border Zone Myocardium Using Manganese-Enhanced and Delayed-Enhanced MRI in a Pig Ischemia-Reperfusion Model", Circulation, vol. 122, Supp. 21, Nov. 23, 2010.
Dash, R., et al., "Dual manganese-enhanced and delayed gadolinium-enhanced MRI detects myocardial border zone injury in a pig ischemia-reperfusion model.", Circulation: Cardiovascular Imaging, vol. 4, No. 5, 2011, pp. 574-582.
Davies, R., "You Asked; Shockwave C2 Aero Delivered: Shockwave's Next Coronary Catheter" [PowerPoint Presentation], Transcatheter Cardiovascular Therapeutics Conference, San Francisco, CA, United States, Oct. 25-28, 2025.
Dervan et al., "Transluminal angioplasty of occluded coronary arteries: use of a movable guide wire system", Circulation 68, No. 4, 1983, pp. 776-784.
Ernst. et al., "Ability of High-Intensity Ultrasound to Ablate Human Atherosclerotic Plaques and Minimize Debris Size," The American journal of cardiology, vol. 68, Issue 2, 1991, pp. 242-246.
Extended European Search Report dated Jul. 22, 2022 in European Patent Application No. 22168972.2.
Extended European Search Report dated Jul. 25, 2022 in European Patent Application No. 22167795.8.
Extended European Search Report dated Jul. 25, 2022 in European Patent Application No. 22167806.3.
Extended European Search Report dated Jul. 15, 2022 in European Patent Application No. 22167569.7.
Extended European Search Report dated Jul. 19, 2022 in European Patent Application No. 22168990.4.
Extended European Search Report dated Jul. 22, 2022 in European Patent Application No. 22169681.8.
Extended European Search Report dated Jul. 25, 2022 in European Patent Application No. 22167815.4.
Extended European Search Report dated Jul. 25, 2022 in European Patent Application No. 22168984.7.
Fuh, E., et al., "Bone marrow stem cells for the treatment of ischemic heart disease: a clinical trial review.", Journal of Cardiovascular Translational Research, vol. 2, 2009, pp. 202-218.
Gavin. et al., "An acoustic fluid-structure simulation of a therapeutic ultrasound wire waveguide apparatus," 11th International Conference on Computational Biogengineering, 2005, 14 pages.
Gerdesmeyer. et al., "Physical and technical basics of extracorporeal shock wave therapy (ESWT)," The orthopedist, vol. 7, Issue 31, 2002, pp. 610-617. (English abstract).
Gravenstein D., "Extracorporeal shock wave lithotripsy and percutaneous nephrolithotomy", Anesthesia and Renal Considerations, vol. 18, No. 4, Dec. 2000, pp. 953-971.
Grech., "Percutaneous coronary intervention. I: History and development," Bmj, vol. 326, Issue 7398, 2003, pp. 1080-1082.
Grocela et al., "Intracorporeal Lithotripsy: Instrumentation and Development", Urologic Clinics of North America, vol. 24, No. 1, Feb. 1997, pp. 13-23.
Gunn. et al., "New developments in percutaneous coronary intervention," BMJ, vol. 327, Issue 7407, 2003, pp. 150-153.
Harston et al., "Safety and Success of the Beginning Percutaneous Transluminal Coronary Angioplasty Program Using the Steerable Guidewire System", Coronary Angioplasty With Steerable Guidewire, vol. 57, Apr. 1, 1986, pp. 717-720.
Hong, S. J., et al., "Intracoronary and retrograde coronary venous myocardial delivery of adipose-derived stem cells in swine infarction lead to transient myocardial trapping with predominant pul-

(56) References Cited

OTHER PUBLICATIONS monary redistribution.", Catheterization and Cardiovascular Interventions, vol. 83, No. 1, 2014, pp. E17-E25.
International Application No. PCT/US2024/022239, filed Mar. 29, 2014.
International Application No. PCT/US2024/024296, filed Apr. 12, 2024.
International Application No. PCT/US2024/025362, filed Apr. 19, 2024.
International Application No. PCT/US2024/025369, filed Apr. 19, 2024.
International Preliminary Report on Patentability for dated Aug. 11, 2022 for PCT Application Serial No. PCT/US2022/071341, Filed Mar. 25, 2022.
International Preliminary Report on Patentability mailed Feb. 6, 2024 for PCT Application Serial No. PCT/US2022/074607, Filed Aug. 5, 2022.
International Search Report and Written Opinion issued in PCT application No. PCT/US2022/71341, dated Aug. 11, 2022.
International Search Report and Written Opinion issued in PCT/US2021/71726, dated Feb. 7, 2022.
International Search Report and Written Opinion of International Application No. PCT/US2023/85515, mailed Jun. 13, 2024, 10 pp.
International Search Report and Written Opinion of International Application No. PCT/US2024/022239, mailed Jul. 26, 2024, 8 pp.
International Search Report and Written Opinion of International Application No. PCT/US2024/024296, mailed Aug. 21, 2024, 14 pp.
International Search Report and Written Opinion of International Application No. PCT/US2024/025362, mailed Jul. 23, 2024, 12 pp.
International Search Report and Written Opinion of International Application No. PCT/US2024/025369, mailed Jul. 23, 2024, 11 pp.
The Wayback Machine accessed Feb. 27, 2026 for Feb. 24, 2021. Yoganand Velayutham "Leakage Current in Medical Devices" https://talema.com/leakage-current-in-medical-devices/.
Shockwave Medical Inc., "Shockwave Intravascular Lithotripsy (IVL) System with the Shockwave L6 Peripheral Intravascular Lithotripsy (IVL) Catheter—Instructions for use (IFU)", PN 67214-A, 2022, 6 pages.
Shockwave Medical Inc., "Shockwave Intravascular Lithotripsy (IVL) System with the Shockwave L6 Peripheral Intravascular Lithotripsy (IVL) Catheter—Instructions for use (IFU)", PN 69653-B, 2024, 5 pages.
Shockwave Medical, Investor Presentation, Slides 7-23 (Nov. 2022).
Siegel et al., "Ultrasonic plaque ablation. A new method for recanalization of partially or totally occluded arteries", Circulation, vol. 78, No. 6, Dec. 1988, pp. 1443-1448.
Sista, A. K., et al., "Applying a structured innovation process to interventional radiology: a single-center experience.", Journal of Vascular and Interventional Radiology, vol. 23, No. 4, 2012, 488-494.
Sokolov, D. L., et al., "Dual Pulse Lithotripsy Points Toward Faster, Safer Treatment for Kidney Stones", Dec. 2002, retrieved from https://acoustics.org/pressroom/httpdocs/144th/Bailey.htm, accessed on Dec. 9, 2025, 3 pages.
Sokolov, D. L., et al., "Dual-pulse lithotripter accelerates stone comminution and reduces cell injury in vitro", The Journal of the Acoustical Society of America. vol. 112, Issue 5, Nov. 2002, pp. 2290. Retrieved from https://pubs.aip.org/asa/jasa/article/112/5_Supplement/2290/541200/Dual-pulse-lithotripter-accelerates-stone, accessed Dec. 10, 2025.
Sokolov, D. L., et al., "Dual-pulse lithotripter accelerates stone fragmentation and reduces cell lysis in vitro", Ultrasound in Medicine & Biology, vol. 29, Issue 7, Jul. 2003, pp. 1045-1052.
Spratt, J.C., "Shockwave IVL Mechanism of Action" [PowerPoint Presentation], Transcatheter Cardiovascular Therapeutics Conference, San Francisco, CA, United States, Oct. 25-28, 2025.
Stoller et al., "Urinary Stone Disease: The Practical Guide to Medical and Surgical Management", 2007, 685 Pages.
Svendsen et al., "Conductance sizing balloon for measurement of peripheral artery minimal stent area," Journal of Vascular Surgery, vol. 60, No. 3, Sep. 2014, pp. 759-766.
Touya, G., et al., "Development of subsonic electrical discharges in water and measurements of the associated pressure waves", Journal of Physics D: Applied Physics, 39 (2006), pp. 5236-5244.
U.S. Appl. No. 61/289,125, filed Dec. 22, 2009.
Vorreuther et al., "Impact of Shock Wave Pattern and Cavitation Bubble Size on Tissue Damage During Ureteroscopic Electrohydraulic Lithotripsy", The Journal of Urology, vol. 153, Mar. 1995, pp. 849-853.
Vorreuther, R., et al., "Impact of voltage and capacity on the electrical and acoustic output of intracorporeal electrohydraulic lithotripsy", Urological Research, vol. 20, Sep. 1992, pp. 355-359.
Wang, Q., et al., "Effectiveness and safety of a novel IVL system for severe coronary calcification: The CALCI-CRACK trial", Canadian Journal of Cardiology, vol. 40, Issue 9, Sep. 2024, pp. 1657-1667.
Welch et al. "Laser Physics and Laser-Tissue Interaction", The Texas Heart Institute Journal, vol. 16 No. 3, 1989, pp. 141-149.
Willmann, J. K., et al., "Imaging gene expression in human mesenchymal stem cells: from small to large animals.", Radiology, vol. 252, No. 1, 2009, pp. 117-127.
Worley. et al., "Electrohydraulic Shock Wave Decalcification of Stenotic Aortic Valves : Postmortem and Intraoperative Studies" Journal of the American College of Cardiology, vol. 12, Issue 2, 1988, pp. 458-462.
Yock, P. G., et al., "Teaching biomedical technology innovation as a discipline.", Science translational medicine, vol. 3, No. 92, 2011, 5 pages.
Zheng et al., "Intracorporeal Lithotripsy: Update on Technology", Urologic Clinics of North America, vol. 27, No. 2, May 2000, pp. 301-313.
Zhong et al., "Transient Oscillation of Cavitation Bubbles Near Stone Surface During Electrohydraulic Lithotripsy," Journal of Endourology, vol. 11, No. 1, pp. 55-61 (Feb. 1997).
Galougahi, K.K., et. al., "Intravascular Lithotripsy in Cardiovascular Interventions", American College of Cardiology, Jul. 2020.
Li, G., et. al., "Evaluation of an experimental electrohydraulic discharge device for extracorporeal shock wave lithotripsy: Pressure field of sparker array", The Journal of the Acoustical Society of America, vol. 142, Issue 5, Nov. 2017, pp. 3147-3153.

* cited by examiner

FIG. 12

CONTROL OF IVL SYSTEMS, DEVICES AND METHODS THEREOF

CROSS-REFERENCE TO RELATED APPLICATIONS

This application is a continuation in part of application Ser. No. 19/170,999, filed Apr. 4, 2025, entitled "CONTROL OF IVL SYSTEMS, DEVICES AND METHODS THEREOF", which is a continuation of PCT/US2023/079209, filed Nov. 9, 2023, entitled "CONTROL OF IVL SYSTEMS, DEVICES AND METHODS THEREOF", which claims benefit of provisional application No. 63/424,573, filed Nov. 11, 2022, entitled "DEVICES, SYSTEMS, AND METHODS OF INTRAVASCULAR LITHOTRIPSY", and provisional application No. 63/580,547, filed Sep. 5, 2023, entitled "DEVICES, SYSTEMS AND METHODS OF INTRAVASCULAR LITHOTRIPSY" and provisional application No. 63/874,995, filed Sep. 3, 2025, entitled "HIGH-VOLTAGE/LOW-VOLTAGE ISOLATION IN IVL DEVICES", the entire contents of each of which is incorporated herein by reference.

BACKGROUND

Intravascular lithotripsy (IVL) is an advanced medical procedure utilizing high-energy pulses to break apart calcified plaque within blood vessels, restoring vessel patency and improving patient outcomes. The IVL console acts as the control and power center for these pulses, traditionally requiring a reliable energy source to generate the high voltages used in therapy.

Historically, directly connecting a console to a hospital's mains power supply presented significant risks for both patients and clinical operators. Medical devices that interface with a patient's body—especially those delivering high-voltage pulses—can be vulnerable to electrical hazards if isolation between the mains supply and patient-contacting circuitry is insufficient. Failure to achieve robust isolation may result in leakage currents, which—even at very low levels—can unintentionally stimulate patient tissue, causing discomfort, injury, or even adverse physiological effects such as arrhythmias. Likewise, compromised isolation puts operators at risk of exposure to hazardous voltages, potentially leading to electric shock, equipment damage, or interruption of critical interventions.

Due to the complexity and limitations of achieving complete electrical isolation when using mains power, most IVL consoles are now designed to operate solely on battery power. This approach effectively eliminates the problems associated with direct connection to external power sources, dramatically reducing the risk of leakage currents or accidental voltage exposures for both patients and clinicians. By relying on battery operation, the system avoids the technical hurdles and safety concerns that arise from isolation barriers, simplifying compliance with regulatory standards such as IEC 60601, and fostering a safer clinical environment.

Even with battery power systems need to maintain separation between the low-voltage control circuitry (which handles operator inputs and logic) and the high-voltage power circuitry (responsible for generating therapeutic pulses). Robust isolation within the console architecture is used to prevent high voltages from reaching user interfaces or external equipment, ensuring consistent safety for all involved.

In summary, current ILV systems implement battery-only operation to address the risks of electrical hazards, streamline device architecture, and deliver enhanced protection for both patients and healthcare professionals during intravascular lithotripsy procedures. However, this battery-only approach results in limitations on the time and amount of therapy that can be delivered by an IVL console.

The subject matter claimed herein is not limited to embodiments that solve any disadvantages or that operate only in environments such as those described above. Rather, this background is only provided to illustrate one exemplary technology area where some embodiments described herein may be practiced.

BRIEF DESCRIPTION OF THE SEVERAL VIEWS OF THE DRAWINGS

These drawings are exemplary illustrations of certain embodiments and, as such, are not intended to limit the disclosure.

FIG. 12 illustrates a graphic comparison of average peak pressure generated over 80 voltage pulses by a known IVL device and over a predetermined maximum number of voltage pulses by embodiments of IVL devices according to the present disclosure.

DETAILED DESCRIPTION OF THE INVENTION

Figure 1:
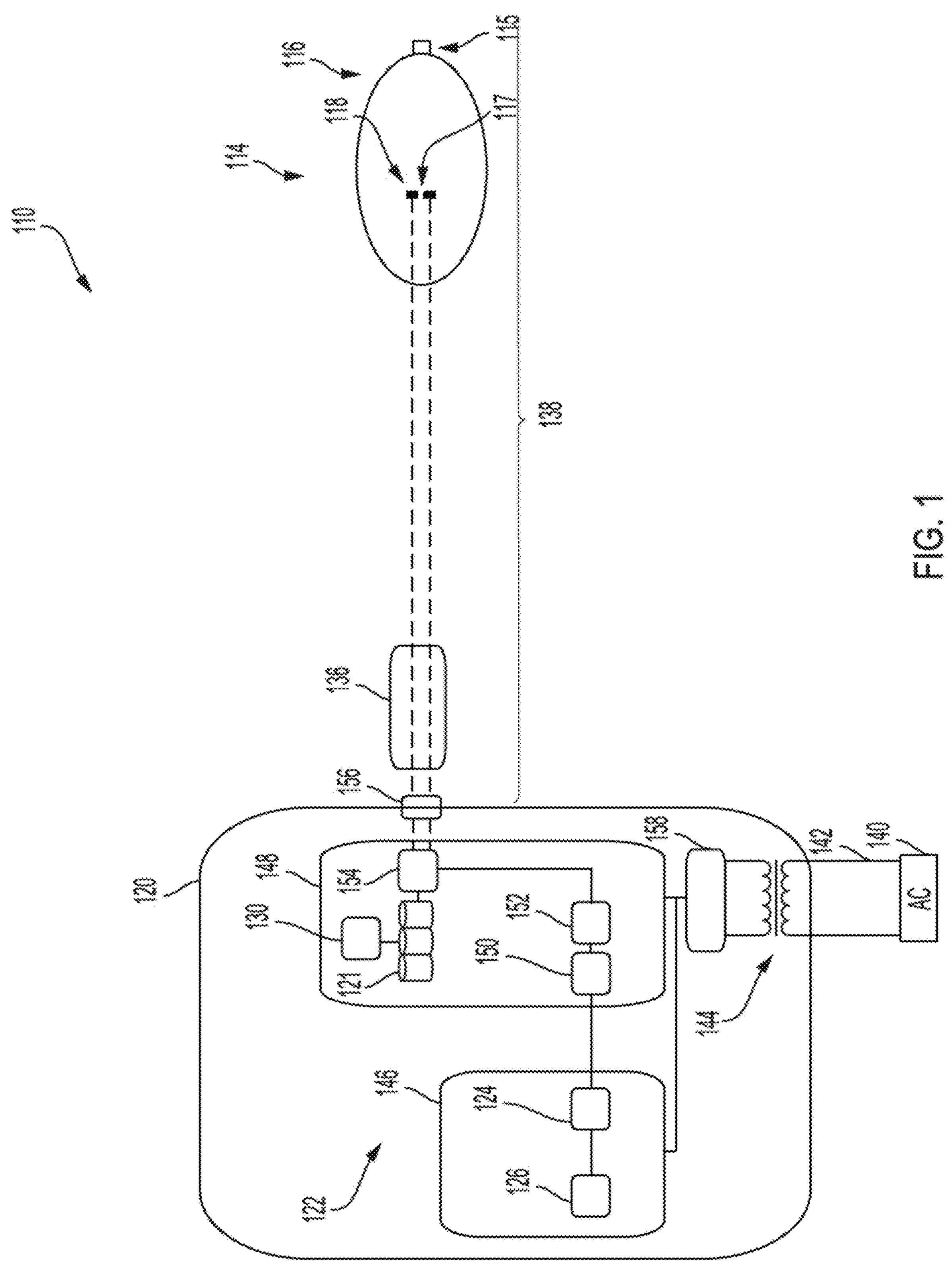
FIG. 1 illustrates a diagrammatic intravascular lithotripsy (IVL) arrangement according to one or more embodiments of the present disclosure.

The present disclosure pertains to an improved intravascular lithotripsy ("IVL") console, specifically directed to systems and methods for electrically isolating patient-contacting medical equipment from hazardous voltages while enabling reliable operation from a mains power source. To address risks of electrical leakage currents and compromised isolation between patient-facing and/or operator-facing components and external energy supplies—the present disclosure introduces a console architecture that incorporates layered isolation barriers to ensure optimal safety and performance.

The disclosed IVL console comprises a power plug configured for direct coupling to a mains power source, with one or more conductors extending from the plug to the console's internal circuitry. A first isolation barrier is positioned to electrically isolate incoming power from sensitive console components according to a predetermined dielectric strength. For example, this isolation may be part of a transformer or other power supply isolation. This isolation is configured to have a certain predetermined voltage dielectric strength. This barrier mitigates electrical hazards by preventing leakage currents and/or high-voltage to low-voltage circuit breakdown and protecting both patients and clinical operators during therapeutic delivery.

Within a console enclosure, the console is further divided into low-voltage control circuitry and high-voltage power circuitry. The high-voltage circuitry serves to generate pulses for intravascular therapy, while the low-voltage control section governs user input and operational commands. A second isolation barrier is provided between these two domains. The second isolation barrier couples a first processor (within the control circuitry) to a second processor (within the high-voltage circuitry). This configuration ensures that control commands are safely relayed without direct electrical connection, leveraging magnetic or optical coupling methods to achieve robust isolation.

The dual-barrier approach as described herein enables the IVL console to maintain a secure connection to mains power, supplying necessary energy to all functional units even during delivery of high-voltage therapeutic pulses to emitters in an associated catheter. The console architecture is further adaptable to embodiments involving expandable balloons with multiple electrodes for spark generation, expanding the versatility and clinical utility of the system.

By implementing these enhanced isolation strategies, embodiments address the limitations of battery-only designs, paving the way for longer, uninterrupted therapy sessions without compromising safety. Further, embodiments may facilitate the ability to perform more consecutive procedure sessions with different patients without delaying to recharge the console. The following detailed description elaborates upon the technical aspects and operational modes of various embodiments.

Traditional intravascular lithotripsy (IVL) devices, systems, and methods can apply high-energy electrical power to generate a spark (arc) between discharge electrodes. Under appropriate conditions, sparks generated by submerged electrodes can generate pressure waves within the medium, which can be applied to treat (breakup) calcified lesions within the patient's vasculature. It can be appreciated that appropriate control of such high-energy systems can be paramount to effective treatment, including safe treatment.

Intravascular lithotripsy systems, devices and methods have been described by Applicant. See PCT/2022/074607, filed Aug. 5, 2022 and entitled "INTRAVASCULAR LITHOTRIPSY BALLOON SYSTEMS, DEVICES AND METHODS", the entire contents of which are hereby incorporated by reference.

As illustrated in FIG. 1, a diagrammatic or schematic layout of portions of an exemplary IVL system 110 is provided. The illustrative IVL system 110 comprises a voltage pulse generator console 120 and a catheter assembly 114. Generally, the voltage pulse generator console 120 provides high-voltage pulses to the catheter assembly 114 to perform IVL therapy.

The catheter assembly 114 includes an elongate body, embodied as a catheter having guidewire 115, and a fluid-filled member 116 configured to contain conductive fluid therein, exemplified by an inflatable balloon, disposed near the distal end of the elongate body and arranged to receive fluid for inflation to facilitate IVL therapy. A set of dischargeable spaced-apart electrodes 118 are shown arranged within the exemplary fluid-filled member 116, at least some of which are spaced-apart by a gap 117 from each other to facilitate creation of a spark or electrical arc between the set of spaced-apart electrodes 118.

The IVL system embodiments described herein may be used in connection with electrodes that are within a fluid-filled member 116 configured to contain a fluid, e.g., a conductive fluid, therein. The fluid-filled member 116 embodiments may include an inflatable balloon or enclosure as shown in FIG. 1, which may be compliant or non-compliant and serves to contain the fluid such that the spaced-apart electrodes 118 are preferably fully submerged within the contained fluid. In addition, the fluid-filled member 116 may comprise a fillable member that is at least partially rigid and/or not flexible. In other embodiments, the fluid-filled member 116 may contain the fluid therein, and wherein the set of spaced-apart electrodes 118 is fully submerged within the contained fluid during the generation of an electrical arc between the spaced-apart electrodes during an IVL procedure.

Alternatively, the IVL system control embodiments of the present disclosure may be used in connection with electrodes that are not located or surrounded by a fluid-filled or fillable member 116. In these embodiments, the IVL system may comprise one or more sets of spaced-apart electrodes 118 that may be continuously or periodically exposed to saline or other fluid, and during the exposure, the IVL system may generate an electrical arc between the spaced-apart electrodes 118.

Each of the spaced-apart electrodes in FIG. 1 is arranged in communication (as suggested by dashed line conductors) with an electric pulse generation system, or voltage pulse generator console 120 to receive high-voltage electrical energy for spark generation to create pressure waves for IVL therapy. In the example illustrated, the catheter assembly 114 is coupled to the voltage pulse generator console 120 through a connector 156 which allows for selectively coupling the catheter assembly to the voltage pulse generator console 120. In the illustrative embodiment, one electrode may be grounded and the other provided with high-voltage from the voltage pulse generator console 120, although in some embodiments, any voltage differential may be applied. The voltage pulse generator console 120 may include an IVL control system 122 which includes high-voltage power circuitry 148 and other circuitry to control delivery of high-voltage pulses from the high-voltage power circuitry 148.

In the example illustrated, the voltage pulse generator console 120 is powered by a power plug 140 being coupled to mains power via conductors 142 external to the voltage pulse generator console 120. Power is supplied from the mains power through a first isolation barrier 144, that in this example is implemented as a transformer. Power is provided from the first isolation barrier 144 to a battery 158. The battery 158 provides power to the low-voltage control circuitry 146 and the high-voltage power circuitry 148. The first isolation barrier 144 isolates the mains power from the patient and operator as power supplied to the patient is supplied from the high-voltage power circuitry 148 and power used by the operator is supplied from the low-voltage control circuitry 146 and high-voltage power circuitry 148. For example, the first isolation barrier 144 may isolate circuitry, operators, and/or patients against an AC power source fault.

In an alternative embodiment, a power path controller is used where if mains power is connected, the input power splits to charge the battery and power the system. The system input becomes a logical OR of mains AC/DC or battery rather than always using the battery (which may or may not be charging at the same time). This embodiment can be useful in cases where the battery malfunctions and/or if the system utilizes a removable/exchangeable battery pack. In this case, if the system is plugged into mains power, the system will continue to operate whether the battery is installed or not.

Typically, the high-voltage power circuitry 148 is implemented on a circuit board that is separate from the low-voltage control circuitry 146 that will be discussed in more detail below. The high-voltage power circuitry 148 includes a capacitor bank 121 coupled to the catheter assembly 114 through a switch 154. The switch may be implemented using a reed relay, a high power IGBT, spark gap switch, combinations thereof or other high power switching component(s). The switch 154 is controllable to deliver a high-voltage pulse to the spaced-apart electrodes 118 from energy stored on the capacitor bank 121 or other high-voltage source.

The IVL control system 122 further includes low-voltage control circuitry 146. The low-voltage control circuitry 146, as noted above, is typically implemented on a different circuit board than the high-voltage power circuitry 148. In particular, this may be part of an isolation configuration to isolate the low-voltage control circuitry 146 from the high-voltage power circuitry 148. The low-voltage control circuitry 146 comprises a first processor 124 configured for executing instructions stored on memory 126 to provide communications signals through a second isolation barrier 150 to a second processor 152 in the high-voltage power circuitry 148 for IVL operations according to the first processor governance. In some embodiments, the first processor comprises part number MK50DN512CLL10 and the second processor comprises part number MKL81Z128VMC7 both available from NXP USA Inc. of Austin, TX. In some embodiments, the second isolation barrier 150 may include electronic and/or magnetic isolators. Magnetic isolators may use, for example, inductive devices and/or transformers. For example, in some embodiments, the isolation barrier may include a magnetic signal digital isolator such as part number ADUM4401 available from Analog Devices of Wilmington, Massachusetts. In an alternative or additional embodiment, the isolation barrier may include an optical digital signal isolator. This isolation scheme can isolate high voltages from the low-voltage control circuitry 146 thus providing protection to a device operator from the high voltages.

In an illustrative example, the first processor 124 can execute instructions stored on the memory 126 according to a designed pulse sequence or individual pulse. Note that the memory 126 may be part of the first processor 124 or implemented separately from the first processor 124. The first processor 124 can provide signal instructions to the second processor 152 through the isolation barrier 150. The second processor 152 then executes instructions at the second processor 152 [stored on memory of the second processor 152 and/or in external memory (not shown)] to cause the switch 154 to deliver voltage pulses from energy stored on the capacitor bank 121 to the spaced-apart electrodes 118.

Figure 2:
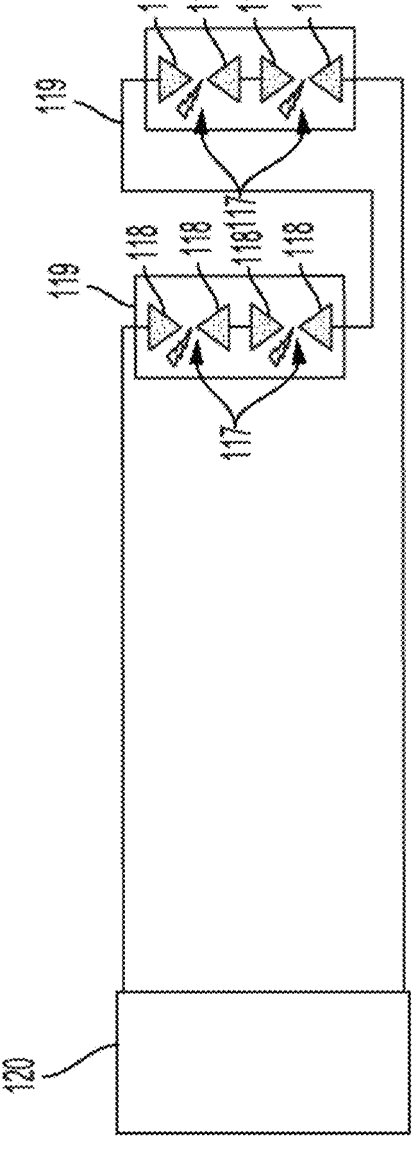
FIG. 2 illustrates two emitters defined within a support body.

An exemplary IVL system is shown in FIG. 2, illustrating one method for applying voltage pulses to the system, resulting in current flow through the exemplary system to each set of spaced-apart electrodes 118, where each set of spaced-apart electrodes 118 forms a spark gap 117. In the illustrated example, two sets of spaced-apart electrodes form an emitter 119. A given emitter 119 may include two spark gaps so as to accomplish more complete energy coverage, such as when the spark gaps are located on conductive bands around a catheter lumen to allow for pressure waves in multiple directions. Note that in other embodiments, emitters may include a single spark gap or more than two spark gaps. The emitters 119, and thus the four sets of spaced-apart electrodes (and thus spark gaps 117) are connected in series. FIG. 2 illustrates two emitters 119 defined within a support body. Application of a voltage pulse of sufficient magnitude and/or duration from the voltage pulse generator console 120 to the sets of serially connected spark gaps 117 will result in a production of electrical arcs as follows: a first arc across a first spark gap; a second arc across a second spark gap, a third arc across a third spark gap and a fourth arc across a fourth spark gap.

Appropriate control of such high-energy systems can also require achieving sufficient energy at the discharge site to create an electrical arc across the one or more spark gaps of an IVL system. Embodiments of the IVL systems, devices and methods described within the present disclosure may include operation for adjusting the total electrical energy provided to the system at each emitter. Such control systems for intravascular lithotripsy systems, devices and methods have been described by Applicant. See PCT/2023/079209, filed by Applicant on Nov. 9, 2023 and entitled "CONTROL OF IVL SYSTEMS, DEVICES AND METHODS THEREOF"; U.S. Ser. No. 18/290,173, filed by Applicant on Nov. 10, 2023 and entitled "CONTROL OF IVL SYSTEMS, DEVICES AND METHODS THEREOF"; U.S. Ser. No. 18/506,339, filed by Applicant on Nov. 10, 2023 and entitled "CONTROL OF IVL SYSTEMS, DEVICES AND METHODS THEREOF"; U.S. Ser. No. 18/506,416, filed by Applicant on Nov. 10, 2023 and entitled "CONTROL OF IVL SYSTEMS, DEVICES AND METHODS THEREOF"; and U.S. Ser. No. 18/506,428, filed by Applicant on Nov. 10, 2023 and entitled "CONTROL OF IVL SYSTEMS, DEVICES AND METHODS THEREOF", the entire contents of which are hereby incorporated by reference. The voltage pulse may be generated by discharging energy stored in the voltage pulse generator console 120, and in particular, in some embodiments, discharging energy stored in the voltage pulse generator console 120, including potentially the capacitor bank 121 (FIG. 1) which may produce an electrical arc across a spark gap between two spaced-apart electrodes. In some embodiments, the voltage pulses may be generated in one or more series of voltage pulses, wherein each adjacent series of voltage pulses may be spaced-apart or separated by time or other mechanism.

Figure 3:
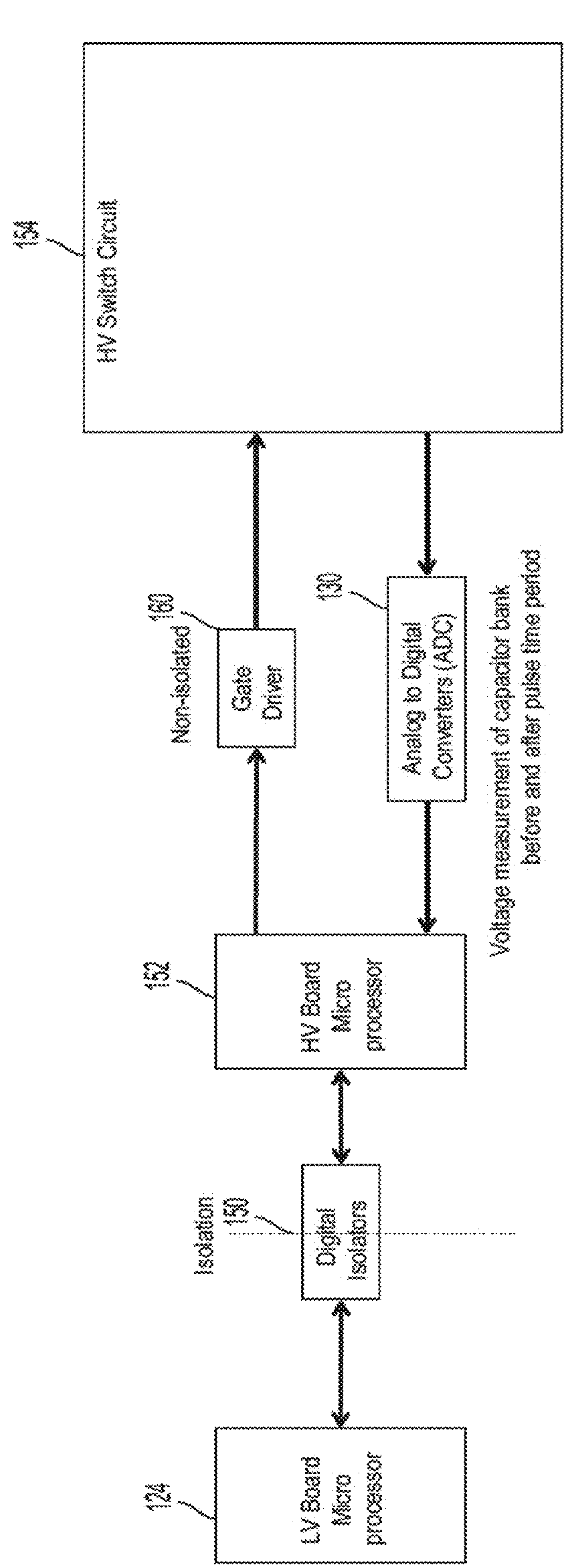
FIG. 3 illustrates additional details with respect to low-voltage and high-voltage isolation in the voltage pulse generator console.

FIG. 3 illustrates additional details with respect to low-voltage and high-voltage isolation in the voltage pulse generator console 120. As illustrated previously, the first processor 124 communicates instructions to the second processor 152 through the second isolation barrier 150. Note that in some embodiments, the first processor 124 may send an executable instruction comprising commands and arguments to the second processor 152. Alternatively, the first processor 124 may send a data packet to the second processor 152. In yet another example, the first processor 124 may simply send a single bit or multibit flag to the second processor 152. In one particular example, the second isolation barrier 150 includes a digital isolator as described previously. Such devices may include, for example, complementary high-voltage and low-voltage circuits implementing a clock input, a chip select input, a serial peripheral interface (SPI) input and an SPI output. In this case, typically data and/or instructions would be provided across the second isolation barrier 150 using such a device.

The second processor 152, in response to communication from the first processor 124 performs programmed actions to produce outputs for controlling the switch 154. In some embodiments, this may include determining to close the switch 154 to provide a high-voltage pulse from the capacitor bank 121 to a set of spaced-apart electrodes 118 to produce a spark. In some embodiments, this may be accomplished by driving an output pin on the second processor 152 high (or low depending on whether positive or negative logic is used) to drive a gate driver 160 to provide sufficient power to close the switch 154.

Note that while a single output pin from the second processor 152, a single gate driver 160, and a single switch 154 are shown, it should be appreciated that in other embodiments, a plurality of one or more of each of these may be present so as to drive emitter circuits independently from one another. In particular, if a plurality of spark gaps 117 and/or emitter 119 are implemented in a catheter assembly 114, at least some of these can be controlled independently of others by using different output pins, gate drivers, and relays. For example, in one embodiment, one or more common gate drivers are used, but are used in conjunction with a plurality of one or more reed relay sets and a plurality of output pins to allow for driving different emitters or sets of spaced-apart electrodes. Thus, the voltage pulse generator console 120 may be in operative and electrical association with one or more sets of spaced-apart electrodes 118. As illustrated, in some embodiments, such as that illustrated in FIG. 2, the various spaced-apart electrodes are connected in a serial electrical connection with the voltage pulse generator console 120 operatively and/or electrically connected with a more proximally located emitter 119. Alternative connection associations between the set(s) of spaced-apart electrodes 118 or emitter(s) 119 and the voltage pulse generator console 120 may be provided in alternative embodiments. For example, the two sets of spaced-apart electrodes may be connected in a parallel arrangement. Further, the voltage pulse generator console 120 may be operatively and/or electrically associated with a more distal spaced-apart set of electrodes 118 or emitter 119. Further different sets of electrodes 118 and/or different emitters 119 may be controlled independently.

FIG. 3 further illustrates a monitor 130 that may monitor voltages and/or currents. In some embodiments, the monitor is coupled directly to the capacitor bank 121 as shown in FIG. 1, while in other embodiments the monitor 130 is coupled to other components, such as the switch 154 to monitor voltages and/or currents delivered to emitters and/or residual voltages on the capacitor bank 121 after a spark has been delivered. In still other alternative embodiments, the monitor 130 may be located external to the voltage pulse generator console 120. The second processor 152 is in operative and/or electrical association with a monitor 130. The second processor 152 can provide information about voltages and/or currents monitored by the monitor 130 through the second isolation barrier 150 to the first processor 124, where such information can be used for reporting, spark control, or other purposes. In some embodiments, the monitor 130 may be located in a separate location apart from the voltage pulse generator console 120.

The system's architecture is designed to ensure both safety and operational efficiency. Redundant isolation strategies, including both physical and electrical barriers, are integrated to defend against possible faults or cross-domain interference. Various sections of circuitry—whether low or high voltage—are physically partitioned within an enclosure, minimizing (by shielding) electromagnetic interference and preventing accidental contact with hazardous voltages.

Embodiments may include a display mechanism, such as an LCD or LED panel, configured to provide real-time feedback on system status, operating parameters, and error notifications for enhanced procedural safety. Some embodiments may include one or more status indicators, such as visual LEDs or audible alerts, to signify operational states-including readiness, pulse delivery, fault, or standby-thereby facilitating intuitive user interaction.

The following discussion now refers to a number of methods and method acts that may be performed. Although the method acts may be discussed in a certain order or illustrated in a flow chart as occurring in a particular order, no particular ordering is required unless specifically stated, or required because an act is dependent on another act being completed prior to the act being performed.

Figure 4:
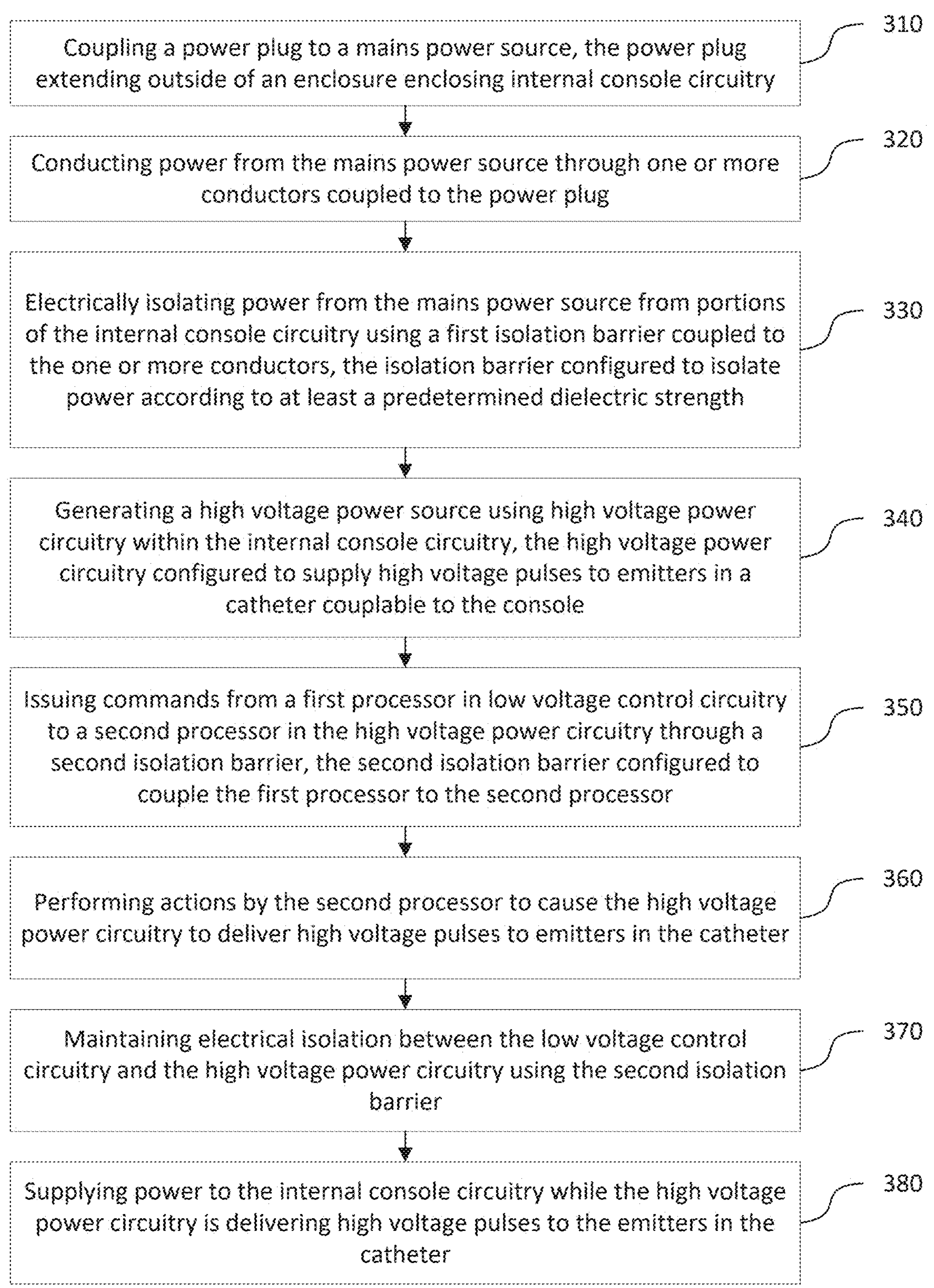
FIG. 4 is a flowchart of an example method for operating an intravascular lithotripsy (IVL) console.

FIG. 4 is a flowchart of an example method operating an intravascular lithotripsy (IVL) console.

At step 310, the method includes coupling a power plug to a mains power source, the power plug extending outside of an enclosure enclosing internal console circuitry.

At step 320, the method includes conducting power from the mains power source through one or more conductors coupled to the power plug.

At step 330, the method includes electrically isolating power from the mains power source from portions of the internal console circuitry using a first isolation barrier coupled to the one or more conductors, the isolation barrier configured to isolate power according to at least a predetermined dielectric strength.

At step 340, the method includes generating a high-voltage power source using high-voltage power circuitry within the internal console circuitry, the high-voltage power circuitry configured to supply high-voltage pulses to emitters in a catheter couplable to the console]

At step 350, the method includes issuing commands from a first processor in low-voltage control circuitry to a second processor in the high-voltage power circuitry through a second isolation barrier, the second isolation barrier configured to couple the first processor to the second processor.

At step 360, the method includes performing actions by the second processor to cause the high-voltage power circuitry to deliver high voltage pulses to emitters in the catheter.

At step 370, the method includes maintaining electrical isolation between the low-voltage control circuitry and the high-voltage power circuitry using the second isolation barrier.

At step 380, the method includes supplying power to the internal console circuitry while the high-voltage power circuitry is delivering high voltage pulses to the emitters in the catheter.

Further, the methods may be practiced by a computer system including one or more processors and computer-readable media such as computer memory. In particular, the computer memory may store computer-executable instructions that when executed by one or more processors cause various functions to be performed, such as the acts recited in the embodiments.

Figure 5:
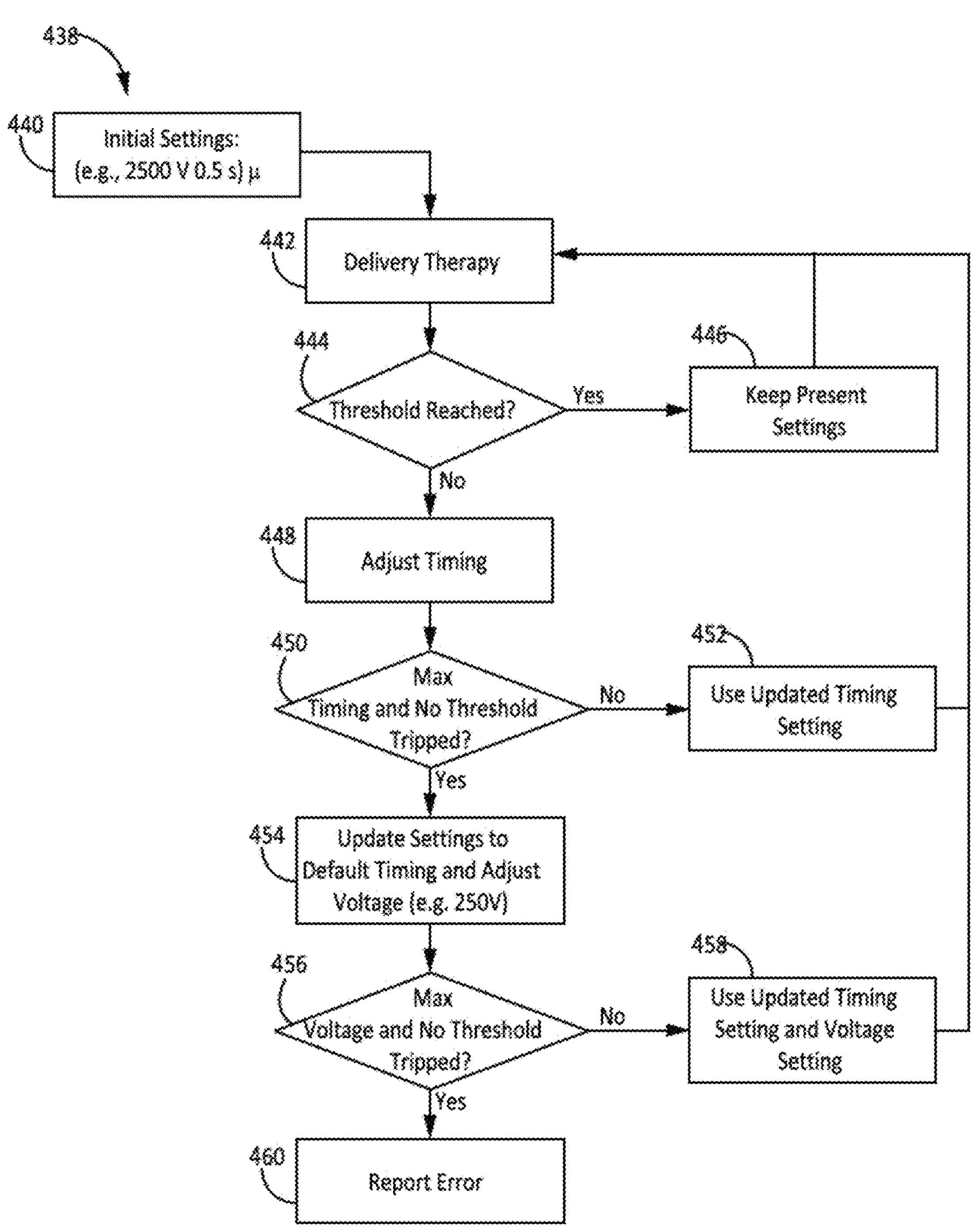
FIG. 5 illustrates a control operation flow diagram applicable to the IVL arrangement of FIG. 1 according to one or more embodiments of the present disclosure.

Referring now to FIG. 5, a flow diagram is shown concerning one embodiment of a control 438 in operation of IVL as discussed concerning boxes 440 through 460. Such control operations can be governed by the electric pulse generation system 20, and illustratively by the IVL control system 122 (see FIG. 6A). As discussed in additional detail herein, control 438 applies incremental changes in power parameters during cycling of applied voltage while monitoring parameters related to spark generation. For example, incrementally increasing the duration of voltage applied to the discharge electrodes can increase the likelihood of generation of an effective spark without excessive energy.

Moreover, if increases to the duration of voltage applied to the discharge electrodes fails to generate sufficient spark, incremental increase to the voltage can further increase the likelihood of generation of an effective spark without excessive power. Still further, if incrementally increased voltage fails to generate sufficient spark, duration can once again be incrementally increased before further increasing voltage. Accordingly, it can be appreciated that controlled incremental increases in duration and voltage can be implemented to achieve effective spark generation, and thus pressure wave generation, at or near the lowest required power characteristics for effective spark generation. Increasing the likelihood of reaching sufficient spark with lower power can increase the efficiency, safety, and/or reduce intensity of effective IVL therapy.

In box 440, initial settings are applied. For illustrative example, default initial settings are applied as a discharge voltage of 2500 volts (V) for a duration of 0.5 microseconds. In some embodiments, the initial settings may be determined by any suitable manner, including by use of programmable defaults, as adjusted settings based on use, for example, adjusted based on the patient characteristics, environmental conditions, procedural approach, and/or product cycle lifetime (i.e., operable age), among other aspects. From box 440, control may proceed to box 442.

In box 442, electrical energy is applied to the electrodes to deliver IVL therapy. In the first instance of proceeding from box 440 to box 442, electrical energy is applied at the initial settings, e.g., an applied voltage of 2500 V for a duration of 0.5 microseconds. When applied in a clinical setting, such that the IVL catheter is arranged within the patient's body lumen, and specifically with discharge electrodes submerged within a fluid medium within a fluid-filled member such as an angioplasty balloon, pressure wave therapy can ensue. However, as mentioned below, at present conditions, in some instances the energy provided at the initial settings may be insufficient to generate a spark at the electrodes, or may generate insufficient spark or insufficient pressure wave. From box 442, control may proceed to box 444.

In box 444, determination of threshold aspects is conducted. In the illustrative embodiment, a determined value for current applied in box 442 is compared with threshold current value. In the illustrative example, the threshold current value is embodied as a predetermined fixed value, e.g., 20 amperes (amps), but in some embodiments, may have any suitable value, for example 50 amps, 100 amps, 150 amps, 175 amps, the threshold current value for a given cycle may be determined based on the number of previous cycles in a therapy session, the number of cycles maintaining present settings (e.g., through box 446) in a therapy session, the number of particular successive cycles (e.g., number of successive cycles through box 446 or box 448 or box 452 or box 454 or box 458), the patient characteristics, environmental conditions, procedural approach, and/or product cycle lifetime (i.e., operable age), among other aspects. Additionally, although the threshold current value may be set to one value, the actual current passed during a sufficient generation of arc across the electrodes may be greater.

Responsive to determination that the determined value for current applied in box 442 is equal to or greater than the threshold current value, control may proceed to box 446. Otherwise, responsive to determination that the determined value for current applied in box 442 less than the threshold current value, control may proceed to box 448. For example, as mentioned above, insufficient spark generation may result in little or no current flow (e.g., about 0 to about 5 amps, which may represent dissipated energy into the medium without arcing) across the electrodes, which would not achieve the threshold current value, and thus would proceed to box 448.

In the illustrative embodiment, the determined current value for current applied in box 442 is embodied as the instantaneous current applied across the electrodes. In some embodiments, the determined current value may be embodied as an aggregated value, such as a time-averaged value of current applied to the electrodes. Continuing from the exemplary embodiment applying a threshold current value of 20 amps, when 20 amps is achieved by the therapy delivered, the spark generation is deemed sufficient.

It can be appreciated that the substantial occurrence of 20 amps provides considerable current across the discharge electrodes indicating the generation of meaningful spark. By comparison little or no current may flow across the discharge electrode when a spark fails to generate or when insufficient spark is generated under the applied duration and at the applicable voltage, 2500 V by example, and which can generally range between about 500 V to about 5000 V for IVL therapy, although conceivably can range between about 100 V to about 10000 V in terms of practical application.

In box 446, determination is made to maintain presently selected settings. In the illustrative embodiment, the presently selected settings include the discharge voltage of and applicable duration as applied immediately previously in box 442. For avoidance of doubt, if the initial settings have just immediately been applied in box 442, resulting in 20 amps of current, the initial settings would be applied in the next cycle of therapy. However, if the presently selected settings include updates settings, for example, updated duration and/or voltage settings from later portions of control 438, as discussed in additional detail herein, then maintaining presently selected settings would include the immediately applied updated settings. Maintaining presently selected settings proceeds openly to return to box 442, to again apply electrical energy to the electrodes to deliver IVL therapy.

In box 448, determination is made to increase the duration of applied voltage to the discharge electrodes. Continuing the example in which less than 20 amps of current indicates insufficient spark generation, rather than immediately increasing the voltage applied, the duration of applied voltage can be incrementally increased. At the microsecond-scale, increasing the duration of applied voltage can increase the likelihood of sufficient spark generation using the same voltage previously applied. This can be achieved as the result of overcoming threshold system impendence and/or other factors affecting the ease of spark generation during a given cycle at a given voltage.

The duration of applied voltage is increased by a predetermined duration interval, illustratively embodied as a fixed value, e.g., 0.5 microseconds. In some embodiments, the predetermined interval for given cycle may be determined based on factors such as the number of times therapy cycles have ensued previously during the therapy session (e.g., number of cycle intervals have proceeding through boxes 442, 444, 446, prior to proceeding to box 448), the patient characteristics, environmental conditions, procedural approach, and/or product cycle lifetime (i.e., operable age), among other aspects. In some embodiments, the predetermined duration interval for a given cycle may be varied by predetermined rate of change, for example, by percentage gain or loss by cycle. Control proceeds openly from box 448 to box 450.

In box 450, determination is made whether maximum duration has been achieved. In the illustrative embodiment, the maximum duration is a predetermined duration embodied as a fixed value, e.g., 6 microseconds. By way of example, if the control sequence progresses through cycles from initial settings of box 440 at 0.5 microseconds through box 448, until reaching 6 microseconds, the maximum duration would be achieved as a threshold value.

In some embodiments, the maximum duration for a given cycle may be determined based on the number of previous cycles in a therapy session, the number of cycles maintaining present settings (e.g., through box 446) in a therapy session, the number of particular successive cycles (e.g., number of successive cycles through box 446 or box 448 or box 452 or box 454 or box 458), the patient characteristics, environmental conditions, procedural approach, and/or product cycle lifetime (i.e., operable age), among other aspects. By deduction, in box 450, the threshold current value has not been achieved in the present cycle, although in some embodiments, affirmative determination and/or confirmation that threshold current value has not been achieved may be performed. Responsive to determination that the maximum duration has not been achieved, control proceeds to box 452. Otherwise, responsive to determination that maximum duration has been achieved, control proceeds to box 454.

In box 452, determination is made to apply the updated duration. In the illustrative embodiment, the duration has been updated in box 448 by increasing the presently selected duration by the predetermined duration interval, and determination to apply the updated duration confirms and proceeds with the updated duration. In the illustrative embodiment, the applied voltage remains as presently selected. Proceeding with the updated duration proceeds openly to return to box 442, to again apply electrical energy to the discharge electrodes to delivery therapy using the updated duration.

In box 454, the applied voltage is increased by a predetermined voltage interval. The presently selected setting for applied voltage is illustratively increased by the predetermined voltage interval. The presently selected duration is returned to the value at the initial setting, exampled as 0.5 microseconds, to be applied with the updated voltage, although in some embodiments, the updated duration may have any suitable value under newly updated voltage settings, for example, the updated duration may be determined based on the number of cycles of the therapy session when newly update voltages occur.

In the illustrative embodiment, the predetermined voltage interval is embodied as a fixed value of 250 V, such that, in the first exemplary occurrence of box 454, the presently selected applied voltage is increased to 2750 V from the value at the initial setting of 2500 V. In some embodiments, the predetermined voltage interval for a given cycle may be determined based on the number of previous cycles in a therapy session, the number of cycles maintaining present settings (e.g., through box 446) in a therapy session, the number of particular successive cycles (e.g., number of successive cycles through box 446 or box 448 or box 452 or box 454 or box 458), the patient characteristics, environmental conditions, procedural approach, and/or product cycle lifetime (i.e., operable age), among other aspects.

In box 456, a determination is made whether the maximum voltage has been achieved. In the illustrative embodiment, the maximum voltage is a predetermined voltage embodied as a fixed value, e.g., 3500 V. By way of example, if the control sequence progressed through cycles from initial settings of box 440 at 2500 V through box 454, until reaching 3500 V, the maximum voltage would be achieved as a threshold value.

In some embodiments, the maximum voltage for a given cycle may be determined based on the number of previous cycles in a therapy session, the number of cycles maintaining present settings (e.g., through box 446) in a therapy session, the number of particular successive cycles (e.g., number of successive cycles through box 446 or box 448 or box 452 or box 454 or box 458), the patient characteristics, environmental conditions, procedural approach, and/or product cycle lifetime (i.e., operable age), among other aspects. By deduction, in box 456, the threshold current value has not been achieved in the present cycle, although in some embodiments, affirmative determination and/or confirmation that threshold current value has not been achieved may be performed. Responsive to determination that maximum voltage has not been achieved, control proceeds to box 458. Otherwise, responsive to determination that maximum voltage has been achieved, control proceeds to box 460.

In box 458, determination is made to apply updated voltage. In the illustrative embodiment, the voltage has been updated in box 454 by increasing the presently selected voltage by the predetermined voltage interval, and determination to apply the updated voltage confirms and proceeds with the updated voltage. The duration was updated in box 445 to return to the value at the initial setting, exampled as 0.5 microseconds, and proceeds to be applied with the updated applied voltage. Proceeding with the updated voltage proceeds openly to return to box 442, to again apply electrical power to the electrodes to delivery therapy using the updated voltage and updated duration.

In box 460, determination of error occurs. Responsive to determination of error, an error message is provided. Such error message illustratively terminates the therapy session, but in some embodiments, may take other safety and/or communication actions, for example, such as displaying an error communication to a user.

In the illustrative embodiment, by deduction, responsive to error determination, the maximum voltage and maximum duration can be determined not to have generated a spark, although in some embodiments, insufficient spark generation may be determined. In some embodiments, responsive to error determination, failed and/or insufficient spark generation under maximum voltage and maximum duration may be determined by affirmative determination and/or confirmation. Following box 460, process control automatically terminate.

Within the discussion of the control 438, exemplary increases in duration have been mentioned, although in some instances, for example, in certain cycles of control 438, voltage level may be decreased, for example, in certain cycles of control 438. For example, duration and/or voltage may be changed in a given cycle according to control 438 to decrease incrementally to achieve appropriate conditions, for example, to achieve appropriate discharged energy as discussed in additional detail herein relative to consideration of the voltage levels of an energy storage system, for example, a capacitance system, 112 before and after discharge.

Figure 6A:
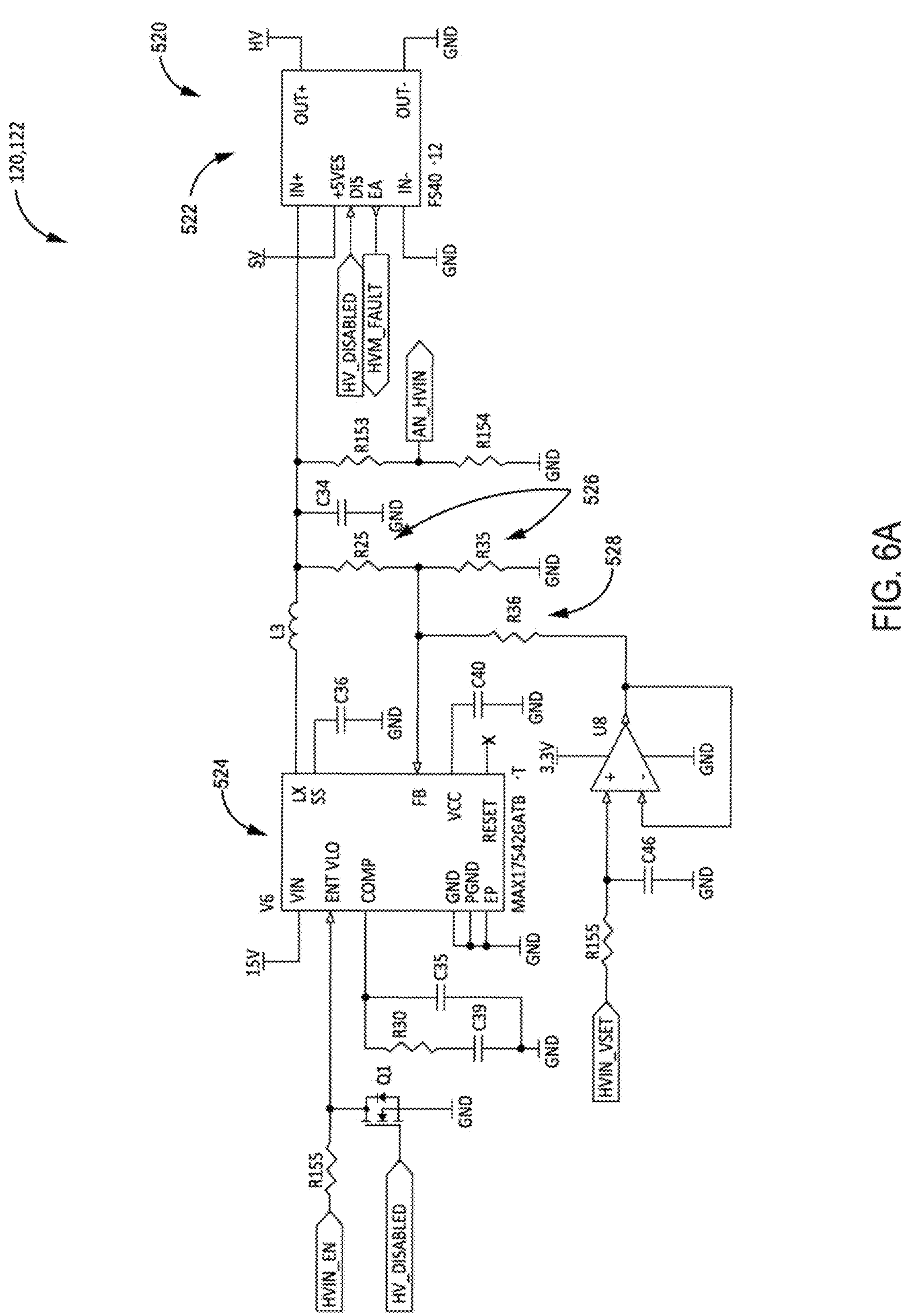
FIG. 6A illustrates portions of circuitry arrangements of the IVL arrangement of FIG. 1 according to one or more embodiments of the present disclosure.
Figure 6B:
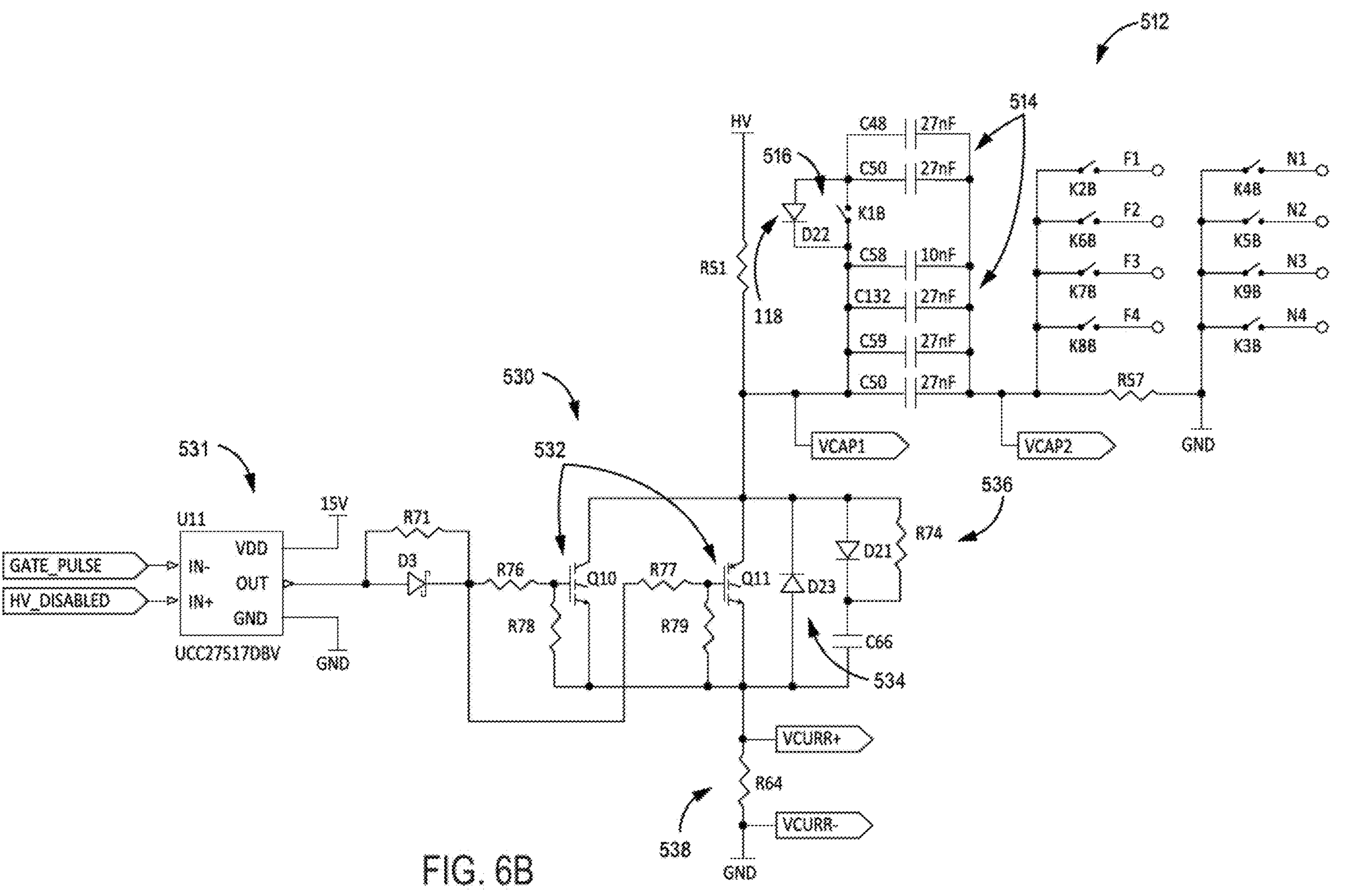
FIG. 6B illustrates portions of circuitry arrangements of the IVL arrangement of FIG. 1 according to one or more embodiments of the present disclosure.
Figure 7A:
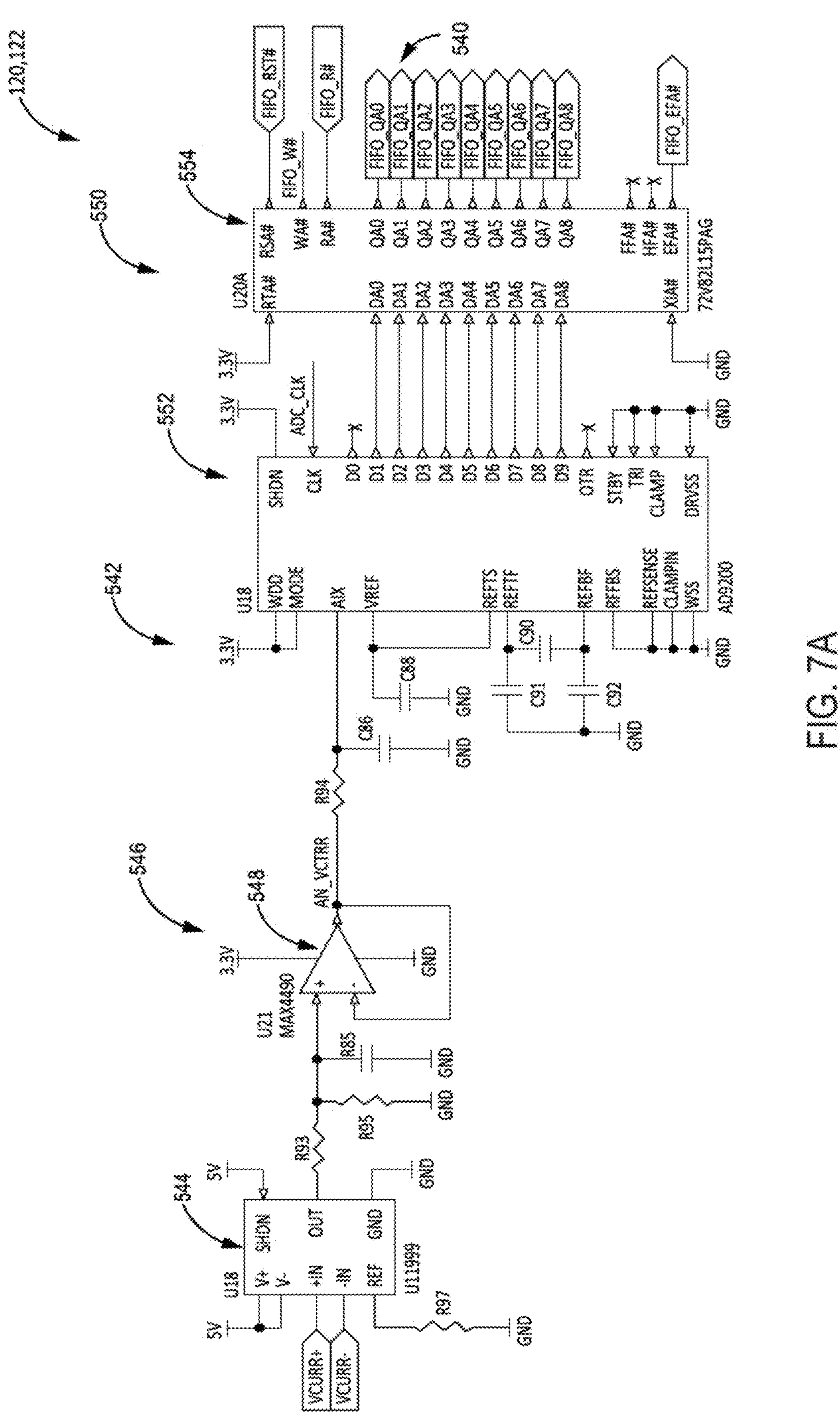
FIG. 7A illustrates additional portions of circuitry arrangements of the IVL arrangement of FIG. 1 according to one or more embodiments of the present disclosure.
Figure 7B:
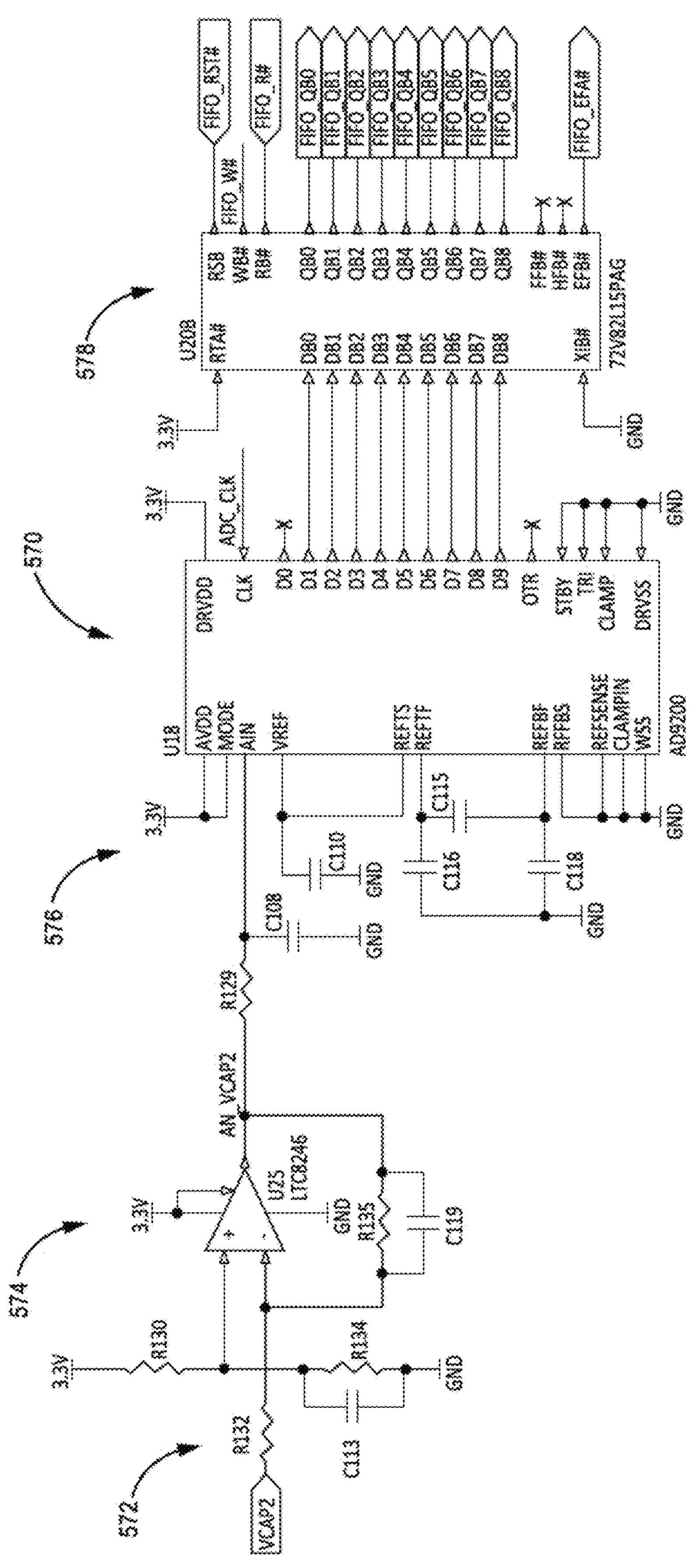
FIG. 7B illustrates additional portions of circuitry arrangements of the IVL arrangement of FIG. 1 according to one or more embodiments of the present disclosure.
Figure 7C:
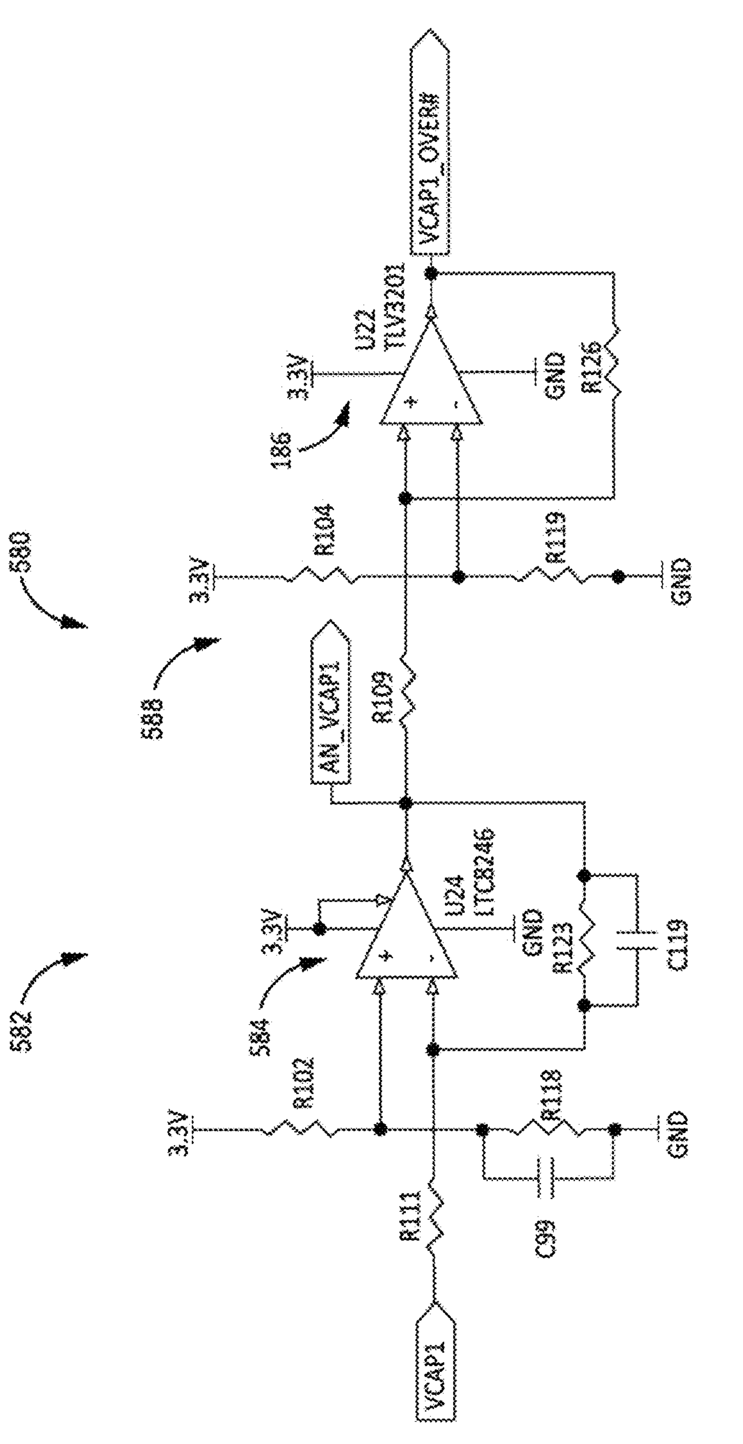
FIG. 7C illustrates additional portions of circuitry arrangements of the IVL arrangement of FIG. 1 according to one or more embodiments of the present disclosure.
Figure 7D:
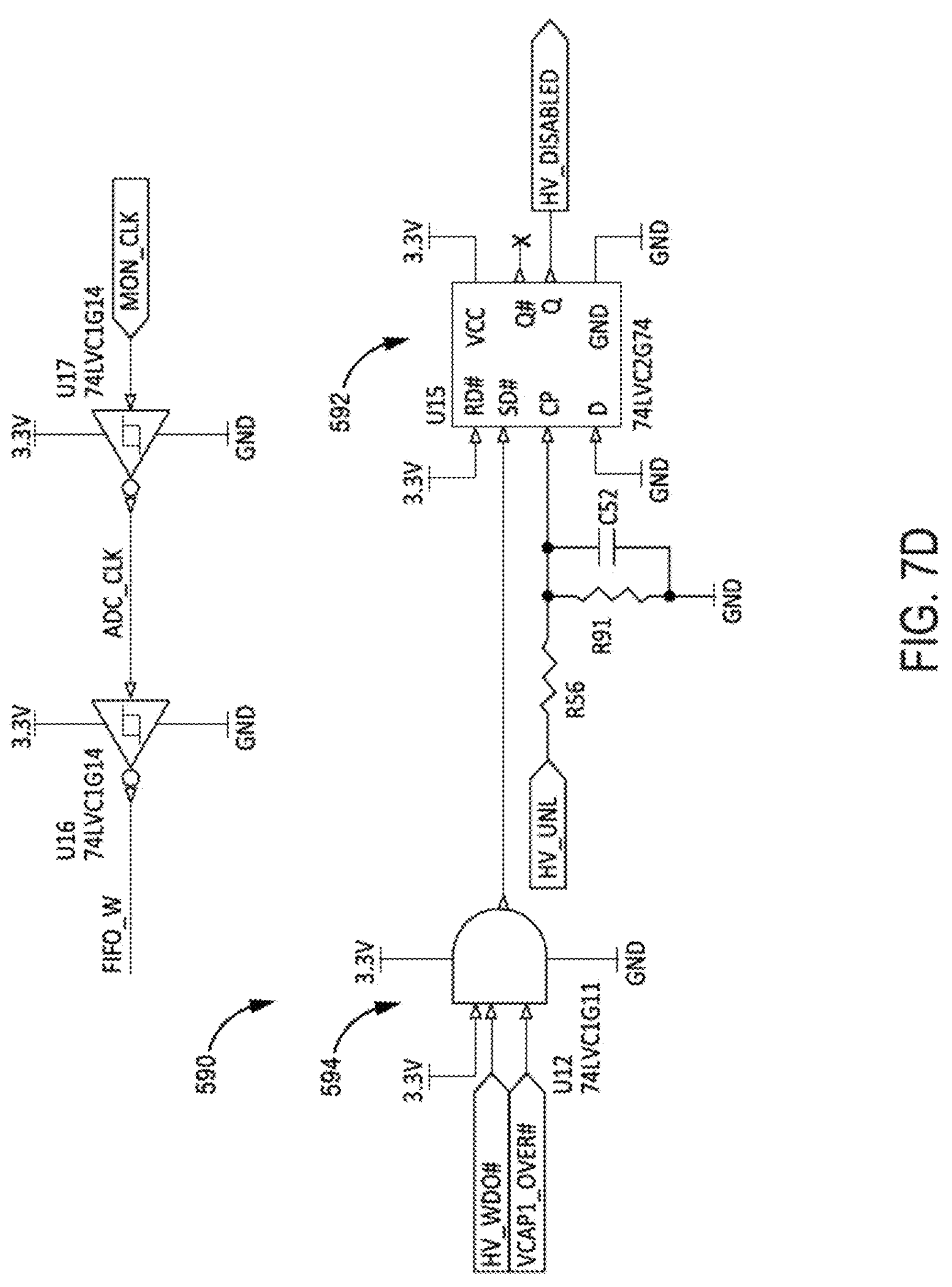
FIG. 7D illustrates additional portions of circuitry arrangements of the IVL arrangement of FIG. 1 according to one or more embodiments of the present disclosure.

With reference to FIGS. 6A and 6B, portions of the illustrative electric pulse generation system 120, including portions of the IVL control system 122, are disclosed herein including various features and/or circuitry, although in some embodiments, such systems 120, 122 may share components and/or have isolated components as applicable, for example, such that the circuitry illustrated is intended to be diagrammatic and may also represent circuitry embodied by system 120 alone as applicable. In the illustrative embodiment, the IVL control system 122 includes an adjustable energy storage system, illustratively an exemplary capacitance system, 512 for selective adjustment of the energy storage capacity or magnitude applied for providing electrical energy to the electrodes. We refer hereinafter to energy storage system 512, illustrated by but certainly not limited to, the illustrative capacitance system.

The energy storage system 512 receives charge electrical energy from a power source of the electric pulse generation system 120. The energy storage system 512 provides discharge electrical energy to the electrodes (e.g., illustratively via VCAP2 and grounding), as discussed in additional detail herein.

The adjustable energy storage system 512 illustratively includes a number, e.g., one or more, of energy storage units, exemplified as individual energy storage element 514 (e.g., capacitors), defining an energy storage network. In the illustrative embodiment, each energy storage element 514 may be sized to have the same energy storage capacity and may be arranged for parallel connection with the other energy storage unit(s) in the energy storage network, although in some embodiments, any suitable size and/or arrangement of the energy storage unit(s) may be provided to support variable energy storage for IVL therapy. A relay system 516 may be arranged in connection with at least some of the energy storage elements 514 of the network. The relay system 516 comprises one or more relays for selectively connecting energy storage element(s) 514 together to receive charge and to discharge electrical energy to the electrodes.

In the illustrative embodiment, the relay system 516 includes an engaged arrangement in which all energy storage elements 514 of the network are connected for IVL use. Energy storage element(s) 514, when connected for IVL use, may be connected with other portions of the electric pulse generation system 120 to exchange electrical energy under other control operations. For example, under typical charge control operations, energy storage elements 514 connected for IVL use by relay system 516 may receive charge from power supply, and/or under typical discharge control operation, energy storage elements 514 connected for IVL use by relay system 516 may provide discharge energy to the electrodes 18. Accordingly, it can be appreciated that the relay system 516 can selectively connect all energy storage element(s) 514 for use in the IVL therapy, to provide a maximum energy storage magnitude.

Additionally, the relay system 516 includes a disengaged arrangement in which fewer than all energy storage elements 514 of the network are connected for IVL use as suggested in FIGS. 7A-7D. A number of energy storage elements 514, illustratively two energy storage elements, are rendered disconnected from the other energy storage element(s) by disengagement of the relay system 516 for ease of description but without limitation. Energy storage elements 514 disconnected for IVL use by relay system 516 cannot receive charge from the power supply, and/or under typical discharge control operation, energy storage elements 514 disconnected for IVL use by relay system 516 cannot provide discharge energy to the electrodes 18. Energy storage elements which are disconnected for use in IVL therapy may be discharged apart from the electrodes (e.g., for safe reduction of stored power), illustratively via diode 518 arranged in parallel with the relay system 516.

It can be appreciated that by adjustment of the energy storage capacity available to provide electrical energy to the electrodes, the total amount of energy provided to the electrodes can be controlled. The stored energy can be indicated according to $\frac{1}{2}C*V^2$, where V represents the voltage and C represents the capacitance, such that applied electrical energy is directly proportional to the amount of energy connected in use. Accordingly, by selectively engaging the relay system 516 to close the circuit and connect the disconnected energy storage element(s), the energy storage capacity of the IVL system can be adjusted to provide variable energy levels to the electrodes. Although the illustrative embodiment includes relay control for connection and/or disconnection of a pair of energy storage elements, any suitable number of relays and/or energy storage elements may be applied to provide adjustable energy storage capacity for IVL therapy.

In the illustrative embodiment, the IVL control system 122 is configured to govern the applied stored energy. The IVL control system 122 illustratively determines the amount of stored energy to be applied, and upon determination that a change in the energy storage magnitude is desired, the IVL control system 122 operates the relay system 516 accordingly. For example, the IVL control system 122 may determine that one voltage pulse desires and/or requires lower energy storage magnitude and may communicate to operate the relay system 516 in the disengaged arrangement.

For one or more subsequent voltage pulses, the IVL control system 122 may determine that another voltage pulse desires and/or requires greater energy storage magnitude and may communicate to operate the relay system 516 in the engaged arrangement. For one or more further subsequent voltage pulses, the IVL control system 122 may determine that lower energy storage magnitude is again desired and/or required and may return the relay system 516 to the disengaged arrangement. Accordingly, the IVL control system 122 may operate the relay system 516 as needed to provide adjustable energy storage magnitudes for any given voltage pulse within a series of voltage pulses.

The applied energy storage may be adjusted on an ongoing basis, for example, for any given pulse. In practice, adjusting the energy storage capacity or magnitude may be conducted in conjunction with the level of voltage to be applied and/or in consideration of other aspects of power, efficiency, and/or technique. Moreover, under the lifetime of applied devices and systems, typical wear to components can alter the electrical and/or physical characteristics thereof, which may benefit from adjustment to the energy storage that is applied. For example, even small wear to electrodes can vary the spacing (gap) between a set of electrodes which can alter the conditions of the arc between electrodes. Accordingly, adjustable energy storage magnitude can accommodate variations in the electrodes and/or or portions of the discharge system under repeated use, whether in individual therapy sessions or otherwise.

With continued reference to FIGS. 6A and 6B, embodiments of the disclosure are directed to systems and methods for adjusting the voltage provided to charge the energy storage system 512 as charge voltage. The charge voltage is illustratively provided as input to the energy storage system 512 as energy accumulation for discharge to generate a voltage pulse, controlled for variable charge. The charge voltage is illustratively controlled by a charge control system 520 of the IVL control system 122.

In the illustrative embodiment, the charge control system 520 provides accurate control of charge voltage via high-frequency switched control signals from the processor 124. The switched control signal ("HVIN_VSET"), illustratively embodied as a pulse width modulated (PWM) signal, is amplified for control of high voltage supply. A high voltage DC/DC converter system 522 receives indication of the switch control signal within the range of about 0 V to about 12 V, and provides a corresponding charge voltage illustratively within the range of about 0 V to about 4000 V.

In the illustrated embodiment, the charge control system 520 includes a buck regulator system 524 for conditioning the low voltage power. The buck regulator system 524 is illustratively embodied as an integrated circuit (IC) to provide signal conditioning with low pass filtering and buffering of the PWM signal. The buck regulator system 524 receives a conditioned PWM signal with feedback for providing controlled low voltage power to the converter system 522 for applying high voltage power.

Resistors 526 can scale down the feedback voltage appropriately for the IC operation, to provide a variable feedback voltage to the buck regulator system 524 within a range of about 0 V to about 3.3 V at the additional resistor 528. As the duty-cycle of the PWM signal increases from zero to 100 percent, the filtered signal increases from zero volts to 3.3 volts, which can increase the current provided to the feedback network, and can require less voltage to achieve regulation, for example, at resistors, inductors, and/or capacitors arranged between the buck regulator system 524 and the converter system 522.

Referring still to FIGS. 6A and 6B, embodiments of the disclosure are directed to systems and methods for controlling the active time for discharge voltage pulses provided to the electrodes. A switching signal (e.g., "GATE_PULSE") is provided by the processor 124 for high voltage switching via low voltage signaling. In the illustrative embodiment, the switching signal is applied to precisely activate a discharge switch system 530. The discharge switch system 530 is illustratively embodied to implement a driver 531 and semiconductor devices 532 as gate switches.

The gate switches 532 are illustratively embodied as insulated gate bipolar transistors (IGBT) having n-type gate-controlled arrangement. On active state of the switching signal to the driver 531, the gate switches 532 are activated into their conducting state to communicate discharge of energy from the energy storage system 512 to the electrodes. On inactive state of the switching signal the gate switches 532 are deactivated into their non-conducting states, blocking discharge of the energy storage system 512 to the electrodes.

In the illustrative embodiment, the gate switches 532 are arranged as active high devices, although in some embodiments, may be implemented as active low devices. Gate-controlled, active high IGBTs can provide precision control of discharge from the energy storage system 512, but may be implemented by any suitable manner including by other suitable semiconductors (e.g., p-type, FET, etc.) and/or other control designs (e.g., collector, emitter control, etc.).

In the illustrative embodiment, the discharge switch system 530 includes an anti-parallel diode 534 arranged to reduce reverse-voltage stresses on the gate switches 532. A disable signal ("HV_DISABLED") is provided to the driver 531 which permits discharging of energy to the electrodes on inactive (low) signal, and may activate (high) to disable high voltage discharge under direction of the processor 124 and/or other safety systems. The snubber system 536 is illustratively embodied as a resistor-capacitor-diode (RCD) snubber network arranged to reduce voltage transients that may exceed rated voltages of various high-voltage components.

Referring now to FIGS. 7A-7D, the IVL control system 122 illustratively includes electrical power monitoring system 540. The electrical power monitoring system 540 is configured to conduct monitoring of various parameters of electrical power of the IVL device and systems, illustratively including sensing of current and voltage delivered to the electrodes, and voltage of the adjustable energy storage system 512.

The electrical power monitoring system 540 illustratively includes a current monitoring system 542. The current monitoring system 542 is embodied to sense the current delivered to the electrodes for a given voltage pulse. As discussed in additional detail herein, the current delivered to the electrodes can be considered in determining the power characteristics for subsequent voltage pulses.

In the illustrative embodiment as shown in FIGS. 4A-4D, the current monitoring system 542 receives indication of the voltage levels applied in each voltage pulse for determining current delivered to the electrodes. Returning briefly to FIGS. 3A and 3B, a shunt resistor 538 is arranged within the high-voltage current path establishing a proportional voltage (e.g., "VCURR+", "VCURR−"). The proportional voltage is communicated to the current monitoring system 542 as shown in FIGS. 4A-4D.

A chip comprising an amplifier 544 is arranged to scale-up the proportional voltage, and provides the analog result to a conditioning network 546, embodied to include a resistor-capacitor network for scaling and/or filtering. The conditioning signal is buffered by a buffering amplifier 548, the output of which is provided to an analog-to-digital conversion (ADC) system 550 for digital conversion.

The ADC system 550 illustratively includes a converter 552 and memory 554. In the illustrative embodiment, the converter 552 provides digital output from the analog input, and the memory 554 is embodied as a first-in-first-out (FIFO) device for intermediate storage of digital outputs. The memory 554 illustratively receives the same clock signal driving the converter 552, to allow quick sampling of a number of measurement points with low-jitter. Memory outputs are provided to the processor 124 for consideration in overall IVL therapy control.

The IVL control system 122 illustratively includes a current monitoring system which compares the output signal ("VCURR") generated by the chip comprising an amplifier 544 with a threshold value. The threshold value is embodied to be generated by a variable duty cycle PWM signal ("ISNS_ISET") from the processor 24. The PWM signal can be low-pass filtered and/or buffered before delivery to a comparator. Responsive to the measured current exceeding the threshold value, the current monitoring system can assert an error signal (e.g., "ISNS OVER #") to avoid overcurrent conditions.

The electrical power monitoring system 540 illustratively includes a voltage monitoring system 570. The voltage monitoring system 570 is embodied to sense the voltage between the set of electrodes. As discussed in additional detail herein, the voltage between the electrodes for a given pulse can be considered in determining the power characteristics for subsequent voltage pulses.

In the illustrative embodiment, the voltage monitoring system 570 includes a resistor network 572 arranged to attenuate the (switched) voltage of one of the electrodes of a set (e.g., "VCAP1"). The attenuated signal is provided to an op amp network 574 for filtering and offsetting for output to digital conversion. The output from the op amp network 574 is provided to the ADC conversion system 576 for digitization, including storage in FIFO memory 578 for access by the processor 124.

The electrical power monitoring system 540 may illustratively include an energy storage capacity voltage monitoring system 580 configured for monitoring the voltage within the adjustable energy storage system 512. Monitoring the voltage of the energy storage system 512 can allow determination of the stored energy of the energy storage system 512. Moreover, comparison of the stored energy of the energy storage system 512 before and after discharge can provide indication of the total energy delivered during a given discharge cycle. Such total energy data can be considered to increase confidence in determining whether a sufficient spark has been generated for IVL therapy.

In the illustrative embodiment, the voltage monitoring system 580 includes a voltage limiting system configured to monitor net voltage of the energy storage system 512 during charging. In the illustrative embodiment, voltage monitoring is discussed relative to the connected energy storage elements 514, more specifically, those energy storage elements which are connected to provide controlled discharge energy for IVL therapy, and not energy storage elements which are disconnected via the relay system 516 if any.

The voltage monitoring system 580 receives indication of the voltage of the energy storage system 512 during charging ("VCAP1"). The system 580 illustratively includes an amplifier configuration 582 comprising an amplifier 584 and a comparator 586. The comparator 586 is illustratively arranged to compare to the voltage with a fixed voltage, and to responsively trigger a signal (e.g., "VCAP1_OVER #") when the voltage of the energy storage system 512 exceeds the fixed voltage. In the illustrative embodiment, the fixed voltage is embodied as setpoint generated by a resistor-resistor-capacitor network 588 above normal operation, but before damage will occur to various HV components.

An intermediate voltage of this circuit (e.g., "AN_VCAP1") can be used to monitor progress during the charging cycle of the energy storage system 512. The intermediate voltage illustrative represents a heavily attenuated indication of the high voltage provided by the energy storage system to the electrodes ("VCAP_1"). Such attenuated signal can allow monitoring of high voltage systems while handling lower voltage indications thereof.

Figure 8:
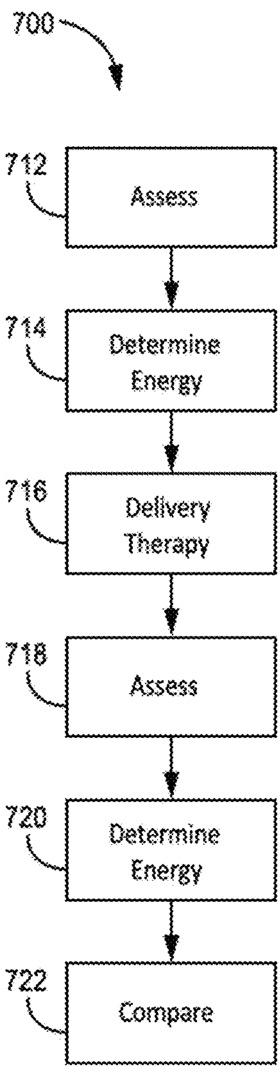
FIG. 8 illustrates a flowchart for controlling and delivering voltage to electrodes and generating shock waves according to one or more embodiments of the present disclosure.

Referring now to FIG. 8, and with continued reference to FIGS. 1 and 3, the IVL system 12 can consider energy of the energy storage system 512 in operation. By monitoring energy of the energy storage system 512 before and after a discharge event, indication of the generation (and/or sufficiency) of spark can be determined as discussed in additional detail regarding the illustrative embodiment with reference to operation 700 concerning boxes 712 through 722.

In box 712, assessment of the energy storage system 512 is conducted. In the illustrative embodiment, the assessment includes determination of a voltage of the energy stored by the energy storage system 512. As mentioned above, the voltage monitoring system 580 can monitor voltage of the energy storage system 512, for example, via the voltage limiting system during charging. In some embodiments, the assessment may include determination of any other suitable parameters to support energy monitoring of the energy storage system 512.

In box 714, the energy of the energy storage system 512 is determined. In the illustrative embodiment, the energy of the energy storage system 512 is determined based on the measured voltage according to $$\frac{1}{2}C*V^2.$$

Accordingly, the processor 124 can compute the current energy of the energy storage system 512, including the energy stored just before discharge of energy to the electrodes.

In box 716, IVL therapy can be attempted. In the illustrative embodiment, a voltage pulse can be delivered to the electrodes. The voltage pulse can be applied according to the control arrangement as mentioned herein, for example, based on a determined duration in a control sequence.

In box 718, assessment of the energy storage system 512 is conducted. Assessment of the energy storage system 512 in box 718 is embodied as occurring immediately after attempted IVL therapy in box 716 to provide an indication of the energy state of the energy storage system 512 immediately after (attempted) discharge to the electrodes. In the illustrative embodiment, the assessment includes determination of a voltage of the energy stored by the energy storage system 512, embodied as conducted by the voltage monitoring as mentioned above, although in some embodiments, assessment of the energy storage system 512 in box 718 may differ from box 712 in methodology and/or practice.

In box 720, the energy of the energy storage system 512 is determined. In the illustrative embodiment, the energy of the energy storage system 512 is again determined based on the measured voltage according to $$\frac{1}{2}C*V^2$$

just as in box 714, yet after attempted delivery of IVL therapy. In some embodiments, determining energy of the energy storage system 512 in box 720 may differ in methodology and/or practice from that in box 714. Accordingly, the processor 124 can compute the current energy of the energy storage system 512, including immediately after (attempted) discharge of energy to the electrodes.

In box 722, comparison between energy determinations is conducted. The amount of energy determined within the energy storage system 512 in box 714 is illustratively subtracted from the amount of energy determined within the energy storage system 512 in box 720, such that the result represents the amount of energy discharged from the energy storage system 512 under a single attempt to deliver IVL therapy.

The amount of energy discharged can be considered to determine whether a spark (or sufficient spark) has occurred such that IVL therapy occurs. In the illustrative embodiment, a threshold energy discharge represents a discharged energy level which confidently indicates spark sufficient for IVL has occurred. Accordingly, in box 722, comparing the stored energy levels before and after discharge to determine whether the threshold energy discharge has been achieved can indicate spark for IVL therapy.

In the illustrative embodiment, and with reference to FIG. 5, the threshold energy discharge is a fixed predetermined value, for example, 600 millijoules (e.g., 3700 V, 90 nanofarad). However, in some embodiments, the threshold energy level for a given cycle may be determined based on the number of previous cycles in a therapy session, the number of cycles maintaining present settings (e.g., through box 446 of FIG. 5) in a therapy session, the number of particular successive cycles (e.g., number of successive cycles through box 446 or box 448 or box 452 or box 454 or box 458), the patient characteristics, environmental conditions (e.g., location within patient's body such as above the knee or above the knee), procedural approach, and/or product cycle lifetime (i.e., operable age), among other aspects.

Comparison of energy levels of the energy storage system 512 which indicates a spark for IVL therapy has occurred can responsively cause further therapy at the same duration, energy level, threshold characteristic, and/or threshold adjusted for other parameters. Comparison of energy levels of the energy storage system 512 which indicates a spark for IVL therapy has not occurred can cause adjustment to the duration and/or energy level applied, for example, as discussed concerning control operation 38.

In some embodiments, the threshold current value can be applied together with the threshold energy discharge, such that either threshold can individually indicate a spark for IVL therapy. In some embodiments, both thresholds may be required to be met to indicate a spark for IVL therapy.

Consideration of the energy states of the energy storage system 512 can provide desirable monitoring of IVL operations. For example, such monitoring can be less intrusive by reducing the need for direct measurements at the electrodes. Moreover, in high power applications, reliable consideration of the energy states can promote confidence over mere direct measurement in unpredictable high energy arc scenarios.

The IVL control system 122 illustratively includes an external watchdog system configured to assist in safe operation. The watchdog system includes an integrated circuit configured to trigger an error under lack of a timely toggled input signal to ensure appropriate high voltage operation. In some embodiments, the watchdog system may be formed externally including processor, memory, and/or circuitry distinct from or shared with the IVL control system 122.

Returning to FIGS. 7A-7D, in the illustrative embodiment, the IVL control system 122 includes an umbrella monitoring system 590 configured to assist in safe operation. The umbrella monitoring system 590 illustratively includes a flip flop 592 and logic gate 594 for consideration of monitoring signals. The logic gate 594 is arranged to receive monitoring signals, embodied as energy storage system overvoltage ("VCAP1_OVER #") from the voltage monitoring system 580, high voltage warning ("HV_WDO #) from the watchdog system, and in some embodiments, may receive overcurrent from the current monitoring system ("ISNS_OVER #").

The logic gate 594 is embodied as an AND gate and the flip flop 592 embodied as an asynchronous D-flip flop, such that activation signals from the gate 594 which last longer than the minimum clock pulse width of the flip flop 592 cause an assertion of outputs to disable high voltage output (e.g., "HV_DISABLED"), but activation signals from the gate 594 shorter than the minimum clock pulse width of the flip flop 592 do not raise disabling outputs from the umbrella monitoring system 590.

Assertion of the signal to disable high voltage output ("HV_DISABLED") is illustratively provided to the discharge switch system 530 to disable voltage pulse switch activation to the electrodes. In the illustrative embodiment, the disabling output signal is provided to the driver 531 and indirectly to alter on/off operation of the gate switches 532. Such disabling output signal is illustratively provided to low-voltage supplies, e.g., buck regulator system 524, and high voltage modules, e.g., converter system 522.

Accordingly, the logic gate 594 receives monitoring signals discussed above comprising: (1) energy storage system overvoltage ("VCAP1_OVER #") from the voltage monitoring system 580, (2) high voltage warning ("HV_WDO #) from the watchdog system, and in some embodiments, (3) may receive overcurrent from the current monitoring system ("ISNS_OVER #"). These monitoring signals ae also connected to a three-input AND logic gate [U12], which is upstream of a D flip-flop with asynchronous set and reset functionality [U15], so that any signal that asserts for longer than the minimum pulse width of the flip-flop [U15] will cause its outputs [HV_DISABLED, HV_DISABLED #] to assert. These signals travel downstream and inhibits the operation of the gate driver [U11], variable low-voltage supply [U6], high-voltage module [U7], and slightly changes the turn-on and turn-off operation of the switching devices [Q10, Q11] via transistors [Q12, Q13]." This system allows any one of monitoring signals to disable the output of the system if asserted longer than an established duration.

Within the present disclosure, the ability to run off of AC mains or battery DC can afford versatility of power and control for IVL therapy. Unlike known IVL systems, certain embodiments within the present disclosure can avoid sitting idle until fully (or substantially) recharged in order to be applied in IVL therapy, for example, if insufficiently charged by the time IVL therapy is desired. Accordingly, such costly delays, or interruptions, in procedure can be avoided with embodiments of the present disclosure. The electric pulse generation system 120 illustratively includes a battery power storage system, and is configured to selectively charge the energy storage system 512 from battery stored energy only, from the battery power storage system while connected to mains, such as outlet power, or directly from DC power converted from the AC mains without the battery power storage system. When plugged in to AC mains, regulated DC power is delivered directly to the high voltage systems. In operational states in which the current demand for IVL operations is high, the battery power storage system charge current can be reduced to allow for higher IVL operations system current. When not plugged in to AC mains, battery power can be delivered directly to energy storage system 512. In the illustrative embodiment, systems and devices of power management, including for example, inverters, conditioners, power storage devices, and/or related aspects may be comprised by the electric pulse generation system 120 to provide applicable power to the IVL control system 122.

Within the present disclosure, consideration of a set of discharge electrodes has been discussed in the context of a pair of electrodes, one of which may serve as a cathode and the other of which may serve as an anode, at a given instance. However, the number of electrodes in a set may be greater than a pair, for example, including one or more cathodes communicating with one or more anodes. Additionally, devices, systems, and methods within the present disclosure may include more than one communicating group of electrodes, whether electrically arranged serially, in parallel, or independently from each other.

Power control operations disclosed herein may be applied equally, simultaneously, and/or sequentially to individual sets or groups of electrodes, in a given IVL therapy cycle. For example, threshold current value may be applied collectively to all deployed electrodes or to individual groups or sets of electrodes. Determinations made with respect to power control may be applied equally to related electrodes, or may be individualized to groups or sets of electrodes, in a given IVL therapy cycle. Within the present disclosure, supporting components, such as power supplies, sensors, and other implementing structures and/or features for performing IVL operations as disclosed herein are embodied as sub-portions of the electric pulse generation system 120 and/or IVL control system 122, for example, as parts of circuitry and/or instructions.

Figure 9:
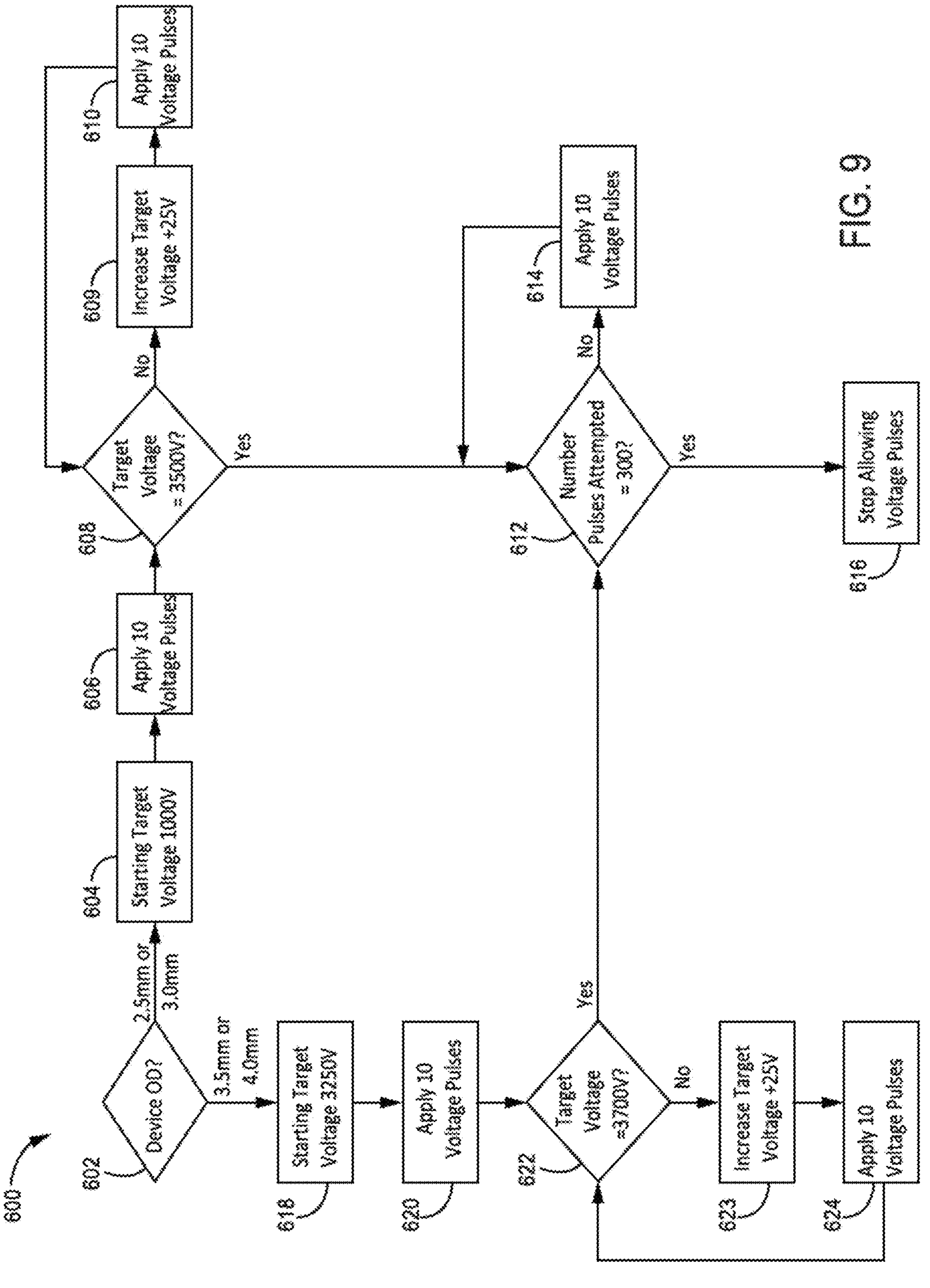
FIG. 9 illustrates a control operation flow applicable to the IVL arrangement of FIG. 1 according to one or more embodiments of the present disclosure

Referring now to FIG. 9, an exemplary flow diagram is shown concerning another embodiment of a control 600 in operation of an embodiment of an IVL system, specifically the number of voltage pulses generated and the magnitude of the generated pulses. It is understood that the control 600 may be combined with aspects of the control system and method embodiments described above.

Control operations of control 600 may be governed by the electric pulse generation system 120, and illustratively by the IVL control system 122 discussed above. As discussed further herein, control system 122 may control the number of generated voltage pulses in a series (or a plurality of series) of voltage pulses. An acceptable voltage window comprises a predetermined starting voltage magnitude and a predetermined upper voltage magnitude. IVL control system further comprises a predetermined voltage magnitude for incremental increasing of voltage magnitude after each series of voltage pulses if the magnitudes of the executed voltage pulses is within the acceptable voltage window. Separate sets of predetermined control data may be provided in control system 122 for IVL systems comprising balloons that are of identifiable characteristics such as, without limitation, different sizing, e.g, 2.5 mm, 3.0 mm, 3.5 mm and/or 4.0 mm.

An exemplary embodiment of an IVL system may comprise a 2.5 mm or a 3.0 mm balloon, wherein the control system 122 comprises control data comprises an exemplary starting target voltage of 3000V (predetermined lower voltage threshold), voltage pulse series comprising an exemplary 10 pulses, and an exemplary incremental voltage increase of 25V if the voltage pulse series magnitudes are less than an exemplary upper voltage threshold of 3500V. As the skilled artisan will recognize, the incremental voltage increase may comprise any voltage magnitude, including without limitation within 1V to 250V. An exemplary voltage increase may comprise 25V, but may be greater or less than 25V in certain embodiments. As the artisan will recognize, the predetermined starting voltage may be less than 3000V and the predetermined upper voltage threshold may be greater than 3500V. Thus, an exemplary starting voltage may, without limitation, comprise 2500V and an exemplary upper voltage threshold may comprise 4100V. In other embodiments, an exemplary predetermined starting voltage may be greater than 3000V and an exemplary upper voltage threshold may be greater than 3250V.

Another exemplary embodiment may comprise a 3.5 mm or a 4.0 mm balloon, wherein the control system 122 comprises control data comprises an exemplary starting target voltage of 3250V (predetermined lower voltage threshold), voltage pulse series comprising 10 pulses, and an incremental voltage increase of 25V if the voltage pulse series magnitudes are less than an exemplary predetermined upper voltage threshold of 3700V.

FIG. 9 illustrates initiation of a voltage pulse generation and control system that begins with box 602 which requires determination of a particular balloon characteristic of interest, for example the outer diameter ("OD") of the IVL system's balloon. In a first embodiment, if the balloon's outer diameter is, e.g., 2.5 mm or 3.5 mm, then in box 604 the starting voltage is set to 3000V, also referred to as the predetermined lower voltage threshold of the acceptable voltage magnitude window). The IVL therapy is initiated in box 606 by application of a series of voltage pulses (or shocks) from the electric pulse generation system 120 wherein each voltage pulse travels to the electrodes 18 within the balloon 16. If, in box 608, the target voltage magnitude is not at the predetermined upper voltage threshold, e.g., 3500V, then as in box 609, the target voltage is increased by an exemplary 25V (from 3000V to 3025V) and another series of voltage pulses (in this case 10 pulses) is executed, as in box 610 at 3025V. This process continues with cycling between boxes 608, 609 and 610 until the target voltage is at 3500V. When the target threshold voltage, or predetermined upper voltage threshold, is reached, and/or in some embodiments a predetermined maximum or desired number of voltage pulses, e.g, 300 pulses (or shocks) have been generated, then as in box 612, control system 122 determines if the number of generated voltage pulses (or shocks) in the plurality of series of voltage pulses has reached a maximum, or desired, number of pulses, e.g., 300 voltage pulses. If the maximum or desired, e.g., 300, voltage pulse threshold has not been reached, then as in box 614 another series of, e.g., 10, voltage pulses (or shocks) are applied. When the maximum or desired, e.g., 300 voltage pulse threshold has been reached, then as in box 616, additional voltage pulses (or shocks) are not allowed.

The predetermined maximum number of voltage pulses in various embodiments of the present disclosure may be within the range of 10-300 voltage pulses. The exemplary embodiments discussed herein comprise a predetermined maximum number of voltage pulses equal to 300 pulses. In other embodiments, the maximum number of voltage pulses may be greater than 300 pulses.

In a second embodiment, if the balloon's outer diameter is determined in box 602 to be, e.g., 3.5 mm or 4.0 mm, then the electric pulse generation system 120 initiates therapy at box 618 the starting voltage is set to 3250V, also referred to as the predetermined lower voltage threshold of the acceptable voltage magnitude window). The IVL therapy is initiated in box 620 by application of a series of voltage pulses from the electric pulse generation system 120 wherein each voltage pulse travels to the electrodes 118 within the fluid filled member 116. If, in box 622, the target voltage magnitude is not at the predetermined upper voltage threshold, e.g., 3500V, then as in box 623, the target voltage is increased by an exemplary 25V (from 3250V to 3275V) and another series of voltage pulses (in this case 10 pulses) is executed, as in box 624, at 3275V. This process continues with cycling between boxes 622, 623 and 624 until the target voltage is at 3700V. When the target threshold voltage, or predetermined upper voltage threshold, is reached, and/or in some embodiments a maximum or desired number of pulses, e.g, 300 pulses (or shocks when applied to the one or more pairs of spaced-apart electrodes) have been generated, then as in box 612, control system 122 determines if the number of generated voltage pulses (or shocks) in the plurality of series of voltage pulses has reached a maximum, or desired, number of pulses, e.g., 300 voltage pulses. If the maximum or desired, e.g., 300, voltage pulse threshold has not been reached, then as in box 614 another series of, e.g., 10, voltage pulses (or shocks) are applied. When the maximum or desired, e.g., 300 voltage pulse threshold has been reached, then as in box 616, additional voltage pulses (or shocks) are not allowed.

Alternatively, the physician conducting the IVL therapy according to the voltage pulse generation and control system may determine that the therapy is complete at a point during execution of the therapy. If the therapy is determined to be completed, then the physician may terminate the process of the voltage pulse generation and control system at any point.

In some embodiments, the voltage pulse generation and control system may comprise modification of the duration of applied voltage within, or across, one or more of the plurality of series of voltage pulses in accordance with the embodiments discussed above in connection with FIG. 5. For example, duration may be increased, or decreased, by a predetermined duration interval, illustratively embodied as a fixed value, e.g., 0.5 microseconds. In some embodiments, the predetermined interval for given cycle may be determined based on factors such as the number of times therapy cycles have ensued previously during the therapy session (e.g., number of series of voltage pulses that have been executed by proceeding through boxes 606, 608 and 610, or 620, 622 and 624), the patient characteristics, environmental conditions, procedural approach, and/or product cycle lifetime (i.e., operable age), among other aspects. In some embodiments, the predetermined duration interval for a given cycle may be varied by predetermined rate of change, for example, by percentage gain or loss by cycle.

Figure 10:
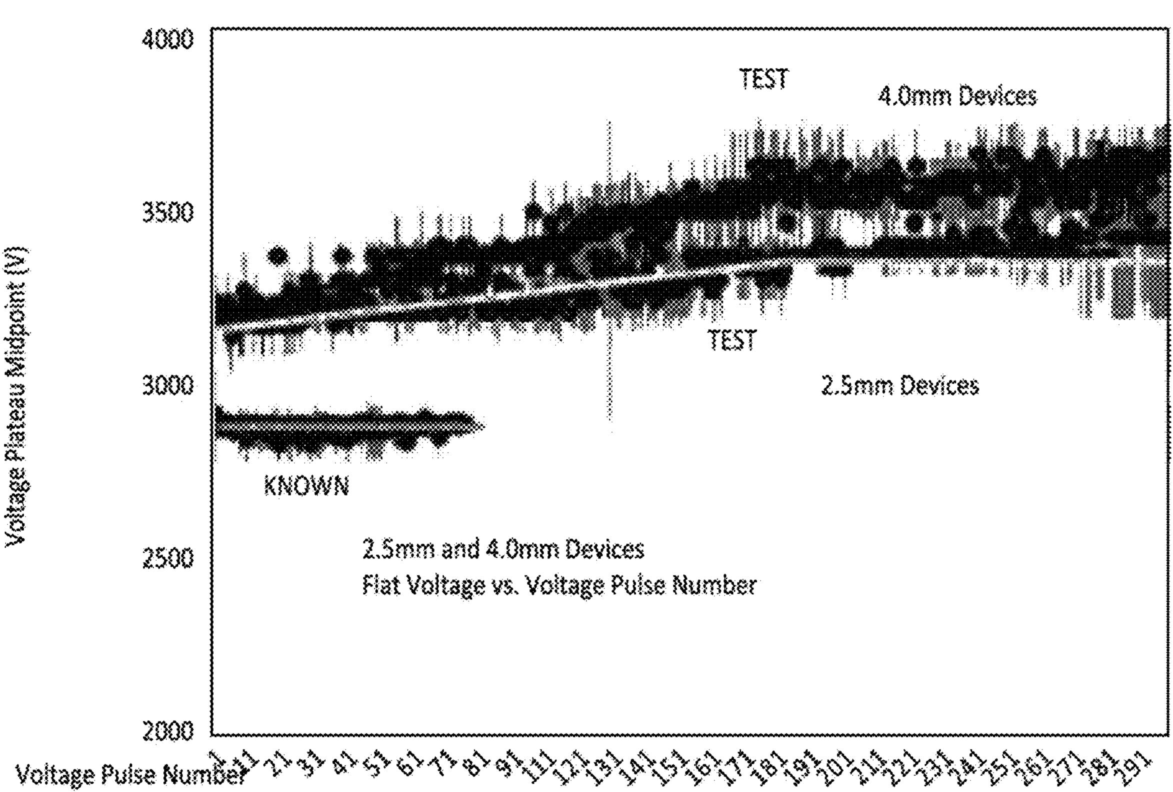
FIG. 10 illustrates graphic comparisons of voltages applied to a known IVL device and to embodiments of IVL devices according to the present disclosure.

FIG. 10 presents a graphic comparison of known IVL devices comprising 2.5 mm and 4.0 mm OD balloons (KNOWN) with IVL devices according to the present disclosure and comprising 2.5 mm and 4.0 mm OD balloons (TEST).

The KNOWN devices permit 80 voltage pulses or shocks to be generated. The TEST devices generated 300 voltage pulses or shocks. During the comparative testing, for each voltage pulse, the voltage peak magnitude was obtained and plotted for each tested device. The KNOWN devices provide a relatively flat or constant voltage for each voltage pulse or shock number and begin at a lower voltage magnitude than the TEST devices. The TEST devices were operated and controlled in accordance with the disclosed embodiments herein.

In contrast, each of the 2.5 mm and 4.0 mm TEST devices begin at a higher voltage magnitude than the KNOWN devices. The 2.5 mm TEST device begins at a lower voltage than does the 4.0 mm device. As illustrated, both the 2.5 mm and the 4.0 mm TEST device voltage (lower data cluster) rise slowly over the generated voltage pulses, plateauing at approximately 180 pulses, thereafter remaining substantially flat or constant. Referring back to FIG. 9, this pattern of increasing voltage, followed by a flattened or constant voltage region conforms with boxes 604-610 (2.5 mm) and boxes 618-624 (4.0 mm). In each case, the average voltage of the 4.0 mm TEST device is greater than that of the 2.5 mm TEST device.

Figure 11:
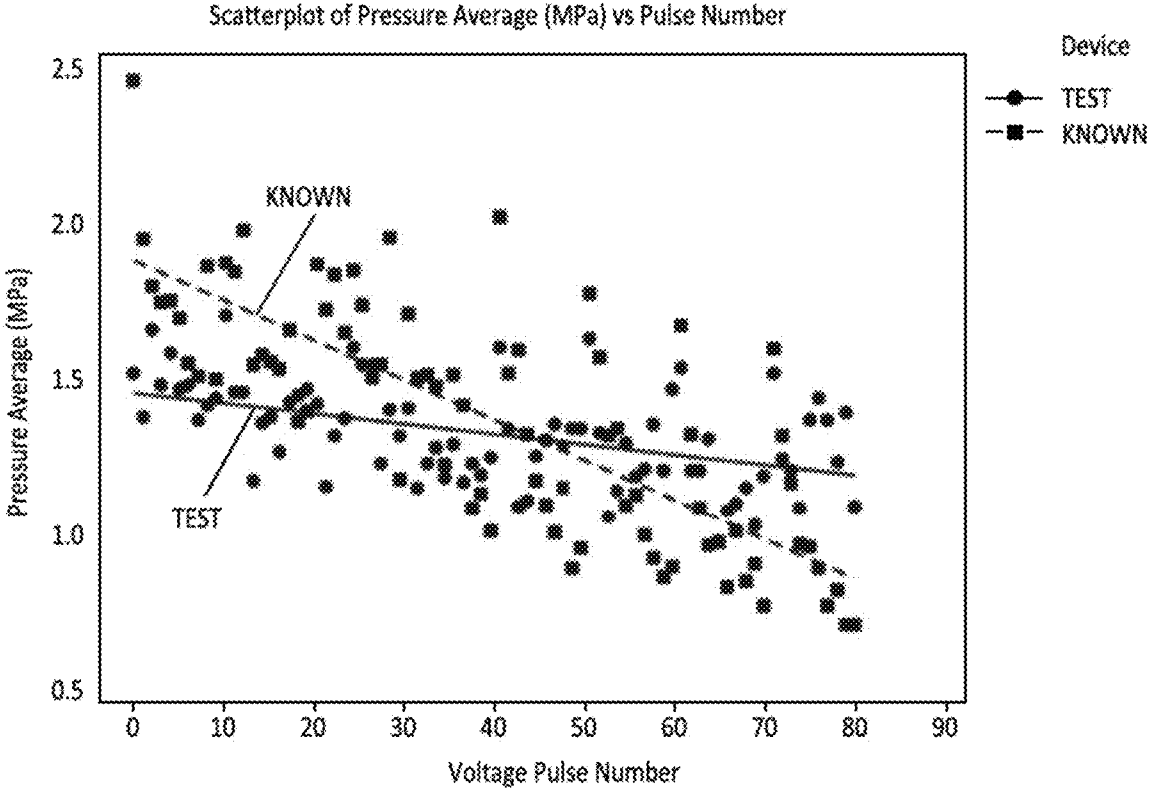
FIG. 11 illustrates a graphic comparison of average peak pressure generated over 80 voltage pulses by a known IVL devices and embodiments of IVL devices according to the present disclosure.

FIG. 11 illustrates a comparison of the TEST and KNOWN IVL devices and a subset of the data of FIG. 10, i.e., comparing the first 80 voltage pulses for each device. Here, the voltage pulse (or shock number) is compared with the average pressure generated during each voltage pulse. The KNOWN data (with a constant voltage in each voltage pulse presents (dashed line) a relatively severe decrease in pressure output as the voltage pulses progress over time. In contrast, the TEST data (solid line) obtained using the voltage and pulse generation algorithm of FIG. 9, presents a pressure output line that decreases at a much smaller angle or slope. Thus, the pressure output of the TEST IVL devices provides a more stable or constant pressure output than the KNOWN IVL devices. The KNOWN IVL devices have a pronounced pressure output decay as the voltage pulses progress. More specifically, the TEST IVL devices provide a decrease in pressure output over 80 pulses that is less than 0.25 MPa.

The pressure output, as tested, was measured in-vitro using pressure sensors (hydrophones) positioned externally to the catheter balloon within the acoustic field generated by device pulse delivery. The device under test and hydrophones were immersed in de-gassed, deionized water maintained at approximately body temperature.

Figure 12:
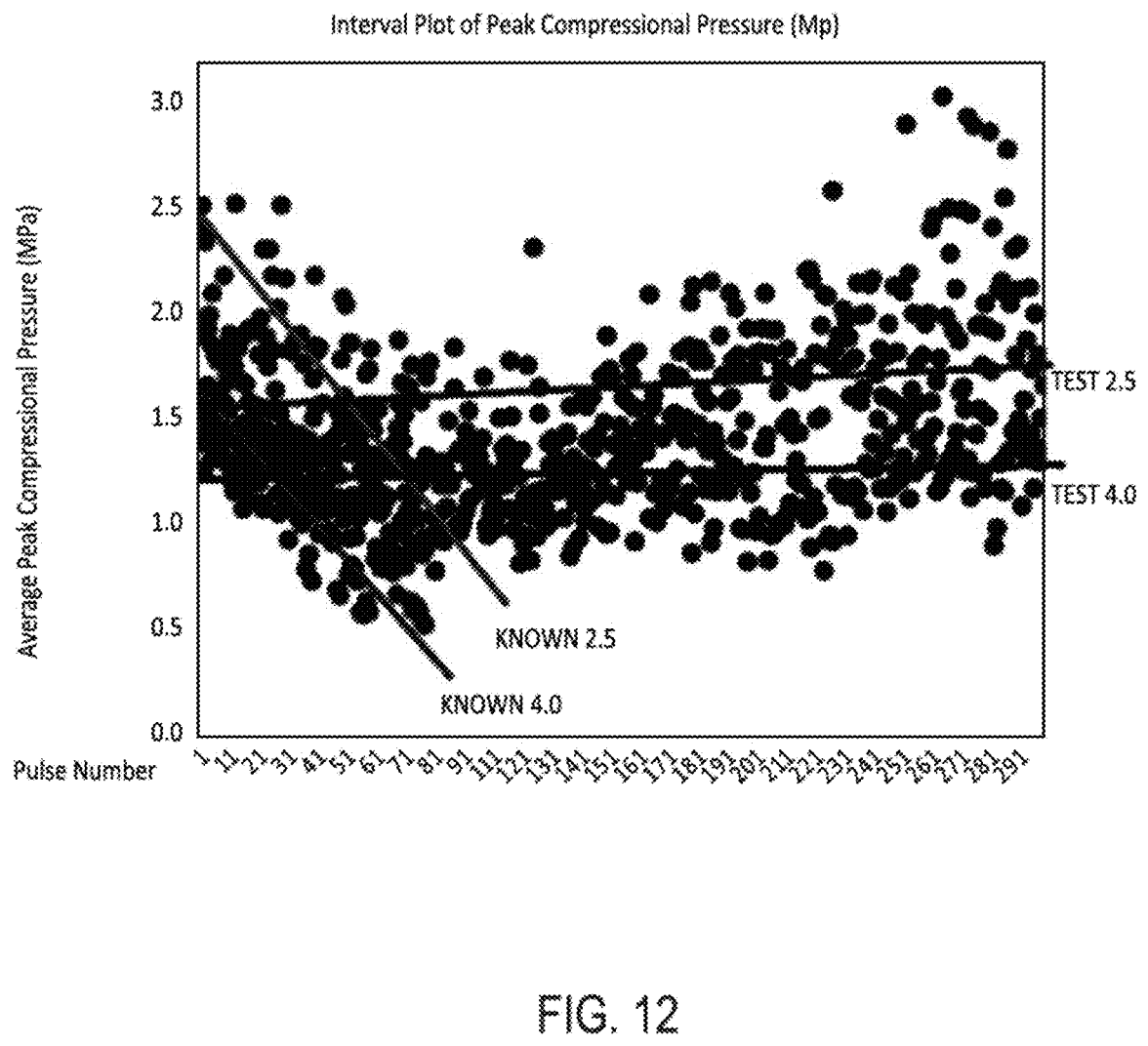

This concept is further demonstrated in FIG. 12, where the average pressure generated by 80 pulses of the KNOWN IVL devices (2.5 mm and 4.0 mm) with constant voltage magnitude is compared with the average pressure generated by the TEST IVL devices (2.5 mm and 4.0 mm) according to the voltage pulse and control method of FIG. 9.

As shown in FIG. 12, the KNOWN 2.5 mm and 4.0 mm devices both provide severely decreasing pressure output slope lines as the voltage pulses progress to 80 pulses. In contrast, the TEST 2.5 mm and 4.0 mm devices provide relatively flat, constant or stable pressure output slope lines as the voltage pulses progress to 300 pulses. Moreover, the slopes of the TEST pressure output lines appear to increase slightly as the voltage pulses progress which may be beneficial in cracking difficult calcified regions. Again, the KNOWN IVL devices have a pronounced and significant pressure output decay over 80 pulses. The TEST IVL devices do not have a pressure decay over 300 voltage pulses.

In summary, the IVL devices operated and controlled according to the present disclosure provide an increasing voltage to the voltage pulses until the upper voltage magnitude threshold is reached. Then, the voltage progress at the upper voltage magnitude threshold until 300 pulses have been executed, or the physical determines therapy is complete. This, as shown above, leads to constant and/or slightly increasing pressure output from each voltage pulse. The pressure output magnitudes, and associated slopes, may be manipulated by modifying the magnitude of each incremental increase in voltage. In some embodiments, the voltage magnitude may be incrementally increased as in FIG. 5. In others, the voltage magnitude may be increased incrementally for at least two series of voltage pulses, then held constant for one or more voltage pulses, then subsequent voltage pulse series may resume the incremental increase in magnitude. In other embodiments, the voltage magnitude may be decreased for one or more series of voltage pulses. All combinations of voltage increase, voltage decrease, and/or no change in voltage over a plurality of a series of voltage pulses in order to manipulate the resulting pressure output are within the scope of the present invention.

In addition, with reference to the above disclosure, various embodiments of the disclosure may provide a pressure output that is substantially the same for all balloon sizes, wherein the balloon sizes may be within a range from 2 mm to 4 mm outer diameter. In these embodiments, larger balloon sizes do not necessarily result in a lower pressure output than the pressure output of a relatively smaller balloon size.

The data of FIGS. 11 and 12 also demonstrate that IVL devices operated according to the present disclosure are also capable of stable operation and pressure output over at least 300 voltage pulses. This is in contrast to the pronounced pressure decay of the KNOWN IVL devices over just 80 voltage pulses.

Moreover, the data of FIGS. 11 and 12 confirm that the IVL control system 122 shown in FIG. 1 is controllable such that the pressure output following an electrical arcing event between two spaced-apart electrodes can be controlled within upper and lower pressure magnitude thresholds or a pressure magnitude window. Further, the pressure output can be controlled using embodiments of the present disclosure in a pattern of increasing pressure over the procedure, decreasing pressure over the procedure, constant pressure over the procedure, and any combination thereof.

Examples of suitable processors may include one or more microprocessors, integrated circuits, system-on-a-chips (SoC), among others. Examples of suitable memory, may include one or more primary storage and/or non-primary storage (e.g., secondary, tertiary, etc. storage); permanent, semi-permanent, and/or temporary storage; and/or memory storage devices including but not limited to hard drives (e.g., magnetic, solid state), optical discs (e.g., CD-ROM, DVD-ROM), RAM (e.g., DRAM, SRAM, DRDRAM), ROM (e.g., PROM, EPROM, EEPROM, Flash EEPROM), volatile, and/or non-volatile memory; among others. Communication circuitry 58 includes components for facilitating processor operations, for example, suitable components may include transmitters, receivers, modulators, demodulators, filters, modems, analog/digital (AD or DA) converters, diodes, switches, operational amplifiers, and/or integrated circuits. In some embodiments, memory 26 may represent one or more memory devices operable for IVL therapy operation. For example, each memory (e.g., 554, 578) may be included as part of memory 26, shared, or isolated therefrom.

Within the present disclosure, consideration of a set of discharge electrodes has been discussed in the context of a pair of electrodes, one of which may serve as a cathode and the other of which may serve as an anode, at a given instance. However, the number of electrodes in a set may be greater than a pair, for example, including one or more cathodes communicating with one or more anodes. Additionally, devices, systems, and methods within the present disclosure may include more than one communicating group of electrodes, whether electrically arranged serially, parallel, or independently from each other.

Figure 13:
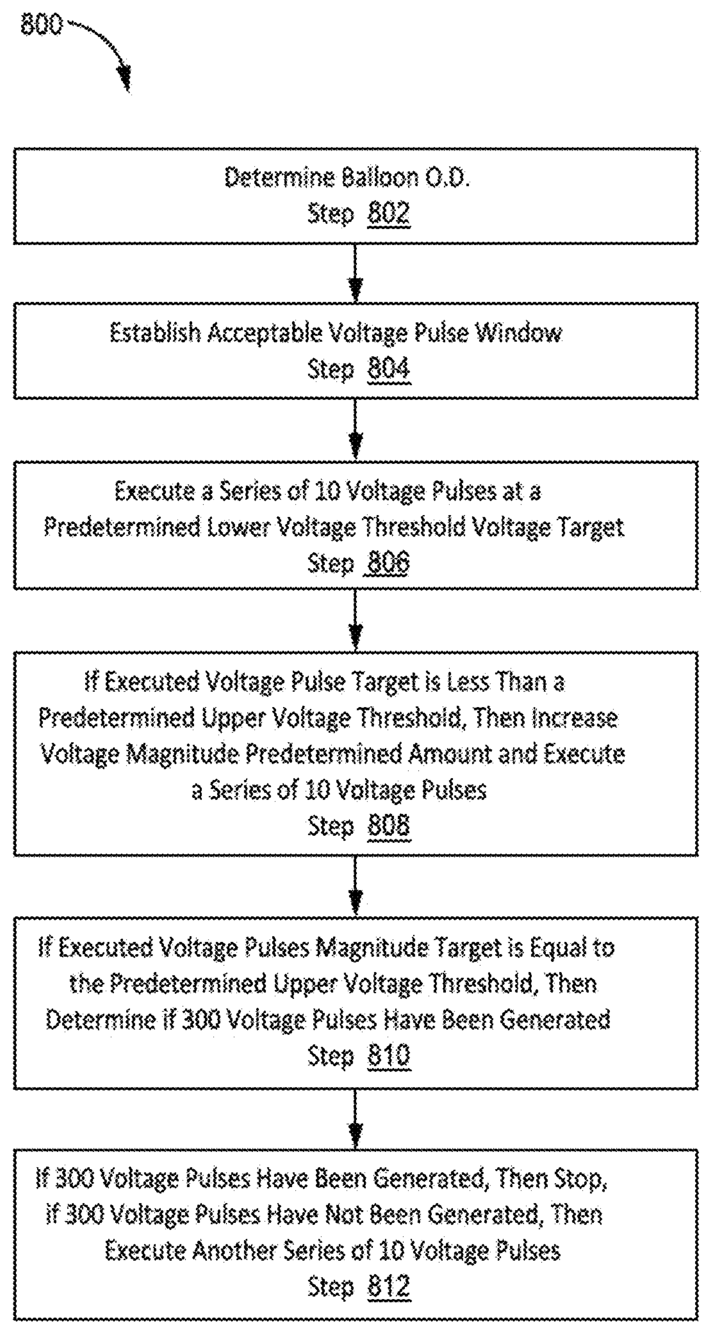
FIG. 13 illustrates an exemplary flowchart method according to the present disclosure.

FIG. 13 provides an exemplary flowchart illustrating an exemplary method 800 of one embodiment of the present invention. Thus, step 802 provides for determination of the subject IVL device's balloon outer diameter or OD. This may be done with manual entry into the IVL control system discussed above. Alternatively, connecting the catheter with the IVL control system may provide automatic detection and determination of the balloon's OD. Step 804 provides for establishing an acceptable voltage pulse window, comprising as described above, predetermined lower and upper voltage magnitude thresholds which may be stored in the IVL control system. Step 806 provides for execution of a series of voltage pulses to be controlled and generated by the IVL control system, in an illustrative and exemplary case 10 pulses may be used, at the predetermined lower voltage magnitude threshold. Step 808 provides that if the IVL control system determines that the last executed series of voltage pulses was not executed at the predetermined upper voltage threshold target, then the IVL control system may instruct execution and generation of another series of voltage pulses. Step 810 provides that if the IVL control system determines that the last executed series of voltage pulses was executed at the predetermined upper voltage threshold target, then the IVL control system seeks to determine if the illustrative and exemplary 300 voltage pulses have been executed during the current therapy. If, according to step 812, 300 voltage pulses are determined to have been executed, the IVL control system stops the procedure, allowing no further voltage pulse generation. On the other hand, if 300 voltage pulses have not been executed, then the IVL control system instructs another series of voltage pulses to be executed and at the predetermined upper voltage threshold target magnitude.

In certain embodiments, the devices, systems and methods described herein may comprise 1 pulse/second, 2 pulses/second or 3 pulses/second. In some embodiments, the pulses/second generated by the described embodiments may be within the range of 1 to 5 pulses/second.

Embodiments of the present invention may comprise or utilize a special purpose or general-purpose computer including computer hardware, as discussed in greater detail below. Embodiments within the scope of the present invention also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: physical computer-readable storage media and transmission computer-readable media.

Physical computer-readable storage media includes RAM, ROM, EEPROM, CD-ROM or other optical disk storage (such as CDs, DVDs, etc.), magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (e.g., a "NIC"), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general-purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

The functionality described herein can be performed, at least in part, by one or more hardware logic components. For example, and without limitation, illustrative types of hardware logic components that can be used include Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

The present invention may be embodied in other specific forms without departing from its characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

EXEMPLARY EMBODIMENTS

The following non-limiting and exemplary embodiments are supported by the present disclosure.

Exemplary Embodiment Set 1

1. An intravascular lithotripsy system comprising:
   - at least one set of electrodes for arrangement within a body lumen while disposed within an inflatable balloon;
   - an electric pulse generation system for providing electrical energy to the at least one set of electrode to generate spark for intravascular lithotripsy (IVL) therapy, the electric pulse generation system including an IVL control system comprising a processor for executing instructions stored on a memory, and circuitry configured for communication of signals based on operation of the processor, the IVL control system configured to:
   - generate an initial series of voltage pulses to the at least one set of electrodes, wherein the magnitude of each voltage pulse in the initial series of voltage pulses comprises a target voltage that is set at a predetermined lower voltage magnitude threshold,
   - determine whether a threshold parameter is achieved, and
   - responsive to determination that the threshold parameter is not achieved, increase the voltage magnitude by a predetermined amount, and
   - generate another series of voltage pulses at the increased voltage magnitude for application to the at least one set of electrodes.

2. The intravascular lithotripsy system of embodiment 1, wherein the IVL control system is configured to continue to determine whether a threshold parameter is achieved after each generated series of voltage pulses.

3. The intravascular lithotripsy system of embodiment 2, wherein the threshold parameter comprises a predetermined upper voltage magnitude threshold.

4. The intravascular lithotripsy system of embodiment 3, wherein the IVL control system is configured to determine if the number of voltage pulses generated does not exceed a predetermined maximum number of voltage pulses.

5. The intravascular lithotripsy system of embodiment 3, wherein the predetermined maximum number of voltage pulses is within a range of 10 to 300 voltage pulses.

6. The intravascular lithotripsy system of embodiment 4, wherein if the IVL control system is configured to determine that the predetermined number of voltage pulses have not been generated, and if the predetermined number of voltage pulses have not been generated, then the IVL control system is further configured to execute another series of voltage pulses at the predetermined upper voltage magnitude threshold.

7. The intravascular lithotripsy system of embodiment 4, wherein if the IVL control system determines that the predetermined number of voltage pulses have been generated, then no further voltage pulses are executed.

8. The intravascular lithotripsy system of any one of embodiments 1-7, wherein the IVL control system is configured to define an acceptable voltage magnitude window comprising the predetermined lower voltage magnitude threshold and the predetermined upper voltage magnitude threshold.

9. The intravascular lithotripsy system, wherein the acceptable voltage magnitude window is different for balloons of different outer diameters.

10. The intravascular lithotripsy system of embodiment 9, wherein the predetermined lower voltage magnitude threshold is about 2500V for balloons having an outer diameter of 2.5 mm.

11. The intravascular lithotripsy system of embodiment 9, wherein the predetermined lower voltage magnitude threshold comprises about 2500V for balloons having an outer diameter of 3.0 mm.

12. The intravascular lithotripsy system of embodiment 9, wherein the predetermined lower voltage magnitude threshold comprises about 2500V for balloons having an outer diameter of 3.5 mm.

13. The intravascular lithotripsy system of embodiment 9, wherein the predetermined lower voltage magnitude threshold comprises about 2500V for balloons having an outer diameter of 4.0 mm.

14. The intravascular lithotripsy system of embodiment 9, wherein the predetermined lower voltage magnitude threshold is about 3000V for balloons having an outer diameter of 2.5 mm.

15. The intravascular lithotripsy system of embodiment 9, wherein the predetermined lower voltage magnitude threshold comprises about 3000V for balloons having an outer diameter of 3.0 mm.

16. The intravascular lithotripsy system of embodiment 9, wherein the predetermined lower voltage magnitude threshold comprises about 3000V for balloons having an outer diameter of 3.5 mm.

17. The intravascular lithotripsy system of embodiment 9, wherein the predetermined lower voltage magnitude threshold comprises about 3000V for balloons having an outer diameter of 4.0 mm.

18. The intravascular lithotripsy system of embodiment 9, wherein the predetermined lower voltage magnitude threshold is less than about 3000V for balloons having an outer diameter of 2.0 mm.

19. The intravascular lithotripsy system of embodiment 9, wherein the predetermined upper voltage magnitude threshold is less than about 3000V for balloons having an outer diameter of 2.5 mm.

20. The intravascular lithotripsy system of embodiment 9, wherein the predetermined lower voltage magnitude threshold is less than about 3000V for balloons having an outer diameter of 3.0 mm.

21. The intravascular lithotripsy system of embodiment 9, wherein the predetermined lower voltage magnitude threshold is less than about 3000V for balloons having an outer diameter of 3.5 mm.

22. The intravascular lithotripsy system of embodiment 9, wherein the predetermined lower voltage magnitude threshold is less than about 3000V for balloons having an outer diameter of 4.0 mm.

23. The intravascular lithotripsy system of embodiment 9, wherein the predetermined upper voltage magnitude threshold is greater than about 3000V for balloons having an outer diameter of 2.5 mm.

24. The intravascular lithotripsy system of embodiment 9, wherein the predetermined lower voltage magnitude threshold is greater than about 3000V for balloons having an outer diameter of 3.0 mm.

25. The intravascular lithotripsy system of embodiment 9, wherein the predetermined lower voltage magnitude threshold is greater than about 3000V for balloons having an outer diameter of 3.5 mm.

26. The intravascular lithotripsy system of embodiment 9, wherein the predetermined lower voltage magnitude threshold is greater than about 3000V for balloons having an outer diameter of 4.0 mm.

27. The intravascular lithotripsy system of any one of embodiments 9 to 26, wherein the predetermined upper voltage magnitude threshold is greater than about 3250V for balloons having an outer diameter of 2.5 mm.

28. The intravascular lithotripsy system of any one of embodiments 9 to 26, wherein the predetermined upper voltage magnitude threshold is greater than about 3250V for balloons having an outer diameter of 3.0 mm.

29. The intravascular lithotripsy system of any one of embodiments 9-26, wherein the predetermined upper voltage magnitude threshold is greater than about 3250V for balloons having an outer diameter of 3.5 mm.

30. The intravascular lithotripsy system of any one of embodiments 9-26, wherein the predetermined upper voltage magnitude threshold is greater than about 3250V for balloons having an outer diameter of 4.0 mm.

31. The intravascular lithotripsy system of any one of the embodiments 1-30, wherein the IVL control system is configured to determine whether the target voltage is not at the predetermined upper voltage magnitude target for a prior executed series of voltage pulses, and to increase the target voltage magnitude by a predetermined amount when the target voltage is determined to not be at the predetermined upper voltage magnitude target.

32. The intravascular lithotripsy system of embodiment 31, wherein the predetermined amount of voltage magnitude increase is within the range of 1 to 250V.

33. The intravascular lithotripsy system of any one of the embodiments 1-32, wherein the target voltage magnitude is increased by 25V when the target voltage is not at the predetermined upper voltage magnitude target for a prior executed series of voltage pulses.

34. The intravascular lithotripsy system of any one of the embodiments 1-32, wherein the target voltage magnitude is increased by more than 25V when the target voltage is not at the predetermined upper voltage magnitude target for a prior executed series of voltage pulses.

35. The intravascular lithotripsy system of any one of the embodiments 1-32, wherein the target voltage magnitude is increased by less than 25V when the target voltage is not at the predetermined upper voltage magnitude target for a prior executed voltage pulse.

36. The intravascular lithotripsy system of any one of the embodiments 1-32, wherein the target voltage magnitude is increased by 25V when the target voltage is not at the predetermined upper voltage magnitude target for a prior executed voltage pulse.

37. The intravascular lithotripsy system of any one of the embodiments 1-32, wherein the target voltage magnitude is increased by more than 25V when the target voltage is not at the predetermined upper voltage magnitude target for a prior executed voltage pulse.

38. The intravascular lithotripsy system of any one of the embodiments 1-32, wherein the target voltage magnitude is increased by less than 25V when the target voltage is not at the predetermined upper voltage magnitude target for a prior executed voltage pulse.

39. The intravascular lithotripsy system of any of the embodiments 1-38, wherein the pressure output over the predetermined maximum number of voltage pulses does not decay or decrease on average more than 0.25 Mpa.

40. The intravascular lithotripsy system of any of the embodiments 1-38, wherein the pressure output across a range of 10 to 300 voltage pulses does not decay or decrease on average more than 0.25 MPa.

41. The intravascular lithotripsy system of any of the embodiments 1-38, wherein the pressure output of the last voltage pulse of the predetermined maximum number of voltage pulses is greater than the pressure output of the first voltage pulse.

42. The intravascular lithotripsy system of any of the embodiments 1-41, wherein a slope of the pressure output of the voltage pulses increases over time.

43. The intravascular lithotripsy system of any of the embodiments 1-40, wherein a slope of the pressure output of the voltage pulses decreases over time.

44. The intravascular lithotripsy system of any of the embodiments 1-40, wherein a slope of the pressure output of the voltage pulses indicates a constant pressure magnitude output across the voltage pulses.

45. The intravascular lithotripsy system of any of the embodiments 1-44, wherein a plurality of a series of voltage pulses are generated.

46. The intravascular lithotripsy system of any of the embodiments 1-45, wherein one or more of the series of voltage pulses comprises 10 voltage pulses.

47. The intravascular lithotripsy system of any of the embodiments 1-45, wherein one or more of the series of voltage pulses comprises more than 10 voltage pulses.

48. The intravascular lithotripsy system of any of the embodiments 1-45, wherein one or more of the series of voltage pulses comprises less than 10 voltage pulses.

49. A method for generating and controlling voltage pulses, comprising:

providing a device according to any one of the embodiments 1-48;

determining the outer diameter of the device's balloon;

establishing an acceptable voltage pulse window comprising a predetermined lower voltage magnitude threshold and a predetermined upper voltage magnitude threshold;

executing a first series of voltage pulses at the predetermined lower voltage magnitude threshold;

increasing the voltage magnitude target by a predetermined amount and execute another series of voltage pulses at the increased voltage magnitude target;

continuing to sequentially increase the voltage magnitude target and executing of a related series of voltage pulses at the sequentially increased voltage magnitude target until the voltage magnitude target equals the predetermined upper voltage magnitude threshold;

determining that a predetermined number of voltage pulses have not been executed; and continuing executing one or more series of voltage pulses at the upper voltage magnitude threshold until it is determined that predetermined number of voltage pulses have been executed; and stopping the executing of the voltage pulses.

50. A method for generating and controlling voltage pulses, comprising:

providing a device according to any one of the embodiments 1-48;

determining the outer diameter of the device's balloon;

establishing an acceptable voltage pulse window comprising a predetermined lower voltage magnitude threshold and a predetermined upper voltage magnitude threshold;

executing a first series of voltage pulses at the predetermined lower voltage magnitude threshold;

increasing the voltage magnitude target by a predetermined amount and execute another series of voltage pulses at the increased voltage magnitude target;

continuing to sequentially increase the voltage magnitude target and executing of a related series of voltage pulses at the sequentially increased voltage magnitude target until the voltage magnitude target equals the predetermined upper voltage magnitude threshold;

determining that a predetermined number of voltage pulses have been executed; and stopping the executing of the voltage pulses.

51. A method for generating and controlling voltage pulses that produce pressure output that is stable and substantially constant, comprising:

providing a device according to any one of the embodiments 1-48;

determining the outer diameter of the device's balloon;

establishing an acceptable voltage pulse window comprising a predetermined lower voltage magnitude threshold and a predetermined upper voltage magnitude threshold;

executing a first series of voltage pulses at the predetermined lower voltage magnitude threshold;

increasing the voltage magnitude target by a predetermined amount and execute another series of voltage pulses at the increased voltage magnitude target;

continuing to sequentially increase the voltage magnitude target and executing of a related series of voltage pulses at the sequentially increased voltage magnitude target until the voltage magnitude target equals the predetermined upper voltage magnitude threshold; and producing a pressure output for each voltage pulse comprising a magnitude that is stable and substantially constant.

52. The method of embodiment 51, wherein the pressure output is generated over 10 to at least 300 voltage pulses.

53. A method for generating and controlling voltage pulses that produce pressure output that increases from the first voltage pulse to the last voltage pulse, comprising:

providing a device according to any one of the embodiments 1-48;

determining the outer diameter of the device's balloon;

establishing an acceptable voltage pulse window comprising a predetermined lower voltage magnitude threshold and a predetermined upper voltage magnitude threshold;

executing a first series of voltage pulses at the predetermined lower voltage magnitude threshold;

increasing the voltage magnitude target by a predetermined amount and execute another series of voltage pulses at the increased voltage magnitude target;

continuing to sequentially increase the voltage magnitude target and executing of a related series of voltage pulses at the sequentially increased voltage magnitude target until the voltage magnitude target equals the predetermined upper voltage magnitude threshold; and producing a pressure output for each voltage pulse comprising a magnitude that increases from the first voltage pulse to the last voltage pulse.

54. The method of embodiment 53, wherein the pressure output is generated over 10 to at least 300 voltage pulses.

55. The method of any one of embodiments 49-54, wherein the voltage pulses are generated at a frequency that is within the range of 1 to 5 pulses/second.

56. The method of embodiment 55, wherein the voltage pulse frequency comprises 2 pulses/second.

57. The method of embodiment 55, wherein the voltage pulse frequency comprises 3 pulses/second.

58. The method of any one of embodiments 49-57, wherein the pressure output of a first balloon comprising an outer diameter is not smaller than the pressure output of a second balloon comprising an outer diameter that is smaller than the outer diameter of the first balloon.

Exemplary Embodiment Set 2

1. An intravascular lithotripsy system with controlled stable and constant pressure output across a series of voltage pulses, comprising:

at least one set of spaced-apart electrodes for arrangement within a body lumen while disposed within a fluid-fillable member configured to contain conductive fluid therein;

an electric pulse generation system for providing electrical energy to the at least one set of spaced-apart electrodes to generate a plurality of pressure waves for intravascular lithotripsy (IVL) therapy, the electric pulse generation system including an IVL control system comprising a processor configured to execute instructions stored on a memory, and circuitry configured to communicate signals based on operation of the processor, the IVL control system configured to:

generate an initial plurality of voltage pulses comprising an initial series of voltage pulses to the at least one set of spaced-apart electrodes, wherein the magnitude of each voltage pulse in the initial series of voltage pulses comprises a target voltage that is initially set at a predetermined lower voltage magnitude threshold, wherein more than one of the generated plurality of voltage pulses produce a pressure wave, generate one or more subsequent series of voltage pulses, each subsequent series comprising a plurality of voltage pulses, wherein the target voltage for each subsequent series of voltage pulses is increased by a predetermined amount, wherein each one of the plurality of the produced pressure waves comprises a pressure magnitude output, and wherein the IVL control system is configured to control the pressure magnitude output for the plurality of pressure waves such that the pressure magnitude output does not decay or decrease on average more than a predetermined amount across the plurality of pressure waves.

2. An intravascular lithotripsy system with controlled stable and constant pressure output across a series of voltage pulses, comprising:

at least one set of spaced-apart electrodes for arrangement within a body lumen while disposed within a fluid-fillable member configured to contain conductive fluid therein;

an electric pulse generation system for providing electrical energy to the at least one set of electrode to generate a plurality of pressure waves for intravascular lithotripsy (IVL) therapy, the electric pulse generation system including an IVL control system comprising a processor configured to execute instructions stored on a memory, and circuitry configured to communicate signals based on operation of the processor, the IVL control system configured to:

generate an initial plurality of voltage pulses comprising an initial series of voltage pulses to the at least one set of spaced-apart electrodes, wherein the magnitude of each voltage pulse in the initial series of voltage pulses comprises a target voltage that is initially set at a predetermined lower voltage magnitude threshold, wherein more than one of the generated plurality of voltage pulses produce a pressure wave, generate one or more subsequent series of voltage pulses, each subsequent series comprising a plurality of voltage pulses, wherein the target voltage for each subsequent series of voltage pulses is increased by a predetermined amount, wherein each one of the plurality of the produced pressure waves comprises a pressure magnitude output, and wherein the IVL control system is configured to control the target voltage such that the pressure magnitude output does not decay or decrease on average more than a predetermined amount across the plurality of pressure waves.

3. A method for generating and controlling voltage pulses that produce controlled pressure output that is stable and substantially constant across a series of voltage pulses in an intravascular lithotripsy system, comprising:

providing an intravascular lithotripsy system according to embodiment 2;

determining the outer diameter of the intravascular lithotripsy system's balloon;

establishing an acceptable voltage pulse window comprising a predetermined lower voltage magnitude threshold and a predetermined upper voltage magnitude threshold;

executing a first series of voltage pulses at the predetermined lower voltage magnitude threshold;

increasing the voltage magnitude target by a predetermined amount and execute another series of voltage pulses at the increased voltage magnitude target;

continuing to sequentially increase the voltage magnitude target and executing of a related series of voltage pulses at the sequentially increased voltage magnitude target until the voltage magnitude target equals the predetermined upper voltage magnitude threshold; and producing a plurality of pressure waves, each pressure wave comprising a pressure output comprising a pressure magnitude that is controlled to not decay or decrease on average more than a predetermined amount across the plurality of pressure waves.

4. An intravascular lithotripsy system with controlled pressure output magnitude across a series of voltage pulses, comprising:

at least one set of spaced-apart electrodes for arrangement within a body lumen while disposed within a fluid-fillable member configured to contain conductive fluid therein;

an electric pulse generation system for providing electrical energy to the at least one set of spaced-apart electrodes to generate a plurality of pressure waves for intravascular lithotripsy (IVL) therapy, the electric pulse generation system including an IVL control system comprising a processor configured to execute instructions stored on a memory, and circuitry configured to communicate signals based on operation of the processor, the IVL control system configured to:

generate an initial plurality of voltage pulses comprising an initial series of voltage pulses to the at least one set of spaced-apart electrodes, wherein the magnitude of each voltage pulse in the initial series of voltage pulses comprises a target voltage that is initially set at a predetermined lower voltage magnitude threshold, wherein more than one of the generated plurality of voltage pulses produce a pressure wave, generate one or more subsequent series of voltage pulses, each subsequent series comprising a plurality of voltage pulses, wherein the target voltage for each subsequent series of voltage pulses is increased by a predetermined amount, wherein each one of the plurality of the produced pressure waves comprises a pressure magnitude output, and wherein the IVL control system is configured to control the pressure magnitude output within predetermined upper and lower threshold magnitudes across the plurality of pressure waves.

5. An intravascular lithotripsy system with controlled pressure output magnitude across a series of voltage pulses, comprising:

at least one set of spaced-apart electrodes for arrangement within a body lumen while disposed within a fluid-fillable member configured to contain conductive fluid therein;

an electric pulse generation system for providing electrical energy to the at least one set of spaced-apart electrodes to generate a plurality of pressure waves for intravascular lithotripsy (IVL) therapy, the electric pulse generation system including an IVL control system comprising a processor configured to execute instructions stored on a memory, and circuitry configured to communicate signals based on operation of the processor, the IVL control system configured to:

generate an initial plurality of voltage pulses comprising an initial series of voltage pulses to the at least one set of spaced-apart electrodes, wherein the magnitude of each voltage pulse in the initial series of voltage pulses comprises a target voltage that is initially set at a predetermined lower voltage magnitude threshold, wherein more than one of the generated plurality of voltage pulses produce a pressure wave, generate one or more subsequent series of voltage pulses, each subsequent series comprising a plurality of voltage pulses, wherein the target voltage for each subsequent series of voltage pulses is increased by a predetermined amount, wherein each one of the plurality of the produced pressure waves comprises a pressure magnitude output, and wherein the IVL control system is configured to control the target voltage within predetermined upper and lower thresholds, and further configured to control the resulting pressure wave output within predetermined upper and lower threshold magnitudes across the plurality of pressure waves.

6. A method for controlling pressure output magnitude across a series of voltage pulses generated by an intravascular lithotripsy system, comprising:

providing an intravascular lithotripsy system according to embodiment 5, wherein the fluid-filled member comprises a balloon;

determining the outer diameter of the intravascular lithotripsy system's balloon;

establishing an acceptable voltage pulse window comprising a predetermined lower voltage magnitude threshold and a predetermined upper voltage magnitude threshold;

executing a first series of voltage pulses at the predetermined lower voltage magnitude threshold;

increasing the voltage magnitude target by a predetermined amount and execute another series of voltage pulses at the increased voltage magnitude target;

continuing to sequentially increase the voltage magnitude target and executing of a related series of voltage pulses at the sequentially increased voltage magnitude target until the voltage magnitude target equals the predetermined upper voltage magnitude threshold; and producing a plurality of pressure waves, each pressure wave comprising a pressure output comprising a pressure magnitude that is controlled to not decay or decrease such that the pressure output across the plurality of pressure waves remains above a predetermined pressure magnitude.

7. An intravascular lithotripsy system with controlled pressure output across a plurality of voltage pulses, comprising:

at least one set of spaced-apart electrodes for arrangement within a body lumen while disposed within a fluid-fillable member configured to contain conductive fluid therein;

an electric pulse generation system for providing electrical energy to the at least one set of spaced-apart electrodes to generate a plurality of pressure waves for intravascular lithotripsy (IVL) therapy, the electric pulse generation system including an IVL control system comprising a processor configured to execute instructions stored on a memory, and circuitry configured to communicate signals based on operation of the processor, the IVL control system configured to:

generate an initial plurality of voltage pulses to the at least one set of electrodes, wherein the magnitude of each voltage pulse in the initial series of voltage pulses comprises a target voltage that is initially set at a predetermined lower voltage magnitude threshold, wherein more than one of the generated plurality of voltage pulses produce a pressure wave, determine that a predetermined maximum number of voltage pulses have not been executed, and when the predetermined maximum number of voltage pulses have been determined to not have been executed, sequentially increase the target voltage a predetermined amount and executing related series of voltage pulses until the target voltage is determined to meet a predetermined upper voltage threshold and/or the predetermined maximum number of voltage pulses is determined to have been executed, wherein each one of the plurality of the produced pressure waves comprises a pressure magnitude output, wherein the IVL control system is configured to control the pressure magnitude output within a predetermined upper and lower pressure magnitude threshold magnitudes across the plurality of pressure waves, and terminate the execution of voltage pulses when the predetermined maximum number of voltage pulses have been determined to have been executed.

8. A method for generating and controlling voltage pulses that produce controlled pressure output that is stable and substantially constant across a series of voltage pulses in an intravascular lithotripsy system, comprising:

providing an intravascular lithotripsy system according to embodiment 1, wherein the fluid-filled member comprises a balloon;

determining the outer diameter of the intravascular lithotripsy system's balloon;

establishing an acceptable voltage pulse window comprising a predetermined lower voltage magnitude threshold and a predetermined upper voltage magnitude threshold;

executing a first series of voltage pulses at the predetermined lower voltage magnitude threshold;

increasing the voltage magnitude target by a predetermined amount and execute another series of voltage pulses at the increased voltage magnitude target;

continuing to sequentially increase the voltage magnitude target and executing of a related series of voltage pulses at the sequentially increased voltage magnitude target until the voltage magnitude target equals the predetermined upper voltage magnitude threshold;

producing a plurality of pressure waves, each pressure wave comprising a pressure output comprising a pressure magnitude that is controlled within upper and lower pressure magnitude threshold magnitudes across the plurality of pressure waves;

determining that a predetermined maximum number of voltage pulses have been executed; and terminating the executing of the voltage pulses.

9. An intravascular lithotripsy system comprising controlled increasing pressure output, comprising:

at least one set of spaced-apart electrodes for arrangement within a body lumen while disposed within a fluid-fillable member configured to contain conductive fluid therein;

an electric pulse generation system for providing electrical energy to the at least one set of spaced-apart electrodes to generate a plurality of pressure waves for intravascular lithotripsy (IVL) therapy, the electric pulse generation system including an IVL control system comprising a processor configured to execute instructions stored on a memory, and circuitry configured to communicate signals based on operation of the processor, the IVL control system configured to:

generate an initial plurality of voltage pulses comprising an initial series of voltage pulses to the at least one set of spaced-apart electrodes, wherein the magnitude of each voltage pulse in the initial series of voltage pulses comprises a target voltage that is initially set at a predetermined lower voltage magnitude threshold, wherein more than one of the generated plurality of voltage pulses produce a pressure wave, generate one or more subsequent series of voltage pulses, each subsequent series comprising a plurality of voltage pulses, wherein the target voltage for each subsequent series of voltage pulses is increased by a predetermined amount, wherein each one of the plurality of the produced pressure waves comprises a pressure magnitude output, and wherein the IVL control system is configured to control the pressure magnitude output for the plurality of pressure waves such that the pressure magnitude output increases across the plurality of pressure waves.

10. An intravascular lithotripsy system comprising controlled increasing pressure output across a series of voltage pulses, comprising:

at least one set of electrodes for arrangement within a body lumen while disposed within a fluid-fillable member configured to contain conductive fluid therein;

an electric pulse generation system for providing electrical energy to the at least one set of spaced-apart electrodes to generate a plurality of pressure waves for intravascular lithotripsy (IVL) therapy, the electric pulse generation system including an IVL control system comprising a processor for executing instructions stored on a memory, and circuitry configured for communication of signals based on operation of the processor, the IVL control system configured to:

generate an initial plurality of voltage pulses comprising an initial series of voltage pulses to the at least one set of spaced-apart electrodes, wherein the magnitude of each voltage pulse in the initial series of voltage pulses comprises a target voltage that is initially set at a predetermined lower voltage magnitude threshold, wherein more than one of the generated plurality of voltage pulses produce a pressure wave, generate one or more subsequent series of voltage pulses, each subsequent series comprising a plurality of voltage pulses, wherein the target voltage for each subsequent series of voltage pulses is increased by a predetermined amount, wherein each one of the plurality of the produced pressure waves comprises a pressure magnitude output, and wherein the IVL control system is configured to control the target voltage such that the pressure magnitude output is controlled to increase within a predetermined pressure magnitude window across the plurality of pressure waves.

11. A method for generating and controlling voltage pulses that produce controlled increasing pressure output in an intravascular lithotripsy system, comprising:

providing an intravascular lithotripsy system according to embodiment 2, wherein the fluid-filled member comprises a balloon;

determining the outer diameter of the intravascular lithotripsy system's balloon;

establishing an acceptable voltage pulse window comprising a predetermined lower voltage magnitude threshold and a predetermined upper voltage magnitude threshold;

executing a first series of more than one voltage pulses at the predetermined lower voltage magnitude threshold;

increasing the voltage magnitude target by a predetermined amount and execute another series of voltage pulses at the increased voltage magnitude target;

continuing to sequentially increase the voltage magnitude target and executing of a related series of voltage pulses at the sequentially increased voltage magnitude target until the voltage magnitude target equals the predetermined upper voltage magnitude threshold; and producing a plurality of pressure waves, each pressure wave comprising a pressure output comprising a pressure magnitude that is controlled to increase across the plurality of pressure waves.

12. An intravascular lithotripsy system producing controlled decreasing pressure output, comprising:

at least one set of spaced-apart electrodes for arrangement within a body lumen while disposed within a fluid-fillable member configured to contain conductive fluid therein;

an electric pulse generation system for providing electrical energy to the at least one set of spaced-apart electrodes to generate a plurality of pressure waves for intravascular lithotripsy (IVL) therapy, the electric pulse generation system including an IVL control system comprising a processor configured to execute instructions stored on a memory, and circuitry configured to communicate signals based on operation of the processor, the IVL control system configured to:

generate an initial plurality of voltage pulses comprising an initial series of voltage pulses to the at least one set of spaced-apart electrodes, wherein the magnitude of each voltage pulse in the initial series of voltage pulses comprises a target voltage that is initially set at a predetermined lower voltage magnitude threshold, wherein more than one of the generated plurality of voltage pulses produce a pressure wave, generate one or more subsequent series of voltage pulses, each subsequent series comprising a plurality of voltage pulses, wherein the target voltage for each subsequent series of voltage pulses is increased by a predetermined amount, wherein each one of the plurality of the produced pressure waves comprises a pressure magnitude output, and wherein the IVL control system is configured to control the pressure magnitude output for the plurality of pressure waves such that the pressure magnitude output decays or decreases within a predetermined pressure magnitude window across the plurality of pressure waves.

13. An intravascular lithotripsy system producing controlled decreasing pressure output across a series of voltage pulses, comprising:

at least one set of spaced-apart electrodes for arrangement within a body lumen while disposed within a fluid-fillable member configured to contain conductive fluid therein;

an electric pulse generation system for providing electrical energy to the at least one set of spaced-apart electrodes to generate a plurality of pressure waves for intravascular lithotripsy (IVL) therapy, the electric pulse generation system including an IVL control system comprising a processor for executing instructions stored on a memory, and circuitry configured for communication of signals based on operation of the processor, the IVL control system configured to:

generate an initial plurality of voltage pulses comprising an initial series of voltage pulses to the at least one set of electrodes, wherein the magnitude of each voltage pulse in the initial series of voltage pulses comprises a target voltage that is initially set at a predetermined lower voltage magnitude threshold, wherein more than one of the generated plurality of voltage pulses produce a pressure wave, generate one or more subsequent series of voltage pulses, each subsequent series comprising a plurality of voltage pulses, wherein the target voltage for each subsequent series of voltage pulses is increased by a predetermined amount, wherein each one of the plurality of the produced pressure waves comprises a pressure magnitude output, and wherein the IVL control system is configured to control the target voltage such that the pressure magnitude output decreases within a predetermined pressure magnitude window across the plurality of pressure waves.

14. A method for generating and controlling voltage pulses that produce controlled decreasing pressure output in an intravascular lithotripsy system, comprising:

providing an intravascular lithotripsy system according to embodiment 2, wherein the fluid-filled member comprises a balloon;

determining the outer diameter of the intravascular lithotripsy system's balloon;

establishing an acceptable voltage pulse window comprising a predetermined lower voltage magnitude threshold and a predetermined upper voltage magnitude threshold;

executing a first series of more than one voltage pulses at the predetermined lower voltage magnitude threshold;

increasing the voltage magnitude target by a predetermined amount and execute another series of voltage pulses at the increased voltage magnitude target;

continuing to sequentially increase the voltage magnitude target and executing of a related series of voltage pulses at the sequentially increased voltage magnitude target until the voltage magnitude target equals the predetermined upper voltage magnitude threshold; and producing a plurality of pressure waves, each pressure wave comprising a pressure output comprising a pressure magnitude that is controlled to decrease within a predetermined pressure magnitude window across the plurality of pressure waves.

Exemplary Embodiment Set 3

1. An IVL system comprising at least one set of spaced-apart electrodes for arrangement within a body lumen while disposed within a fluid-fillable member configured to contain conductive fluid therein;

an electric pulse generation system for providing electrical energy to the at least one set of spaced-apart electrodes to generate a plurality of pressure waves for intravascular lithotripsy (IVL) therapy, the electric pulse generation system including an IVL control system comprising a processor for executing instructions stored on a memory, and circuitry configured for communication of signals based on operation of the processor, the IVL control system configured to:

generate an initial plurality of voltage pulses comprising at least an initial series of voltage pulses to the at least one set of electrodes, wherein the magnitude of each voltage pulse in the initial series of voltage pulses comprises a target voltage that is initially set at a predetermined lower voltage magnitude threshold, wherein more than one of the generated plurality of voltage pulses produce a pressure wave, wherein the IVL control system is configured to control the pressure magnitude output across the plurality of pressure waves.

2. The IVL system of embodiment 1, wherein the IVL control system is configured to control the pressure magnitude output is controlled to not decay or decrease more than a predetermined amount across the plurality of pressure waves.

3. The IVL system of embodiment 2, wherein the IVL control system is configured to control the target voltage within predetermined upper and lower thresholds.

4. The IVL system of embodiment 1, wherein the IVL control system is configured to control the pressure magnitude output to remain above a predetermined lower threshold across the plurality of pressure waves.

5. The IVL system of embodiment 4, wherein the IVL control system is configured to control the target voltage within predetermined upper and lower thresholds.

6. The IVL system of embodiment 1, wherein the IVL control system is configured to control the pressure magnitude output to remain within predetermined upper and lower thresholds across the plurality of pressure waves.

7. The IVL system of embodiment 6, wherein the IVL control system is configured to control the target voltage within predetermined upper and lower thresholds.

8. The IVL system of embodiment 1, wherein the IVL control system is configured to control the pressure magnitude output to remain at a substantially constant magnitude across the plurality of pressure waves.

9. The IVL system of embodiment 8, wherein the IVL control system is configured to control the target voltage within predetermined upper and lower thresholds.

10. The IVL system of embodiment 1, wherein the IVL control system is configured to control the pressure magnitude output is controlled to not increase more than a predetermined amount across the plurality of pressure waves.

11. The IVL system of embodiment 10, wherein the IVL control system is configured to control the target voltage within predetermined upper and lower thresholds.

12. The IVL system of embodiment 1, wherein the IVL control system is further configured to terminate the execution of voltage pulses when the predetermined maximum number of voltage pulses have been determined to be executed.

Exemplary Embodiment Set 4

1. An intravascular lithotripsy system comprising:

at least one set of electrodes for arrangement within a body lumen while disposed within a fluid-fillable member configured to contain conductive fluid therein;

an electric pulse generation system for providing electrical energy to the at least one set of electrode to generate spark for intravascular lithotripsy (IVL) therapy, the electric pulse generation system including an IVL control system comprising a processor for executing instructions stored on a memory, and circuitry configured for communication of signals based on operation of the processor, the IVL control system configured to:

generate an initial series of voltage pulses to the at least one set of electrodes, wherein the magnitude of each voltage pulse in the initial series of voltage pulses comprises a target voltage that is set at a predetermined lower voltage magnitude threshold, determine whether a threshold parameter is achieved, and responsive to determination that the threshold parameter is not achieved, increase the voltage magnitude by a predetermined amount, and generate another series of voltage pulses at the increased voltage magnitude for application to the at least one set of electrodes.

2. The intravascular lithotripsy system of embodiment 1, wherein the IVL control system is configured to continue to determine whether a threshold parameter is achieved after each generated series of voltage pulses.

3. The intravascular lithotripsy system of embodiment 2, wherein the threshold parameter comprises a predetermined upper voltage magnitude threshold.

4. The intravascular lithotripsy system of embodiment 3, wherein the IVL control system is configured to determine if the number of voltage pulses generated does not exceed a predetermined maximum number of voltage pulses.

5. The intravascular lithotripsy system of embodiment 3, wherein the predetermined maximum number of voltage pulses is within a range of 10 to 300 voltage pulses.

6. The intravascular lithotripsy system of embodiment 4, wherein if the IVL control system is configured to determine that the predetermined number of voltage pulses have not been generated, and if the predetermined number of voltage pulses have not been generated, then the IVL control system is further configured to execute another series of voltage pulses at the predetermined upper voltage magnitude threshold.

7. The intravascular lithotripsy system of embodiment 4, wherein if the IVL control system determines that the predetermined number of voltage pulses have been generated, then no further voltage pulses are executed.

8. The intravascular lithotripsy system of any one of embodiments 1-7, wherein the IVL control system is configured to define an acceptable voltage magnitude window comprising the predetermined lower voltage magnitude threshold and the predetermined upper voltage magnitude threshold.

9. The intravascular lithotripsy system of embodiment 8, wherein the acceptable voltage magnitude window is different for balloons of different outer diameters.

10. The intravascular lithotripsy system of embodiment 9, wherein the predetermined lower voltage magnitude threshold is about 2500V for balloons having an outer diameter of 2.5 mm.

11. The intravascular lithotripsy system of embodiment 9, wherein the predetermined lower voltage magnitude threshold comprises about 2500V for balloons having an outer diameter of 3.0 mm.

12. The intravascular lithotripsy system of embodiment 9, wherein the predetermined lower voltage magnitude threshold comprises about 2500V for balloons having an outer diameter of 3.5 mm.

13. The intravascular lithotripsy system of embodiment 9, wherein the predetermined lower voltage magnitude threshold comprises about 2500V for balloons having an outer diameter of 4.0 mm.

14. The intravascular lithotripsy system of embodiment 9, wherein the predetermined lower voltage magnitude threshold is about 3000V for balloons having an outer diameter of 2.5 mm.

15. The intravascular lithotripsy system of embodiment 9, wherein the predetermined lower voltage magnitude threshold comprises about 3000V for balloons having an outer diameter of 3.0 mm.

16. The intravascular lithotripsy system of embodiment 9, wherein the predetermined lower voltage magnitude threshold comprises about 3000V for balloons having an outer diameter of 3.5 mm.

17. The intravascular lithotripsy system of embodiment 9, wherein the predetermined lower voltage magnitude threshold comprises about 3000V for balloons having an outer diameter of 4.0 mm.

18. The intravascular lithotripsy system of embodiment 9, wherein the predetermined lower voltage magnitude threshold is less than about 3000V for balloons having an outer diameter of 2.0 mm.

19. The intravascular lithotripsy system of embodiment 9, wherein the predetermined upper voltage magnitude threshold is less than about 3000V for balloons having an outer diameter of 2.5 mm.

20. The intravascular lithotripsy system of embodiment 9, wherein the predetermined lower voltage magnitude threshold is less than about 3000V for balloons having an outer diameter of 3.0 mm.

21. The intravascular lithotripsy system of embodiment 9, wherein the predetermined lower voltage magnitude threshold is less than about 3000V for balloons having an outer diameter of 3.5 mm.

22. The intravascular lithotripsy system of embodiment 9, wherein the predetermined lower voltage magnitude threshold is less than about 3000V for balloons having an outer diameter of 4.0 mm.

23. The intravascular lithotripsy system of embodiment 9, wherein the predetermined upper voltage magnitude threshold is greater than about 3000V for balloons having an outer diameter of 2.5 mm.

24. The intravascular lithotripsy system of embodiment 9, wherein the predetermined lower voltage magnitude threshold is greater than about 3000V for balloons having an outer diameter of 3.0 mm.

25. The intravascular lithotripsy system of embodiment 9, wherein the predetermined lower voltage magnitude threshold is greater than about 3000V for balloons having an outer diameter of 3.5 mm.

26. The intravascular lithotripsy system of embodiment 9, wherein the predetermined lower voltage magnitude threshold is greater than about 3000V for balloons having an outer diameter of 4.0 mm.

27. The intravascular lithotripsy system of any one of embodiments 9 to 26, wherein the predetermined upper voltage magnitude threshold is greater than about 3250V for balloons having an outer diameter of 2.5 mm.

28. The intravascular lithotripsy system of any one of embodiments 9 to 26, wherein the predetermined upper voltage magnitude threshold is greater than about 3250V for balloons having an outer diameter of 3.0 mm.

29. The intravascular lithotripsy system of any one of embodiments 9-26, wherein the predetermined upper voltage magnitude threshold is greater than about 3250V for balloons having an outer diameter of 3.5 mm.

30. The intravascular lithotripsy system of any one of embodiments 9-26, wherein the predetermined upper voltage magnitude threshold is greater than about 3250V for balloons having an outer diameter of 4.0 mm.

31. The intravascular lithotripsy system of any one of the embodiments 1-30, wherein the IVL control system is configured to determine whether the target voltage is not at the predetermined upper voltage magnitude target for a prior executed series of voltage pulses, and to increase the target voltage magnitude by a predetermined amount when the target voltage is determined to not be at the predetermined upper voltage magnitude target.

32. The intravascular lithotripsy system of embodiment 31, wherein the predetermined amount of voltage magnitude increase is within the range of 1 to 250V.

33. The intravascular lithotripsy system of any one of the embodiments 1-32, wherein the target voltage magnitude is increased by 25V when the target voltage is not at the predetermined upper voltage magnitude target for a prior executed series of voltage pulses.

34. The intravascular lithotripsy system of any one of the embodiments 1-32, wherein the target voltage magnitude is increased by more than 25V when the target voltage is not at the predetermined upper voltage magnitude target for a prior executed series of voltage pulses.

35. The intravascular lithotripsy system of any one of the embodiments 1-32, wherein the target voltage magnitude is increased by less than 25V when the target voltage is not at the predetermined upper voltage magnitude target for a prior executed voltage pulse.

36. The intravascular lithotripsy system of any one of the embodiments 1-32, wherein the target voltage magnitude is increased by 25V when the target voltage is not at the predetermined upper voltage magnitude target for a prior executed voltage pulse.

37. The intravascular lithotripsy system of any one of the embodiments 1-32, wherein the target voltage magnitude is increased by more than 25V when the target voltage is not at the predetermined upper voltage magnitude target for a prior executed voltage pulse.

38. The intravascular lithotripsy system of any one of the embodiments 1-32, wherein the target voltage magnitude is increased by less than 25V when the target voltage is not at the predetermined upper voltage magnitude target for a prior executed voltage pulse.

39. The intravascular lithotripsy system of any of the embodiments 1-38, wherein the pressure output over the predetermined maximum number of voltage pulses does not decay or decrease on average more than 0.25 Mpa.

40. The intravascular lithotripsy system of any of the embodiments 1-38, wherein the pressure output across a range of 10 to 300 voltage pulses does not decay or decrease on average more than 0.25 MPa.

41. The intravascular lithotripsy system of any of the embodiments 1-38, wherein the pressure output of the last voltage pulse of the predetermined maximum number of voltage pulses is greater than the pressure output of the first voltage pulse.

42. The intravascular lithotripsy system of any of the embodiments 1-41, wherein a slope of the pressure output of the voltage pulses increases over time.

43. The intravascular lithotripsy system of any of the embodiments 1-40, wherein a slope of the pressure output of the voltage pulses decreases over time.

44. The intravascular lithotripsy system of any of the embodiments 1-40, wherein a slope of the pressure output of the voltage pulses indicates a constant pressure magnitude output across the voltage pulses.

45. The intravascular lithotripsy system of any of the embodiments 1-44, wherein a plurality of a series of voltage pulses are generated.

46. The intravascular lithotripsy system of any of the embodiments 1-45, wherein one or more of the series of voltage pulses comprises 10 voltage pulses.

47. The intravascular lithotripsy system of any of the embodiments 1-45, wherein one or more of the series of voltage pulses comprises more than 10 voltage pulses.

48. The intravascular lithotripsy system of any of the embodiments 1-45, wherein one or more of the series of voltage pulses comprises less than 10 voltage pulses.

49. A method for generating and controlling voltage pulses, comprising:

providing a device according to any one of the embodiments 1-48, wherein the fluid-fillable member comprises a balloon;

determining the outer diameter of the device's balloon;

establishing an acceptable voltage pulse window comprising a predetermined lower voltage magnitude threshold and a predetermined upper voltage magnitude threshold;

executing a first series of voltage pulses at the predetermined lower voltage magnitude threshold;

increasing the voltage magnitude target by a predetermined amount and execute another series of voltage pulses at the increased voltage magnitude target;

continuing to sequentially increase the voltage magnitude target and executing of a related series of voltage pulses at the sequentially increased voltage magnitude target until the voltage magnitude target equals the predetermined upper voltage magnitude threshold;

determining that a predetermined number of voltage pulses have not been executed; and continuing executing one or more series of voltage pulses at the upper voltage magnitude threshold until it is determined that predetermined number of voltage pulses have been executed; and stopping the executing of the voltage pulses.

50. A method for generating and controlling voltage pulses, comprising:

providing a device according to any one of the embodiments 1-48, wherein the fluid-fillable member comprises a balloon;

determining the outer diameter of the device's balloon;

establishing an acceptable voltage pulse window comprising a predetermined lower voltage magnitude threshold and a predetermined upper voltage magnitude threshold;

executing a first series of voltage pulses at the predetermined lower voltage magnitude threshold;

increasing the voltage magnitude target by a predetermined amount and execute another series of voltage pulses at the increased voltage magnitude target;

continuing to sequentially increase the voltage magnitude target and executing of a related series of voltage pulses at the sequentially increased voltage magnitude target until the voltage magnitude target equals the predetermined upper voltage magnitude threshold;

determining that a predetermined number of voltage pulses have been executed; and stopping the executing of the voltage pulses.

51. A method for generating and controlling voltage pulses that produce pressure output that is stable and substantially constant, comprising:

providing a device according to any one of the embodiments 1-48, wherein the fluid-fillable member comprises a balloon;

determining the outer diameter of the device's balloon;

establishing an acceptable voltage pulse window comprising a predetermined lower voltage magnitude threshold and a predetermined upper voltage magnitude threshold;

executing a first series of voltage pulses at the predetermined lower voltage magnitude threshold;

increasing the voltage magnitude target by a predetermined amount and execute another series of voltage pulses at the increased voltage magnitude target;

continuing to sequentially increase the voltage magnitude target and executing of a related series of voltage pulses at the sequentially increased voltage magnitude target until the voltage magnitude target equals the predetermined upper voltage magnitude threshold; and producing a pressure output for each voltage pulse comprising a magnitude that is stable and substantially constant.

52. The method of embodiment 51, wherein the pressure output is generated over 10 to at least 300 voltage pulses.

53. A method for generating and controlling voltage pulses that produce pressure output that increases from the first voltage pulse to the last voltage pulse, comprising:

providing a device according to any one of the embodiments 1-48, wherein the fluid-fillable member comprises a balloon;

determining the outer diameter of the device's balloon;

establishing an acceptable voltage pulse window comprising a predetermined lower voltage magnitude threshold and a predetermined upper voltage magnitude threshold;

executing a first series of voltage pulses at the predetermined lower voltage magnitude threshold;

increasing the voltage magnitude target by a predetermined amount and execute another series of voltage pulses at the increased voltage magnitude target;

continuing to sequentially increase the voltage magnitude target and executing of a related series of voltage pulses at the sequentially increased voltage magnitude target until the voltage magnitude target equals the predetermined upper voltage magnitude threshold; and producing a pressure output for each voltage pulse comprising a magnitude that increases from the first voltage pulse to the last voltage pulse.

54. The method of embodiment 53, wherein the pressure output is generated over 10 to at least 300 voltage pulses.

55. The method of any one of embodiments 49-54, wherein the voltage pulses are generated at a frequency that is within the range of 1 to 5 pulses/second.

56. The method of embodiment 55, wherein the voltage pulse frequency comprises 2 pulses/second.

57. The method of embodiment 55, wherein the voltage pulse frequency comprises 3 pulses/second.

58. The method of any one of embodiments 49-57, wherein the pressure output of a first balloon comprising an outer diameter is not smaller than the pressure output of a second balloon comprising an outer diameter that is smaller than the outer diameter of the first balloon.

Exemplary Embodiment Set 5

An intravascular lithotripsy system comprising:

a catheter assembly comprising an elongate member defining a lumen and while disposed within a fluid-fillable member configured to contain conductive fluid therein located on a longitudinal region of the elongate member, the catheter assembly configured to inflate the fluid-fillable with the conductive fluid to facilitate IVL therapy; and at least one set of spaced-apart electrodes for arrangement within the fluid-fillable member for submerging within the IVL fluid medium;

wherein the IVL control system is configured to apply one or more voltage pulses to the at least one spaced-apart electrodes under initial control settings, to determine whether a threshold parameter comprising the maximum number of voltage pulses resulting in an electrical arc between the at least one set of spaced-apart electrodes is achieved under the initial control settings, and to increase at least one of pulse duration and voltage in response to determination that the threshold parameter is not achieved, wherein the IVL control system is configured to apply the increased at least one of pulse duration and voltage to the at least one set of spaced-apart electrodes.

2. An intravascular lithotripsy system comprising a catheter assembly comprising an elongate member defining a lumen and while disposed within a fluid-fillable member configured to contain conductive fluid therein located on a longitudinal region of the elongate member, the catheter assembly configured to inflate the fluid-fillable with the conductive fluid to facilitate IVL therapy; at least one set of spaced-apart electrodes for arrangement within the fluid-fillable member for submerging within the conductive fluid; and an IVL control system comprising a processor for executing instructions stored on memory and circuitry configured to communicate signals based on operation of the processor for providing IVL therapy to a patient, wherein the IVL control system is configured to generate and apply one or more voltage pulses to the at least one spaced-apart electrodes under initial control settings, to determine whether a threshold parameter comprising the maximum number of voltage pulses resulting in an electrical arc between the at least one set of spaced-apart electrodes is achieved under the initial control settings, and to increase at least one of pulse duration and voltage in response to determination that the threshold parameter is not achieved, wherein the IVL control system is configured to apply the increased at least one of pulse duration and voltage to the at least one set of spaced-apart electrodes, and wherein the IVL control system is configured to continue reapplying the increase at least one of pulse duration and voltage to the at least one spaced-apart set of electrodes after the determination that the threshold parameter is not achieved, and to terminate the generation of voltage pulses when the determination is made that the threshold parameter is achieved.

3. A method of operating an intravascular lithotripsy (IVL) system having a catheter assembly comprising an elongate member defining a lumen and a fluid-fillable member configured to contain conductive fluid and located at a distal region of the elongate member, the catheter assembly configured to inflate the fluid-fillable member with the conductive fluid to facilitate IVL therapy, at least one set of spaced-apart electrodes for arrangement within the fluid-fillable member for submerging within the IVL fluid medium, and an IVL control system comprising a processor configured to execute instructions stored on memory and communications circuitry configured to communicate signals based on operation of the processor for providing IVL therapy to a patient, the method comprising:

generating voltage pulses and applying the generated voltage pulses under initial electrical settings comprising voltage magnitude and duration of application of generated voltage to the at least one set of spaced-apart electrodes;

determining whether a predetermined maximum number of electrical arcs produced between the at least one set of spaced-apart electrodes is achieved under the initial electrical settings;

increasing at least one of pulse duration and voltage of the electrical settings in response to determination that the threshold parameter is not achieved; and terminating the generating of the voltage pulses in response to determination that the threshold parameter is achieved.

4. An intravascular lithotripsy system comprising:

at least one set of spaced-apart electrodes for arrangement within a body lumen while disposed within a fluid-fillable member configured to contain a conductive fluid;

an electric pulse generation system for providing controlled levels of electrical energy to the at least one set of spaced-apart electrodes to generate spark for intravascular lithotripsy (IVL) therapy, the electric pulse generation system including an IVL control system comprising a processor configured to execute instructions stored on memory and communications circuitry configured to communicate signals based on commands from the processor, the IVL control system including a charge control system for controlling electrical charging of a discharge system, wherein the charge control system is configured to provide controlled and variable electrical power to the discharge system at different voltage level for consecutive cycles of charge.

5. An intravascular lithotripsy system comprising:

at least one set of spaced-apart electrodes for arrangement within a body lumen while disposed within a fluid-fillable member configured to contain a conductive fluid;

an electric pulse generation system configured to provide controlled electrical energy levels to the at least one set of spaced-apart electrodes to generate spark for intravascular lithotripsy (IVL) therapy, the electric pulse generation system including an IVL control system comprising a processor configured to execute instructions stored on memory and communications circuitry configured to communicate signals based on commands from the processor, the IVL control system including a charge control system for controlling electrical charging of a discharge system, wherein the discharge system includes an energy storage system and the charge control system is configured to provide controlled variable voltage power to the discharge system at different voltage for consecutive cycles of charge after energy discharge from the energy storage system.

6. An intravascular lithotripsy system comprising:

at least one set of spaced-apart electrodes for arrangement within a body lumen while disposed within a fluid-fillable member configured to contain a conductive fluid;

an electric pulse generation system for providing electrical energy to the at least one set of spaced-apart electrodes to generate spark for intravascular lithotripsy (IVL) therapy, the electric pulse generation system including an IVL control system comprising a processor configured to execute instructions stored on memory and communications circuitry configured to communicate signals based on commands from the processor, wherein the IVL control system is configured to:

assess the stored energy state of an energy storage system of the IVL system to determine stored energy;

compare the assessed stored energy state against a stored threshold value;

deliver a voltage pulse to at least one set of spaced-apart electrodes of the IVL system;

assess the remaining energy state of the energy storage system of the IVL system to determine remaining energy; and compare the assessed remaining energy state against a stored threshold value.

7. A method of operating an intravascular lithotripsy system, the method comprising:

assessing the stored energy state of an energy storage system of an intravascular lithotripsy (IVL) system to determine stored energy;

delivering a voltage pulse to at least one set of electrodes of the IVL system;

assessing the remaining energy state of the energy storage system of the IVL system to determine remaining energy; and comparing at least one of the assessed energy states with a stored threshold value to determine the energy of the voltage pulse.

8. A method of operating an intravascular lithotripsy system including at least one set of spaced-apart electrodes, the method comprising:

assessing the stored energy state of an energy storage system of an intravascular lithotripsy (IVL) system to determine stored energy;

delivering a voltage pulse to at least one of the at least one set of spaced-apart electrodes of the IVL system;

assessing the remaining energy state of the energy storage system of the IVL system to determine remaining energy; and comparing at least one of the assessed energy states with a stored threshold value to determine the energy of the voltage pulse, wherein assessing the energy state to determine stored energy includes determining a voltage level of the energy storage system.

9. An intravascular lithotripsy system comprising:

at least one set of spaced-apart electrodes for arrangement within a body lumen while disposed within a fluid-fillable member configured to contain a conductive fluid;

an electric pulse generation system for providing electrical energy to the at least one set of spaced-apart electrodes to generate spark for intravascular lithotripsy (IVL) therapy, the electric pulse generation system including an IVL control system comprising a processor configured to execute instructions stored on memory and communications circuitry configured to communicate signals based on commands from the processor, wherein the electric pulse generation system comprises an electrical power system including an AC mains and a DC power storage system, wherein the AC mains are configured for connection with a AC power receptacle to receive AC power from infrastructure, and the DC power storage system is configured to receive AC power from the AC mains and to convert AC power to DC power for charging a DC power storage device of the DC power storage system, and wherein the electric pulse generation system is configured to selectively provide power from the AC mains or the DC power storage system for IVL operations.

10. A method for powering a intravascular lithotripsy system, comprising:

providing the intravascular lithotripsy system of embodiment 1;

selecting provision of power from the AC mains; and powering the intravascular lithotripsy system 11. An intravascular lithotripsy system comprising:

at least one set of electrodes for arrangement within a body lumen while disposed within a fluid-fillable member configured to contain a conductive fluid;

an electric pulse generation system for providing electrical energy to the at least one set of spaced-apart electrodes to generate spark for intravascular lithotripsy (IVL) therapy, the electric pulse generation system including an IVL control system comprising a processor configured to execute instructions stored on memory and communications circuitry configured to communicate signals based on commands from the processor, wherein the IVL control system is configured to:

assess the stored energy state of an energy storage system of the IVL system to determine stored energy;

deliver a voltage pulse to at least one set of electrodes of the IVL system;

assess the remaining energy state of the energy storage system of the IVL system to determine remaining energy; and compare the assessed energy states to determine the energy of the voltage pulse.

12. A method of operating an intravascular lithotripsy system, the method comprising:

assessing the stored energy state of an energy storage system of an intravascular lithotripsy (IVL) system to determine stored energy;

delivering a voltage pulse to at least one set of spaced-apart electrodes of the IVL system;

assessing the remaining energy state of the energy storage system of the IVL system to determine remaining energy; and comparing the energy states assessed to determine the energy of the voltage pulse.

13. A method of operating an intravascular lithotripsy system, the method comprising:

assessing the stored energy state of an energy storage system of an intravascular lithotripsy (IVL) system to determine stored energy;

delivering a voltage pulse to at least one set of spaced-apart electrodes of the IVL system;

assessing the remaining energy state of the energy storage system of the IVL system to determine remaining energy; and comparing the energy states assessed to determine the energy of the voltage pulse, wherein assessing the energy state to determine stored energy includes determining a voltage level of the energy storage system.

14. An intravascular lithotripsy system comprising:

at least one set of spaced-apart electrodes for arrangement within a body lumen while disposed within a fluid-fillable member configured to contain a conductive fluid;

an electric pulse generation system for providing electrical energy to the at least one set of spaced-apart electrodes to generate spark for intravascular lithotripsy (IVL) therapy, the electric pulse generation system including an IVL control system comprising a processor configured to execute instructions stored on memory and communications circuitry configured to communicate signals based on commands from the processor, wherein the IVL control system including an adjustable energy storage system configured to selective adjust the electrical energy to be applied to the at least one set of spaced-apart electrodes for IVL therapy.

15. A method of operating an intravascular lithotripsy (IVL) system, the method comprising:

applying a voltage pulse to at least one set of electrodes;

determining to adjust a stored energy level of the IVL system;

applying another voltage pulse to the at least one set of electrodes using an energy level different from the voltage pulse.

Exemplary Embodiment Set 6

1. An intravascular lithotripsy system comprising:

at least one set of electrodes for arrangement within a body lumen while disposed within a fluid-fillable member configured to contain a conductive fluid;

an electric pulse generation system for providing electrical energy to the at least one set of electrode to generate spark for intravascular lithotripsy (IVL) therapy, the electric pulse generation system including an IVL control system comprising a processor for executing instructions stored on memory and circuitry configured for communication of signals based on operation of the processor, the IVL control system configured to:

apply initial electrical energy to the at least one set of electrodes, determine whether a threshold parameter is achieved, and responsive to determination that the threshold parameter is not achieved, increase a duration of a pulse of electrical energy for application to the at least one set of electrodes.

2. The system of embodiment 1, wherein the IVL control system is configured to re-apply initial electrical energy to the at least one set of electrodes, responsive to determination that the threshold parameter is achieved.

3. The system of embodiment 2, wherein the threshold parameter is a value of current for achieving sufficient spark for IVL therapy.

4. The system of embodiment 3, wherein the value of current is about 20 amperes.

5. The system of embodiment 1, wherein the IVL control system is configured to repeat applying of electrical energy to the at least set of electrodes with the increased duration of the pulse of electrical energy.

6. The system of embodiment 5, wherein the IVL control system is configured to determine whether the threshold parameter is achieved under the repeat applying of electrical energy.

7. The system of embodiment 6, wherein the IVL control system is configured to re-apply the electrical energy to the at least one set of electrodes with the increased duration of the pulse of electrical energy, responsive to determination that the threshold parameter is achieved under the repeat applying of electrical energy.

8. The system of embodiment 5, wherein the threshold parameter remains the same value under the initial applying and the repeat applying.

9. The system of embodiment 5, wherein the IVL control system is configured to determine whether a maximum duration is achieved.

10. The system of embodiment 9, wherein, responsive to determination that the maximum duration is achieved, the IVL control system is configured to increase the voltage of the electrical energy applied.

11. The system of embodiment 10, wherein the IVL control system is configured to re-apply the electrical energy to the at least one set of electrodes with the increased voltage.

12. The system of embodiment 10, wherein re-applying the electrical energy to the at least one set of electrodes with the increased voltage includes adjusting the duration as presently selected.

13. The system of embodiment 12, wherein adjusting the duration as presently selected includes reducing the duration.

14. The system of embodiment 13, wherein adjusting the duration as presently selected includes resetting the duration as presently selected equal to duration under the initial electrical energy.

15. The system of embodiment 10, wherein the IVL control system is configured to determine whether a maximum voltage is achieved, and to re-apply the electrical energy to the at least one set of electrodes with the increased voltage responsive to determination that the maximum voltage is not achieved.

16. The system of embodiment 9, wherein the maximum duration remains the same value under re-applying.

17. The system of embodiment 1, wherein applying of electrical energy comprises delivery of a voltage pulse having a voltage and duration.

18. The system of embodiment 17, wherein an initial duration of the initial electrical energy delivered to the at least one electrodes is a voltage pulse having duration within the range of about 0.1 microseconds to about 2 microseconds.

19. The system of embodiment 17, wherein an initial voltage of the initial electrical energy delivered to the at least one electrodes is a voltage pulse having voltage within the range of about 500 volts to about 4000 volts.

20. A method of operating an intravascular lithotripsy system, the method comprising:

applying initial electrical energy to at least one set of electrodes of an intravascular lithotripsy (IVL) system, wherein the at least one set of electrodes is submerged within a conductive fluid contained by a fluid-fillable member;

determining whether a threshold parameter is achieved; and responsive to determination that the threshold parameter is not achieved, increasing a duration of a pulse of electrical energy for application to the at least one set of electrodes.

21. The method of embodiment 20, further comprising re-applying initial electrical energy to the at least one set of electrodes, responsive to determination that the threshold parameter is achieved.

22. The method of embodiment 21, wherein the threshold parameter is a value of current for achieving sufficient spark for IVL therapy.

23. The method of embodiment 22, wherein the value of current is about 20 amperes.

24. The method of embodiment 20, further comprising repeating applying of electrical energy to the at least set of electrodes with the increased duration of the pulse of electrical energy.

25. The method of embodiment 24, further comprising determining whether the threshold parameter is achieved under the repeat applying of electrical energy.

26. The method of embodiment 25, further comprising re-applying the electrical energy to the at least one set of electrodes with the increased duration of the pulse of electrical energy, responsive to determination that the threshold parameter is achieved under the repeat applying of electrical energy.

27. The method of embodiment 25, wherein the threshold parameter remains the same value under the initial applying and the repeat applying.

28. The method of embodiment 25, further comprising determining whether a maximum duration is achieved.

29. The method of embodiment 28, further comprising increasing the voltage of the electrical energy applied, responsive to determination that the maximum duration is achieved.

30. The method of embodiment 29, further comprising re-applying the electrical energy to the at least one set of electrodes with the increased voltage.

31. The method of embodiment 30, wherein re-applying the electrical energy to the at least one set of electrodes with the increased voltage includes adjusting the duration as presently selected.

32. The method of embodiment 31, wherein adjusting the duration as presently selected includes reducing the duration.

33. The method of embodiment 32, wherein adjusting the duration as presently selected includes resetting the duration as presently selected equal to duration under the initial electrical energy.

34. The method of embodiment 29, further comprising determining whether a maximum voltage is achieved, re-applying the electrical energy to the at least one set of electrodes with the increased voltage responsive to determination that the maximum voltage is not achieved.

35. The method of embodiment 20, wherein applying of electrical energy comprises delivery of a voltage pulse having a voltage and duration.

36. The system of embodiment 35, wherein an initial duration of the initial electrical energy delivered to the at least one electrodes is a voltage pulse having duration within the range of about 0.1 microseconds to about 2 microseconds.

37. The system of embodiment 35, wherein an initial voltage of the initial electrical energy delivered to the at least one electrodes is a voltage pulse having voltage within the range of about 500 volts to about 4000 volts.

38. An intravascular lithotripsy system comprising
- a catheter assembly comprising an elongate member defining a lumen and a fluid-fillable member configured to contain a conductive fluid and located at or near a longitudinal end of the elongate member, the catheter assembly configured to fill the fluid-fillable member with the conductive fluid to facilitate IVL therapy;
- at least one set of electrodes for arrangement within the fluid-fillable member for submerging the at least one set of electrodes within the conductive fluid;
- an IVL therapy control system comprising a processor for executing instructions stored on memory and circuitry configured for communication of signals based on operation of the processor for providing IVL therapy to a patient, the IVL therapy control system configured to apply electrical energy having initial settings, to determine whether a threshold parameter is achieved under the electrical settings, and to increase at least one of pulse duration and voltage in response to determination that the threshold parameter is not achieved.

39. A method of operating an intravascular lithotripsy (IVL) system having a catheter assembly comprising an elongate member defining a lumen and a fluid-fillable member configured to contain a conductive fluid and located at or near a longitudinal end of the elongate member, the catheter assembly configured to inflate the fluid-fillable member with the conductive fluid to facilitate IVL therapy, at least one set of electrodes for arrangement within the fluid-fillable member for submerging within the IVL fluid medium, and an IVL therapy control system comprising a processor for executing instructions stored on memory and communications circuitry configured for communication of signals based on operation of the processor for providing IVL therapy to a patient, the method comprising:
- applying electrical energy having electrical settings including initial settings;
- determining whether a threshold parameter is achieved under the applied electrical settings; and
- increasing at least one of pulse duration and voltage of the electrical settings in response to determination that the threshold parameter is not achieved.

40. An intravascular lithotripsy system comprising:
- at least one set of electrodes for arrangement within a body lumen while disposed within a fluid-fillable member configured to contain a conductive fluid;
- an electric pulse generation system for providing electrical energy to the at least one set of electrode to generate spark for intravascular lithotripsy (IVL) therapy, the electric pulse generation system including an IVL control system comprising a processor for executing instructions stored on memory and communications circuitry configured for communication of signals based on commands from the processor, IVL control system including an adjustable energy storage system for selectively adjusting the stored energy applied for providing electrical energy to the at least one set of electrodes for IVL therapy.

41. The system of embodiment 40, wherein the electric pulse generation system includes a relay system for selectively connecting a number of energy storage elements of the energy storage system for discharge to provide electrical energy to the at least one set of electrodes.

42. The system of embodiment 41, wherein in an engaged arrangement of the relay system all of the number of energy storage elements are connected to discharge to provide electrical energy to the at least one set of electrodes.

43. The system of embodiment 42, wherein in a disengaged arrangement of the relay system fewer than all of the number of the energy storage elements are connected to discharge to provide electrical energy to the at least one set of electrodes.

44. The system of embodiment 43, wherein the electrical energy provided to the at least one set of electrodes is greater under the one arrangement of the relay system than under the other arrangement of the relay system.

45. The system of embodiment 43, wherein in one pulse of electrical energy to the electrodes the relay system is in either the engaged or disengaged arrangement, and in another pulse of the electrical energy to the electrodes the relay system is in the disengaged arrangement.

46. A method of operating an intravascular lithotripsy (IVL) system, the method comprising:
- applying a first voltage pulse to at least one set of electrodes;
- determining to adjust a stored energy level of the IVL system;
- applying another voltage pulse to the at least one set of electrodes using a stored energy magnitude or level different from the first voltage pulse.

47. The method of embodiment 46, wherein applying the voltage pulse includes operating an adjustable energy storage system at a first stored energy level to apply electrical energy.

48. The method of embodiment 47, wherein applying the other voltage pulse includes operating the adjustable energy storage system at a second stored energy level to apply electrical energy.

49. The method of embodiment 48, wherein the second stored energy level is greater than the first stored energy level.

50. The method of embodiment 48, wherein the second stored energy level is less than the first stored energy level.

51. The method of embodiment 48, wherein applying the voltage pulse includes arranging a relay system to connect one or more stored energy elements of the adjustable energy storage system.

52. The method of embodiment 51, wherein arranging the relay system to connect the one or more stored energy elements of the adjustable energy storage system includes a maximum number of stored energy elements of the adjustable energy storage system.

53. The method of embodiment 51, wherein arranging the relay system to connect the one or more stored energy elements of the adjustable energy storage system includes less than a maximum number of stored energy elements of the adjustable energy storage system.

54. The method of embodiment 48, wherein applying the other voltage pulse includes arranging a relay system to connect additional stored energy elements of the adjustable energy storage system.

55. The method of embodiment 54, wherein arranging the relay system to connect the additional stored energy elements of the adjustable energy storage system includes a maximum number of stored energy elements of the adjustable energy storage system.

56. The method of embodiment 54, wherein arranging the relay system to connect the additional stored energy elements of the adjustable energy storage system includes less than a maximum number of the stored energy elements of the adjustable energy storage system.

57. The method of embodiment 47, wherein applying the voltage pulse includes arranging a relay system to connect a number of the stored energy elements of the adjustable energy storage system.

58. The method of embodiment 57, wherein arranging the relay system to connect the number of the stored energy elements of the adjustable energy storage system includes a maximum number of the stored energy elements of the adjustable energy storage system.

59. The method of embodiment 58, wherein applying the other voltage pulse includes operating the adjustable energy storage system at another stored energy magnitude to apply electrical energy.

60. The method of embodiment 57, wherein arranging the relay system to connect the number of the stored energy elements of the adjustable energy storage system includes less than a maximum number of the stored energy elements of the adjustable energy storage system.

61. The method of embodiment 60, wherein applying the other voltage pulse includes operating the adjustable energy storage system at another stored energy magnitude to apply electrical energy.

62. An intravascular lithotripsy system comprising:

at least one set of spaced-apart electrodes for arrangement within a body lumen while disposed within a fluid-fillable member configured to contain a conductive fluid;

an electric pulse generation system for providing electrical energy to the at least one set of spaced-apart electrodes to generate spark for intravascular lithotripsy (IVL) therapy, the electric pulse generation system including an IVL control system comprising a processor for executing instructions stored on memory and communications circuitry configured for communication of signals based on commands from the processor, the IVL control system including a charge control system for controlling electrical charging of a discharge system.

63. The system of embodiment 62, wherein the charge control system includes low voltage power regulator arranged to receive and control low voltage power for output for conversion to high voltage power.

64. The system of embodiment 63, wherein the charge control system receives a modulated control signal for controlling output of low voltage power for conversion to high voltage power.

65. The system of embodiment 63, wherein the charge control system is arranged to apply the modulated control signal with feedback of the output of low voltage power.

66. The system of embodiment 63, wherein the modulated control signal is a high frequency pulse width modulated signal.

67. The system of embodiment 61, wherein the charge control system includes a converter arranged to receive low voltage power and to convert low voltage power to high voltage power for communication to the discharge system.

68. The system of embodiment 67, wherein the converter is a DC-DC converter.

69. The system of embodiment 62, wherein the charge control system is configured to provide variable voltage power to the discharge system at different voltage level for consecutive cycles of charge.

70. The system of embodiment 62, wherein the discharge system includes a energy storage system and the charge control system is configured to provide variable voltage power to the discharge system at different voltage for consecutive cycles of charge after stored energy discharge.

71. An intravascular lithotripsy system comprising:

at least one set of spaced-apart electrodes for arrangement within a body lumen while disposed within a fluid-fillable member configured to contain a conductive fluid;

an electric pulse generation system for providing electrical energy to the at least one set of spaced-apart electrodes to generate spark for intravascular lithotripsy (IVL) therapy, the electric pulse generation system including an IVL control system comprising a processor for executing instructions stored on memory and communications circuitry configured for communication of signals based on commands from the processor, the IVL control system including an electrical discharge system for selectively communicating high voltage discharge to the at least one set of electrodes.

72. The system of embodiment 71, wherein the electrical discharge system comprises a discharge switching system operable to modulate communication of high voltage power to the at least one set of electrodes for IVL therapy.

73. The system of embodiment 72, wherein the discharge switching system includes at least one gate-controlled switch operable by processor signal to selectively permit communication of high voltage power to the at least one set of electrodes for IVL therapy.

74. The system of embodiment 73, where the at least one gate controlled switch is an insulated gate bipolar transistor.

75. The system of embodiment 73, where the at least one gate controlled switch is selectively operable in a permissive state permitting communication of high voltage power to the at least one set of electrodes for IVL therapy, and a non-permissive state blocking against communication of high voltage power to the at least one set of electrodes for IVL therapy.

76. The system of embodiment 71, wherein the electrical discharge system comprises an energy storage system for charging of high voltage energy for discharge to the at least one set of electrodes.

77. The system of embodiment 76, wherein the electrical discharge system comprises a discharge switching system operable to modulate communication of high voltage power from the energy storage system to the at least one set of electrodes for IVL therapy.

78. A method of operating an intravascular lithotripsy system, the method comprising:

assessing the stored energy state of a energy storage system of an intravascular lithotripsy (IVL) system to determine stored energy;

delivering a voltage pulse to at least one set of electrodes of the IVL system;

assessing the remaining energy state of the energy storage system of the IVL system to determine remaining energy; and comparing the energy states assessed to determine the energy of the voltage pulse.

79. The method of embodiment 78, wherein assessing the energy state to determine stored energy includes determining a voltage level of the energy storage system.

80. The method of embodiment 79, wherein assessing the energy state to determine stored energy includes determining a level of energy stored within the energy storage system based on the voltage level of the energy storage system.

81. The method of embodiment 78, wherein assessing the energy state to determine remaining energy includes determining a voltage level of the energy storage system.

82. The method of embodiment 81, wherein assessing the energy state to determine remaining energy includes determining a level of energy remaining within the energy storage system based on the voltage level of the energy storage system.

83. The method of embodiment 78, wherein comparing the energy states assessed includes determining the difference between the stored and remaining energy states of the energy storage system as a discharged energy.

84. The method of embodiment 83, wherein comparing the energy states assessed includes comparing the discharged energy with a threshold value.

85. The method of embodiment 84, wherein responsive to a determination that the discharged energy is equal to or greater than the threshold value, determining that sufficient spark has been generated.

86. The method of embodiment 84, wherein responsive to a determination that the discharged energy is less than the threshold value, determining that insufficient spark has been generated.

87. The method of embodiment 78, further comprising determining parameters of a further voltage pulse based on the comparison of energy states.

88. The method of embodiment 87, wherein determining parameters of the further voltage pulse includes, responsive to determination that the voltage pulse generated sufficient spark, maintaining one or more parameters of the voltage pulse for the further voltage pulse.

89. The method of embodiment 88, further comprising delivering the further voltage pulse based on the one or more maintained parameters.

90. The method of embodiment 89, repeating assessing the remaining energy state of the energy storage system of the IVL system to determine remaining energy, after delivery of the further voltage pulse.

91. The method of embodiment 87, wherein determining parameters of the further voltage pulse includes, responsive to determination that the voltage pulse generated insufficient spark, changing one or more parameters of the voltage pulse for the further voltage spark.

92. The method of embodiment 91, wherein changing one or more parameters includes changing duration of pulse for the further voltage pulse.

93. The method of embodiment 92, wherein changing duration includes increasing duration of the further voltage pulse greater than a duration of the voltage pulse.

94. The method of embodiment 92, further comprising delivering the further voltage pulse based on the one or more changed parameters.

95. The method of embodiment 94, repeating assessing the remaining energy state of the energy storage system of the IVL system to determine remaining energy, after delivery of the further voltage pulse.

96. The method of embodiment 78, wherein assessing the energy state to determine stored energy includes assessing the energy state of the energy storage system after an earlier voltage pulse has been delivered.

97. An intravascular lithotripsy system comprising:

at least one set of spaced-apart electrodes for arrangement within a body lumen while disposed within a fluid-fillable member configured to contain a conductive fluid;

an electric pulse generation system for providing electrical energy to the at least one set of spaced-apart electrodes to generate spark for intravascular lithotripsy (IVL) therapy, the electric pulse generation system including an IVL control system comprising a processor for executing instructions stored on memory and communications circuitry configured for communication of signals based on commands from the processor, wherein the IVL control system is configured to:

assess the stored energy state of a energy storage system of the IVL system to determine stored energy;

deliver a voltage pulse to at least one set of electrodes of the IVL system;

assess the remaining energy state of the energy storage system of the IVL system to determine remaining energy; and compare the energy states assessed to determine the energy of the voltage pulse.

98. The system of embodiment 97, wherein assessing the energy state to determine stored energy includes determining a voltage level of the energy storage system.

99. The system of embodiment 98, wherein assessing the energy state to determine stored energy includes determining a level of energy stored within the energy storage system based on the voltage level of the energy storage system.

100. The system of embodiment 97, wherein assessing the energy state to determine remaining energy includes determining a voltage level of the energy storage system.

101. The system of embodiment 100, wherein assessing the energy state to determine remaining energy includes determining an energy remaining within the energy storage system based on the voltage level of the energy storage system.

102. The system of embodiment 97, wherein comparing the energy states assessed includes determining the difference between the stored and remaining energy states of the energy storage system as a discharged energy.

103. The system of embodiment 102, wherein comparing the energy states assessed includes comparing the discharged energy with a threshold value.

104. The system of embodiment 103, wherein responsive to a determination that the discharged energy is equal to or greater than the threshold value, determining that sufficient spark has been generated.

105. The system of embodiment 103, wherein responsive to a determination that the discharged energy is less than the threshold value, determining that insufficient spark has been generated.

106. The system of embodiment 97, further comprising determining parameters of a further voltage pulse based on the comparison of energy states.

107. The system of embodiment 106, wherein determining parameters of the further voltage pulse includes, responsive to determination that the voltage pulse generated sufficient spark, maintaining one or more parameters of the further voltage pulse.

108. The system of embodiment 107, further comprising delivering the further voltage pulse based on the one or more maintained parameters.

109. The system of embodiment 108, repeating assessing the remaining energy state of the energy storage system of the IVL system to determine remaining energy, after delivery the further voltage pulse.

110. The method of embodiment 106, wherein determining parameters of the further voltage pulse includes, responsive to determination that the voltage pulse generated insufficient spark, changing one or more parameters of the voltage pulse for the further voltage spark.

111. The method of embodiment 110, wherein changing one or more parameters includes changing duration of pulse for the further voltage pulse.

112. The method of embodiment 111, wherein changing duration includes increasing duration of the further voltage pulse greater than a duration of the voltage pulse.

113. The method of embodiment 111, further comprising delivering the further voltage pulse based on the one or more changed parameters.

114. The method of embodiment 113, repeating assessing the remaining energy state of the energy storage system of the IVL system to determine remaining energy, after delivery of the further voltage pulse.

115. An intravascular lithotripsy system comprising:

at least one set of spaced-apart electrodes for arrangement within a body lumen while disposed within a fluid-fillable member configured to contain a conductive fluid;

an electric pulse generation system for providing electrical energy to the at least one set of spaced-apart electrodes to generate spark for intravascular lithotripsy (IVL) therapy, the electric pulse generation system including an IVL control system comprising a processor for executing instructions stored on memory and communications circuitry configured for communication of signals based on commands from the processor, wherein the electric pulse generation system comprises an electrical power system including an AC mains and a DC power storage system, wherein the AC mains are configured for connection with a AC power receptacle to receive AC power from infrastructure, and the DC power storage system is configured to receive AC power from the AC mains and to convert AC power to DC power for charging a DC power storage device of the DC power storage system, wherein the electric pulse generation system is configured to selectively provide power from the AC mains or the DC power storage system for IVL operations.

116. The system of embodiment 115, wherein IVL operations includes high voltage pulse provided to the at least one set of electrodes.

117. The system of embodiment 115, wherein the DC power storage device comprises a chemical battery.

118. The system of embodiment 115, wherein the electrical power system is configured to selectively provide power for IVL operations from stored power of the DC power storage device, from the DC power storage device while connected to receive charging power from the AC mains, or directly from the AC mains converted to DC power without the DC power storage device.

The description of devices, systems, and method and related applications as set forth herein is illustrative and is not intended to limit the scope of the invention. Features of various embodiments may be combined with other embodiments within the contemplation of this invention. Variations and modifications of the embodiments disclosed herein are possible, and practical alternatives to and equivalents of the various elements of the embodiments would be understood to those of ordinary skill in the art upon study of this patent document. These and other variations and modifications of the embodiments disclosed herein may be made without departing from the scope and spirit of the invention.

What is claimed is:

1. An intravascular lithotripsy ("IVL") console, the console comprising:

a power plug configured to be coupled to a mains power source, the power plug extending outside of an enclosure enclosing internal console circuitry;

one or more conductors coupled to the power plug;

a first isolation barrier coupled to the one or more conductors, the isolation barrier configured to electrically, according to at least a predetermined dielectric strength, isolate power from the mains power source from portions of the internal console circuitry;

wherein the internal console circuitry comprises low-voltage control circuitry and high-voltage power circuitry, wherein the high-voltage power circuitry is configured to generate a high-voltage power source for supplying high-voltage pulses to emitters in a catheter couplable to the console;

a second isolation barrier between the low-voltage control circuitry and the high-voltage power circuitry, the second isolation barrier configured to couple a first processor in the low-voltage control circuitry, configured to issue commands to the high-voltage power circuitry, to a second processor in the high-voltage power circuitry, the second processor configured to receive commands from the first processor through the isolation barrier and to perform actions to cause the high-voltage power circuitry to deliver high power pulses to emitters in the catheter; and wherein the first isolation barrier and second isolation barrier are configured such that the power plug can be coupled to the mains power source and supply power to the circuitry in the enclosure while the high-voltage power circuitry is delivering high voltage pulses to the one or more emitters in the catheter.

2. The IVL console of claim 1, wherein the console is adapted to be associated with an expandable balloon having at least two electrodes for creating a spark.

3. The IVL console of claim 1, wherein the second isolation barrier comprises magnetic coupling to achieve isolation.

4. The IVL console of claim 1, wherein the second isolation barrier comprises optical coupling to achieve isolation.

5. The IVL console of claim 1, further comprising the enclosure, the enclosure housing the internal console circuitry and providing physical protection and electromagnetic shielding for sensitive electronic components.

6. The IVL console of claim 1, further comprising at least one input interface allowing an operator to communicate with and control the console, which is electrically isolated from high-voltage sections of the IVL console.

7. The IVL console of claim 1, wherein the first isolation barrier comprises a transformer.

8. The IVL console of claim 1, wherein the system is configured to split the mains power to charge a battery and power the IVL console.

9. A method for operating an intravascular lithotripsy (IVL) console, the method comprising:

coupling a power plug to a mains power source, the power plug extending outside of an enclosure enclosing internal console circuitry;

conducting power from the mains power source through one or more conductors coupled to the power plug;

electrically isolating power from the mains power source from portions of the internal console circuitry using a first isolation barrier coupled to the one or more conductors, the isolation barrier configured to isolate power according to at least a predetermined dielectric strength;

generating a high-voltage power source using high-voltage power circuitry within the internal console circuitry, the high-voltage power circuitry configured to supply high voltage pulses to emitters in a catheter couplable to the console;

issuing commands from a first processor in low-voltage control circuitry to a second processor in the high-voltage power circuitry through a second isolation barrier, the second isolation barrier configured to couple the first processor to the second processor;

performing actions by the second processor to cause the high-voltage power circuitry to deliver high voltage pulses to emitters in the catheter;

maintaining electrical isolation between the low-voltage control circuitry and the high-voltage power circuitry using the second isolation barrier;

supplying power to the internal console circuitry while the high-voltage power circuitry is delivering high voltage pulses to the emitters in the catheter.

10. The method of claim 9, further comprising associating the console with an expandable balloon having at least two electrodes for creating a spark.

11. The method of claim 9, wherein the second isolation barrier comprises magnetic coupling to achieve isolation.

12. The method of claim 9, wherein the second isolation barrier comprises optical coupling to achieve isolation.

13. The method of claim 9, further comprising housing the internal console circuitry within an enclosure that provides physical protection and electromagnetic shielding for sensitive electronic components.

14. The method of claim 9, further comprising allowing an operator to communicate with and control the console using at least one input interface which is electrically isolated from high-voltage sections of the IVL console.

15. The method of claim 9, wherein the first isolation barrier comprises a transformer.

16. An intravascular lithotripsy (IVL) console comprising:

a power plug configured to couple to a mains power source;

a first isolation barrier coupled to one or more conductors from the power plug, the first isolation barrier configured to electrically isolate mains power from internal console circuitry according to at least a predetermined dielectric strength;

low-voltage control circuitry including a first processor;

high-voltage power circuitry including a second processor and a discharge system configured to generate high-voltage pulses; and a second isolation barrier disposed between the low-voltage control circuitry and the high-voltage power circuitry, the second isolation barrier configured to communicatively couple the first processor to the second processor while electrically isolating the low-voltage control circuitry from the high-voltage power circuitry;

wherein the first and second isolation barriers collectively enable the console to receive power from the mains power source and simultaneously deliver high-voltage pulses from the high-voltage power circuitry while maintaining electrical isolation of the low-voltage control circuitry from hazardous voltages.

17. The console of claim 16, wherein the first isolation barrier comprises a transformer configured to provide galvanic isolation from the mains supply.

18. The console of claim 16, wherein the second isolation barrier comprises at least one magnetic digital isolator.

19. The console of claim 16, wherein the second isolation barrier comprises at least one optical digital isolator.

20. The console of claim 16, wherein the low-voltage control circuitry and the high-voltage power circuitry are mounted on physically separate circuit boards separated by the second isolation barrier.

* * * * *